(12) United States Patent
Ozaki et al.

(10) Patent No.: US 9,067,005 B2
(45) Date of Patent: Jun. 30, 2015

(54) CENTRIFUGAL PUMP APPARATUS

(75) Inventors: Takayoshi Ozaki, Iwata (JP); Hiroyuki Yamada, Iwata (JP); Kenichi Suzuki, Iwata (JP); Ken Sugiura, Iwata (JP)

(73) Assignee: Thoratec Corporation, Pleasanton, CA (US)

(*) Notice: Subject to any disclaimer, the term of this patent is extended or adjusted under 35 U.S.C. 154(b) by 617 days.

(21) Appl. No.: 13/133,471

(22) PCT Filed: Nov. 10, 2009

(86) PCT No.: PCT/JP2009/069104
§ 371 (c)(1),
(2), (4) Date: Jun. 8, 2011

(87) PCT Pub. No.: WO2010/067682
PCT Pub. Date: Jun. 17, 2010

(65) Prior Publication Data
US 2011/0243759 A1 Oct. 6, 2011

(30) Foreign Application Priority Data

Dec. 8, 2008 (JP) ................................. 2008-312123
Dec. 8, 2008 (JP) ................................. 2008-312124
Dec. 11, 2008 (JP) ................................. 2008-315539
Dec. 11, 2008 (JP) ................................. 2008-315540

(51) Int. Cl.
*F04D 13/06* (2006.01)
*A61M 1/10* (2006.01)
(Continued)

(52) U.S. Cl.
CPC ........... *A61M 1/101* (2013.01); *F04D 13/0666* (2013.01); *F04D 29/0413* (2013.01);
(Continued)

(58) Field of Classification Search
CPC . A61M 1/101; A61M 1/1031; A61M 1/1017; A61M 1/1015; F16C 32/0402; F16C 33/107; F04D 13/0666; F04D 29/048; F04D 29/0413; H02K 5/1282; H02K 21/24; H02K 7/14
USPC ................. 417/352, 353, 365, 423.7, 423.11, 417/423.14, 424.1, 424.2; 310/87, 216.045; 600/16
See application file for complete search history.

(56) References Cited

U.S. PATENT DOCUMENTS 1,093,868 A   4/1914   Leighty
2,684,035 A   7/1954   Kemp
(Continued)

FOREIGN PATENT DOCUMENTS

CN   102239334 A   11/2011
CN   102341600 A   2/2012
(Continued)

OTHER PUBLICATIONS

Supplementary European Search Report issued in European Application No. 09831788.6 dated Jan. 7, 2013.
(Continued)

*Primary Examiner* — Bryan Lettman
(74) *Attorney, Agent, or Firm* — Kilpatrick Townsend & Stockton LLP

(57) ABSTRACT

A centrifugal blood pump apparatus includes an impeller provided in a blood chamber, a permanent magnet provided in one surface of the impeller, a permanent magnet provided in an inner wall of the blood chamber, a permanent magnet provided in the other surface of the impeller, and a magnetic material and a coil provided in a motor chamber for driving the impeller to rotate via a diaphragm. Grooves for hydrodynamic bearing are formed in the diaphragm facing the impeller, and in the inner wall of the blood chamber, respectively. As a result, the impeller can be smoothly activated to drive by controlling a coil current.

21 Claims, 36 Drawing Sheets

(51) Int. Cl.

| | |
|---|---|
| *F04D 29/041* | (2006.01) |
| *F04D 29/048* | (2006.01) |
| *F16C 32/04* | (2006.01) |
| *F16C 33/10* | (2006.01) |
| *H02K 5/128* | (2006.01) |
| *H02K 21/24* | (2006.01) |
| *H02K 7/14* | (2006.01) |

(52) U.S. Cl.
CPC .......... *F04D29/048* (2013.01); *F16C 32/0402* (2013.01); *F16C 33/107* (2013.01); *H02K 5/1282* (2013.01); *H02K 7/14* (2013.01); *H02K 21/24* (2013.01); *A61M 1/1015* (2014.02); *A61M 1/1017* (2014.02); *A61M 1/1031* (2014.02)

(56) References Cited

U.S. PATENT DOCUMENTS

| | | | |
|---|---|---|---|
| 3,510,229 | A | 5/1970 | Smith |
| 3,932,069 | A | 1/1976 | Giardini et al. |
| 3,960,468 | A | 6/1976 | Boorse et al. |
| 4,149,535 | A | 4/1979 | Voider |
| 4,382,199 | A | 5/1983 | Isaacson |
| 4,392,836 | A | 7/1983 | Sugawara |
| 4,507,048 | A | 3/1985 | Belenger et al. |
| 4,540,402 | A | 9/1985 | Aigner |
| 4,549,860 | A | 10/1985 | Yakich |
| 4,686,982 | A | 8/1987 | Nash |
| 4,688,998 | A | 8/1987 | Olsen et al. |
| 4,753,221 | A | 6/1988 | Kensey et al. |
| 4,769,006 | A | 9/1988 | Papantonakos |
| 4,790,843 | A | 12/1988 | Carpentier et al. |
| 4,806,080 | A | 2/1989 | Mizobuchi et al. |
| 4,817,586 | A | 4/1989 | Wampler |
| 4,846,152 | A | 7/1989 | Wampler et al. |
| 4,895,557 | A | 1/1990 | Moise et al. |
| 4,900,227 | A | 2/1990 | Trouplin |
| 4,902,272 | A | 2/1990 | Milder et al. |
| 4,906,229 | A | 3/1990 | Wampler |
| 4,908,012 | A | 3/1990 | Moise et al. |
| 4,919,647 | A | 4/1990 | Nash |
| 4,930,997 | A | 6/1990 | Bennett |
| 4,944,722 | A | 7/1990 | Carriker et al. |
| 4,957,504 | A | 9/1990 | Chardack |
| 4,964,864 | A | 10/1990 | Summers et al. |
| 4,969,865 | A | 11/1990 | Hwang et al. |
| 4,985,014 | A | 1/1991 | Orejola |
| 4,995,857 | A | 2/1991 | Arnold |
| 5,021,048 | A | 6/1991 | Buckholtz |
| 5,078,741 | A | 1/1992 | Bramm et al. |
| 5,092,844 | A | 3/1992 | Schwartz et al. |
| 5,092,879 | A | 3/1992 | Jarvik |
| 5,106,263 | A | 4/1992 | Irie |
| 5,106,273 | A | 4/1992 | Lemarquand et al. |
| 5,106,372 | A | 4/1992 | Ranford |
| 5,112,202 | A | 5/1992 | Oshima et al. |
| 5,112,349 | A | 5/1992 | Summers et al. |
| 5,129,883 | A | 7/1992 | Black |
| 5,145,333 | A | 9/1992 | Smith |
| 5,147,186 | A | 9/1992 | Buckholtz |
| 5,190,528 | A | 3/1993 | Fonger et al. |
| 5,201,679 | A | 4/1993 | Velte et al. |
| 5,211,546 | A | 5/1993 | Isaacson et al. |
| 5,275,580 | A | 1/1994 | Yamazaki |
| 5,290,227 | A | 3/1994 | Pasque |
| 5,290,236 | A | 3/1994 | Mathewson |
| 5,300,112 | A | 4/1994 | Barr |
| 5,306,295 | A | 4/1994 | Kolff et al. |
| 5,312,341 | A | 5/1994 | Turi |
| 5,332,374 | A | 7/1994 | Kricker et al. |
| 5,346,458 | A | 9/1994 | Afield |
| 5,354,331 | A | 10/1994 | Schachar |
| 5,360,445 | A | 11/1994 | Goldowsky |
| 5,370,509 | A | 12/1994 | Golding et al. |
| 5,376,114 | A | 12/1994 | Jarvik |
| 5,385,581 | A | 1/1995 | Bramm et al. |
| 5,405,383 | A | 4/1995 | Barr |
| 5,449,342 | A | 9/1995 | Hirose et al. |
| 5,478,222 | A | 12/1995 | Heidelberg et al. |
| 5,504,978 | A | 4/1996 | Meyer, III |
| 5,507,629 | A | 4/1996 | Jarvik |
| 5,533,957 | A | 7/1996 | Aldea |
| 5,569,111 | A | 10/1996 | Cho et al. |
| 5,575,630 | A | 11/1996 | Nakazawa et al. |
| 5,595,762 | A | 1/1997 | Derrieu et al. |
| 5,611,679 | A | 3/1997 | Ghosh et al. |
| 5,613,935 | A | 3/1997 | Jarvik |
| 5,643,226 | A | 7/1997 | Cosgrove et al. |
| 5,678,306 | A | 10/1997 | Bozeman, Jr. et al. |
| 5,692,882 | A | 12/1997 | Bozeman, Jr. et al. |
| 5,695,471 | A | 12/1997 | Wampler |
| 5,725,357 | A | 3/1998 | Nakazeki et al. |
| 5,738,649 | A | 4/1998 | Macoviak |
| 5,746,575 | A | 5/1998 | Westphal et al. |
| 5,746,709 | A | 5/1998 | Rom et al. |
| 5,749,855 | A | 5/1998 | Reitan |
| 5,755,784 | A | 5/1998 | Jarvik |
| 5,776,111 | A | 7/1998 | Tesio |
| 5,800,559 | A | 9/1998 | Higham et al. |
| 5,807,311 | A | 9/1998 | Palestrant |
| 5,814,011 | A | 9/1998 | Corace |
| 5,824,069 | A | 10/1998 | Lemole |
| 5,851,174 | A | 12/1998 | Jarvik et al. |
| 5,853,394 | A | 12/1998 | Tolkoff et al. |
| 5,868,702 | A | 2/1999 | Stevens et al. |
| 5,868,703 | A | 2/1999 | Bertolero et al. |
| 5,890,883 | A | 4/1999 | Golding et al. |
| 5,911,685 | A | 6/1999 | Siess et al. |
| 5,921,913 | A | 7/1999 | Siess |
| 5,924,848 | A | 7/1999 | Izraelev |
| 5,924,975 | A | 7/1999 | Goldowsky |
| 5,928,131 | A | 7/1999 | Prem |
| 5,938,412 | A | 8/1999 | Izraelev |
| 5,941,813 | A | 8/1999 | Sievers et al. |
| 5,947,703 | A | 9/1999 | Nojiri et al. |
| 5,951,263 | A | 9/1999 | Taylor et al. |
| 5,964,694 | A | 10/1999 | Siess et al. |
| 6,004,269 | A | 12/1999 | Crowley et al. |
| 6,007,479 | A | 12/1999 | Rottenberg et al. |
| 6,030,188 | A | 2/2000 | Nojiri et al. |
| 6,042,347 | A | 3/2000 | Scholl et al. |
| 6,053,705 | A | 4/2000 | Schob et al. |
| 6,058,593 | A | 5/2000 | Siess |
| 6,066,086 | A | 5/2000 | Antaki et al. |
| 6,071,093 | A * | 6/2000 | Hart .................... 417/424.2 |
| 6,074,180 | A | 6/2000 | Khanwilkar et al. |
| 6,080,133 | A | 6/2000 | Wampler |
| 6,082,900 | A | 7/2000 | Takeuchi et al. |
| 6,083,260 | A | 7/2000 | Aboul-Hosn |
| 6,086,527 | A | 7/2000 | Talpade |
| 6,100,618 | A | 8/2000 | Schoeb et al. |
| 6,123,659 | A | 9/2000 | leBlanc et al. |
| 6,123,726 | A | 9/2000 | Mori et al. |
| 6,139,487 | A | 10/2000 | Siess |
| 6,142,752 | A | 11/2000 | Akamatsu et al. |
| 6,143,025 | A | 11/2000 | Stobie et al. |
| 6,146,325 | A | 11/2000 | Lewis et al. |
| 6,149,683 | A | 11/2000 | Lancisi et al. |
| 6,158,984 | A | 12/2000 | Cao et al. |
| 6,171,078 | B1 | 1/2001 | Schob |
| 6,176,822 | B1 | 1/2001 | Nix et al. |
| 6,176,848 | B1 | 1/2001 | Rau et al. |
| 6,190,304 | B1 | 2/2001 | Downey et al. |
| 6,200,260 | B1 | 3/2001 | Bolling |
| 6,206,659 | B1 | 3/2001 | Izraelev |
| 6,227,797 | B1 | 5/2001 | Watterson et al. |
| 6,227,820 | B1 | 5/2001 | Jarvik |
| 6,234,772 | B1 | 5/2001 | Wampler et al. |
| 6,234,998 | B1 | 5/2001 | Wampler |
| 6,245,007 | B1 | 6/2001 | Bedingham et al. |
| 6,247,892 | B1 | 6/2001 | Kazatchkov et al. |
| 6,254,359 | B1 | 7/2001 | Aber |

(56) References Cited

U.S. PATENT DOCUMENTS

| | | |
|---|---|---|
| 6,264,635 B1 | 7/2001 | Wampler et al. |
| 6,293,901 B1 | 9/2001 | Prem |
| 6,295,877 B1 | 10/2001 | Aboul-Hosn et al. |
| 6,319,231 B1 | 11/2001 | Andrulitis |
| 6,351,048 B1 | 2/2002 | Schob et al. |
| 6,375,607 B1 | 4/2002 | Prem |
| 6,387,037 B1 | 5/2002 | Bolling et al. |
| 6,422,990 B1 | 7/2002 | Prem |
| 6,425,007 B1 | 7/2002 | Messinger |
| 6,428,464 B1 | 8/2002 | Bolling |
| 6,439,845 B1 * | 8/2002 | Veres .................. 415/206 |
| 6,447,266 B2 | 9/2002 | Antaki et al. |
| 6,447,441 B1 | 9/2002 | Yu et al. |
| 6,458,163 B1 | 10/2002 | Slemker et al. |
| 6,508,777 B1 | 1/2003 | Macoviak et al. |
| 6,508,787 B2 | 1/2003 | Erbel et al. |
| 6,517,315 B2 | 2/2003 | Belady |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | deBlanc et al. |
| 6,547,530 B2 | 4/2003 | Ozaki et al. |
| 6,595,762 B2 | 7/2003 | Khanwilkar et al. |
| 6,609,883 B2 | 8/2003 | Woodard et al. |
| 6,610,004 B2 | 8/2003 | Viole et al. |
| 6,623,420 B2 | 9/2003 | Reich et al. |
| 6,641,558 B1 | 11/2003 | Aboul-Hosn et al. |
| 6,688,861 B2 | 2/2004 | Wampler |
| 6,692,318 B2 | 2/2004 | McBride |
| 6,698,097 B1 | 3/2004 | Miura et al. |
| 6,709,418 B1 | 3/2004 | Aboul-Hosn et al. |
| 6,716,189 B1 | 4/2004 | Jarvik et al. |
| 6,732,501 B2 | 5/2004 | Yu et al. |
| 6,749,598 B1 | 6/2004 | Keren et al. |
| 6,776,578 B2 | 8/2004 | Belady |
| 6,790,171 B1 | 9/2004 | Griindeman et al. |
| 6,794,789 B2 | 9/2004 | Siess et al. |
| 6,808,371 B2 | 10/2004 | Niwatsukino et al. |
| 6,817,836 B2 | 11/2004 | Nose et al. |
| 6,860,713 B2 | 3/2005 | Hoover |
| 6,926,662 B1 | 8/2005 | Aboul-Hosn et al. |
| 6,935,344 B1 | 8/2005 | Aboul-Hosn et al. |
| 6,942,672 B2 | 9/2005 | Heilman et al. |
| 6,949,066 B2 | 9/2005 | Beamson et al. |
| 6,966,748 B2 | 11/2005 | Woodard et al. |
| 6,974,436 B1 | 12/2005 | Aboul-Hosn et al. |
| 6,991,595 B2 | 1/2006 | Burke et al. |
| 7,010,954 B2 | 3/2006 | Siess et al. |
| 7,011,620 B1 | 3/2006 | Siess |
| 7,022,100 B1 | 4/2006 | Aboul-Hosn et al. |
| 7,027,875 B2 | 4/2006 | Siess et al. |
| 7,048,681 B2 | 5/2006 | Tsubouchi et al. |
| 7,112,903 B1 | 9/2006 | Schob |
| 7,122,019 B1 | 10/2006 | Kesten et al. |
| 7,128,538 B2 | 10/2006 | Tsubouchi et al. |
| 7,156,802 B2 | 1/2007 | Woodard et al. |
| 7,160,243 B2 | 1/2007 | Medvedev |
| 7,172,551 B2 | 2/2007 | Leasure |
| 7,175,588 B2 | 2/2007 | Morello |
| 7,241,257 B1 | 7/2007 | Ainsworth et al. |
| 7,329,236 B2 | 2/2008 | Kesten et al. |
| 7,331,921 B2 | 2/2008 | Viole et al. |
| 7,335,192 B2 | 2/2008 | Keren et al. |
| 7,393,181 B2 | 7/2008 | McBride et al. |
| 7,431,688 B2 | 10/2008 | Wampler et al. |
| 7,467,930 B2 | 12/2008 | Ozaki et al. |
| 7,470,246 B2 | 12/2008 | Mori et al. |
| 7,476,077 B2 | 1/2009 | Woodard et al. |
| 7,491,163 B2 | 2/2009 | Viole et al. |
| 7,575,423 B2 | 8/2009 | Wampler |
| 7,645,225 B2 | 1/2010 | Medvedev et al. |
| 7,699,586 B2 | 4/2010 | LaRose et al. |
| 7,731,675 B2 | 6/2010 | Aboul-Hosn et al. |
| 7,748,964 B2 | 7/2010 | Yaegashi et al. |
| 7,802,966 B2 | 9/2010 | Wampler et al. |
| 7,841,976 B2 | 11/2010 | McBride et al. |
| 7,888,242 B2 | 2/2011 | Tanaka et al. |
| 7,934,909 B2 | 5/2011 | Nuesser et al. |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,096,935 B2 | 1/2012 | Sutton et al. |
| 8,123,669 B2 | 2/2012 | Siess et al. |
| 8,226,373 B2 | 7/2012 | Yaegashi |
| 8,282,359 B2 | 10/2012 | Ayre et al. |
| 8,283,829 B2 | 10/2012 | Yamamoto et al. |
| 8,366,381 B2 | 2/2013 | Woodard et al. |
| 8,403,823 B2 | 3/2013 | Yu et al. |
| 8,512,012 B2 | 8/2013 | Akdis et al. |
| 2001/0039369 A1 | 11/2001 | Terentiev |
| 2002/0058994 A1 | 5/2002 | Hill et al. |
| 2002/0095210 A1 | 7/2002 | Finnegan et al. |
| 2003/0023302 A1 | 1/2003 | Moe et al. |
| 2004/0007515 A1 | 1/2004 | Geyer |
| 2004/0015232 A1 | 1/2004 | Shu et al. |
| 2004/0024285 A1 | 2/2004 | Muckter |
| 2004/0030381 A1 | 2/2004 | Shu |
| 2004/0171905 A1 | 9/2004 | Yu et al. |
| 2004/0210305 A1 | 10/2004 | Shu et al. |
| 2005/0089422 A1 | 4/2005 | Ozaki et al. |
| 2005/0287022 A1 | 12/2005 | Yaegashi et al. |
| 2006/0024182 A1 | 2/2006 | Akdis et al. |
| 2006/0055274 A1 * | 3/2006 | Kim .................. 310/216 |
| 2007/0078293 A1 | 4/2007 | Shambaugh et al. |
| 2007/0134993 A1 | 6/2007 | Tamez et al. |
| 2007/0213690 A1 | 9/2007 | Phillips et al. |
| 2007/0231135 A1 | 10/2007 | Wampler et al. |
| 2007/0297923 A1 * | 12/2007 | Tada .................. 417/356 |
| 2008/0021394 A1 | 1/2008 | LaRose et al. |
| 2008/0030895 A1 | 2/2008 | Obara et al. |
| 2008/0095648 A1 | 4/2008 | Wampler et al. |
| 2008/0124231 A1 * | 5/2008 | Yaegashi .................. 417/417 |
| 2009/0060743 A1 | 3/2009 | McBride et al. |
| 2009/0074336 A1 | 3/2009 | Engesser et al. |
| 2009/0171136 A1 | 7/2009 | Shambaugh, Jr. |
| 2010/0185280 A1 | 7/2010 | Ayre et al. |
| 2010/0266423 A1 | 10/2010 | Gohean et al. |
| 2011/0118766 A1 | 5/2011 | Reichenbach et al. |
| 2011/0118829 A1 | 5/2011 | Hoarau et al. |
| 2011/0118833 A1 | 5/2011 | Reichenbach et al. |
| 2011/0129373 A1 | 6/2011 | Mori |
| 2011/0243759 A1 | 10/2011 | Ozaki et al. |
| 2011/0318203 A1 | 12/2011 | Ozaki et al. |
| 2012/0003108 A1 | 1/2012 | Ozaki et al. |
| 2012/0016178 A1 | 1/2012 | Woodard et al. |
| 2012/0035411 A1 | 2/2012 | LaRose et al. |
| 2012/0078030 A1 | 3/2012 | Bourque |
| 2012/0130152 A1 | 5/2012 | Ozaki et al. |
| 2012/0243759 A1 | 9/2012 | Fujisawa |
| 2012/0308363 A1 | 12/2012 | Ozaki et al. |
| 2013/0121821 A1 | 5/2013 | Ozaki et al. |
| 2013/0170970 A1 | 7/2013 | Ozaki et al. |
| 2013/0178694 A1 | 7/2013 | Jeffery et al. |
| 2013/0243623 A1 | 9/2013 | Okawa et al. |
| 2014/0030122 A1 | 1/2014 | Ozaki et al. |

FOREIGN PATENT DOCUMENTS

| | | |
|---|---|---|
| EP | 1113117 A2 | 7/2001 |
| EP | 1495773 A2 | 1/2005 |
| EP | 1495773 A3 | 11/2006 |
| EP | 1495773 B1 | 2/2009 |
| EP | 2372160 A1 | 10/2011 |
| EP | 2405140 A1 | 1/2012 |
| EP | 2461465 A1 | 6/2012 |
| JP | 04-091396 | 3/1992 |
| JP | 2004/148094 A | 5/1992 |
| JP | 05-021197 U | 3/1993 |
| JP | 2006/014538 U | 2/1994 |
| JP | 06-053790 U | 7/1994 |
| JP | 2007/014220 U | 3/1995 |
| JP | 2007/042869 U | 8/1995 |
| JP | 2007/509156 A | 10/1995 |
| JP | 2009/122228 A | 5/1997 |

(56) References Cited

FOREIGN PATENT DOCUMENTS

| | | | |
|---|---|---|---|
| JP | 2010/331841 A | 12/1998 | |
| JP | 2011/244377 A | 9/1999 | |
| JP | 2001-309628 | 11/2001 | |
| JP | 2003/135592 A | 5/2003 | |
| JP | 2004/166401 A | 6/2004 | |
| JP | 2004-209240 | 7/2004 | |
| JP | 2004/332566 A | 11/2004 | |
| JP | 2004/346925 A | 12/2004 | |
| JP | 2005/127222 A | 5/2005 | |
| JP | 2005270415 * | 6/2005 | ............. A61M 1/10 |
| JP | 2005/270345 A | 10/2005 | |
| JP | 2005/270415 A | 10/2005 | |
| JP | 2005/287599 A | 10/2005 | |
| JP | 2006-167173 | 6/2006 | |
| JP | 2007/002885 A | 1/2007 | |
| JP | 2007-043821 | 2/2007 | |
| JP | 2007-089972 A | 4/2007 | |
| JP | 2007-089974 | 4/2007 | |
| JP | 2007-215292 | 8/2007 | |
| JP | 2004-247489 | 9/2007 | |
| JP | 2007-247489 | 9/2007 | |
| JP | 2008-104278 | 5/2008 | |
| JP | 2008-132131 | 6/2008 | |
| JP | 2008/297997 A | 12/2008 | |
| JP | 2010/136863 A | 6/2010 | |
| WO | 93/07388 A1 | 4/1993 | |
| WO | 96-31934 | 10/1996 | |
| WO | 97-42413 A1 | 11/1997 | |
| WO | 2005/028000 A1 | 3/2005 | |
| WO | 2005-034312 A2 | 4/2005 | |
| WO | 2010/067682 A1 | 6/2010 | |
| WO | 2010/101082 A1 | 9/2010 | |
| WO | 2011-013483 A1 | 2/2011 | |

OTHER PUBLICATIONS

Extended European Search Report issued in European Patent Application No. EP 10748677.1, mailed Nov. 19, 2012, 5 pages.
International Search Report (PCT/ISA/210) issued on Jul. 14, 2009, by Japanese Patent Office as the International Searching Authority for International Application No. PCT/JP2009/061318, 4 pages.
International Search Report and Written Opinion issued in PCT/JP2011/050925, mailed Apr. 12, 2011, 4 pages.
International Search Report and Written Opinion issued in PCT/JP2011/054134, mailed Apr. 12, 2011, 5 pages.
International Search Report and Written Opinion issued in PCT/JP2011/064768, mailed Sep. 13, 2011, 5 pages.
International Search Report and Written Opinion issued in PCT/JP2011/070450, mailed Dec. 13, 2011, 3 pages.
International Search Report and Written Opinion of PCT/US2014/012448 mailed on Feb. 19, 2014, 8 pages.
Kosaka, et al., "Operating Point Control System for a Continuous Flow Artificial Heart: In Vitro Study," ASAIO Journal 2003, 6 pages.
Intternational Search Report and Written Opinion issued in PCT/US2014/012511 mailed on May 14, 2014, 13 pages.
Supplementary European Search Report issued in European Application No. 09831788.6, dated Jan. 7, 2013.
European Search Report issued in European Patent Application No. 10/748,702.7 dated Apr. 2, 2013.
Asama, et al., "Suspension Performance of a Two-Axis Actively Regulated Consequent-Pole Bearingless Motor," IEEE Transactions On Energy Conversion, vol. 28, No. 4, Dec. 2013, 8 pages.
Terumo Heart, Inc., "Handled With Care—Significantly Reduce the Risk of Cell Damage," Terumo brochure, Apr. 2010, 2 pages.
Yamazaki, et al., "Development of a Miniature Intraventricular Axial Flow Blood Pump," ASAIO Journal, 1993, 7 pages.

\* cited by examiner

CENTRIFUGAL PUMP APPARATUS

RELATED APPLICATIONS

This application is the U.S. National Phase under 35 U.S.C. §371 of International Application No. PCT/JP2009/069104, filed on Nov. 10, 2009, which in turn claims the benefit of Japanese Application No. 2008-312123, filed on Dec. 8, 2008, Japanese Application No. 2008-312124, filed on Dec. 8, 2008, Japanese Application No. 2008-315539, filed on Dec. 11, 2008 and Japanese Application No. 2008-315540, filed on Dec. 11, 2008, the disclosures of which Applications are incorporated by reference herein.

TECHNICAL FIELD

The present invention relates to a centrifugal pump apparatus, and more particularly to a centrifugal pump apparatus including an impeller for delivering liquid by centrifugal force during rotation.

BACKGROUND ART

In recent years, a centrifugal blood pump apparatus in which driving torque from an external motor is transmitted to an impeller in a blood chamber through magnetic coupling has been increasingly used as a blood circulation apparatus of an artificial heart-lung machine. According to such centrifugal blood pump apparatus, physical contact between the blood chamber and the outside can be eliminated, thus preventing invasion of bacteria and the like into blood.

A centrifugal blood pump in Patent Document 1 (Japanese Patent Laying-Open No. 2004-209240) includes a housing having first to third chambers partitioned from one another by first and second diaphragms, an impeller rotatably provided in the second chamber (blood chamber), a magnetic material provided in one surface of the impeller, an electromagnet provided in the first chamber to face the one surface of the impeller, a permanent magnet provided in the other surface of the impeller, a rotor and a motor provided in the third chamber, and a permanent magnet provided in the rotor to face the other surface of the impeller. A groove for hydrodynamic bearing is formed in a surface of the second diaphragm facing the other surface of the impeller. Due to attractive force acting on the one surface of the impeller from the electromagnet, attractive force acting on the other surface of the impeller from the permanent magnet in the rotor, and a hydrodynamic bearing effect of the grooves for hydrodynamic bearing, the impeller moves away from an inner surface of the second chamber, and rotates without contacting.

A centrifugal blood pump in Patent Document 2 (Japanese Patent Laying-Open No. 2006-167173) includes a housing having first to third chambers partitioned from one another by first and second diaphragms, an impeller rotatably provided in the second chamber (blood chamber), a magnetic material provided in one surface of the impeller, a first permanent magnet provided in the first chamber to face the one surface of the impeller, a second permanent magnet provided in the other surface of the impeller, a rotor and a motor provided in the third chamber, and a third permanent magnet provided in the rotor to face the other surface of the impeller. A first grooves for hydrodynamic bearing is formed in a surface of the first diaphragm facing the one surface of the impeller, and a second grooves for hydrodynamic bearing is formed in a surface of the second diaphragm facing the other surface of the impeller. Due to attractive force acting on the one surface of the impeller from the first permanent magnet, attractive force acting on the other surface of the impeller from the third permanent magnet in the rotor, and a hydrodynamic bearing effect of the first and second grooves for hydrodynamic bearing, the impeller moves away from an inner surface of the second chamber, and rotates without contacting.

A turbo-type pump in FIGS. 8 and 9 of Patent Document 3 (Japanese Patent Laying-Open No. 4-91396) includes a housing, an impeller rotatably provided in the housing, a first permanent magnet provided in one surface of the impeller, a rotor provided outside of the housing, a second permanent magnet provided in the rotor to face the one surface of the impeller, a third permanent magnet provided in the other surface of the impeller, and a magnetic material provided in the housing to face the other surface of the impeller. A first grooves for hydrodynamic bearing is formed in the one surface of the impeller, and a second grooves for hydrodynamic bearing is formed in the other surface of the impeller. Due to attractive force acting on the one surface of the impeller from the second permanent magnet in the rotor, attractive force acting on the other surface of the impeller from the magnetic material in the housing, and a hydrodynamic bearing effect of the first and second grooves for hydrodynamic bearing, the impeller moves away from an inner surface of the housing, and rotates without contacting.

A clean pump in Patent Document 4 (Japanese Utility Model Laying-Open No. 6-53790) includes a casing, an impeller rotatably provided in the casing, a first permanent magnet provided in one surface of the impeller, a rotor provided outside of the casing, a second permanent magnet provided in the rotor to face the one surface of the impeller, a magnetic material provided in the other surface of the impeller, and an electromagnet provided outside of the housing to face the other surface of the impeller. A grooves for hydrodynamic bearing is formed in the one surface of the impeller.

The electromagnet is operated when a rotation speed of the impeller is lower than a predetermined rotation speed, and power supply to the electromagnet is stopped when the rotation speed of the impeller becomes higher than the predetermined rotation speed. Due to attractive force acting on the one surface of the impeller from the second permanent magnet in the rotor, and a hydrodynamic bearing effect of the grooves for hydrodynamic bearing, the impeller moves away from an inner surface of the housing, and rotates without contacting.

PRIOR ART DOCUMENTS

Patent Documents

Patent Document 1: Japanese Patent Laying-Open No. 2004-209240
Patent Document 2: Japanese Patent Laying-Open No. 2006-167173
Patent Document 3: Japanese Patent Laying-Open No. 4-91396
Patent Document 4: Japanese Utility Model Laying-Open No. 6-53790

SUMMARY OF THE INVENTION

Problems to be Solved by the Invention

The pumps in Patent Documents 1 to 4 described above share the feature of axially supporting the impeller by the grooves for hydrodynamic bearing formed in a portion where the impeller and the housing face each other, and radially supporting the impeller by the attractive force between the permanent magnet provided in the impeller and the permanent magnet provided outside of the housing.

Supporting rigidity of a grooves for hydrodynamic bearing is proportionate to a rotation speed of an impeller. Thus, in order for an impeller to stably rotate without contacting a housing even when disturbance is applied to a pump, axial rigidity for the impeller needs to be enhanced by increasing a normal rotation speed range of the pump. In the pumps of Patent Documents 1 to 4 described above, however, the impeller is radially supported by utilizing the attractive force of the permanent magnets, and so the supporting rigidity is low, resulting in inability to rotate the impeller at high speed.

One way to increase the radial rigidity is to increase the attractive force between the permanent magnet in the impeller and the permanent magnet or a stator provided outside of the housing. As the attractive force is increased, however, a negative axial rigidity value of the impeller increases (namely, as the impeller moves axially, the attractive force increases correspondingly). Thus, supporting function on the impeller by hydrodynamic pressure and the attractive force acting between the impeller and the housing increase, resulting in difficulty in smoothly driving the impeller to rotate.

In particular, when an impeller is rotated by magnetic interaction between an outside motor coil and a permanent magnet provided in the impeller as shown in FIG. 39 of Patent Document 2, starting torque is small as compared to an example where an impeller is driven to rotate through magnetic coupling between permanent magnets as shown in FIG. 3 of Patent Document 2, resulting in difficulty in smoothly driving the impeller to rotate.

To solve this problem, Patent Document 2 proposes a method of providing an electromagnet for biasing the impeller toward a predetermined direction, and a magnetic force adjustment coil for varying magnetic force of the permanent magnets, and operating them when activating the impeller to rotate, to smoothly activate the impeller. However, this approach requires new dedicated members such as the electromagnet and the coil, which increases a pump size, and the increased number of components results in lower reliability. These are serious problems for a blood pump for use in an artificial heart or the like. Further, since a hydrodynamic bearing does not actively perform position control of an impeller, position of an impeller may be changed depending on a rotation speed of the impeller and viscosity of pump fluid. Adding a new sensor for measuring the position of the impeller increases the number of components and results in lower reliability. These are serious problems for a blood pump for use in an artificial heart or the like.

In view of the above, a main object of the present invention is to provide a small centrifugal pump apparatus capable of rotating an impeller at high speed, and smoothly activating the impeller to rotate.

Means for Solving the Problems

A centrifugal pump apparatus according to the present invention is a centrifugal pump apparatus including a housing having first and second chambers partitioned from each other by a diaphragm, an impeller rotatably provided in the first chamber along the diaphragm, for delivering liquid by centrifugal force during rotation, and a drive unit provided in the second chamber for driving the impeller to rotate via the diaphragm, and includes a first magnetic material provided in one surface of the impeller, a second magnetic material provided in an inner wall of the first chamber facing the one surface of the impeller, for attracting the first magnetic material, and a plurality of third magnetic materials provided in the other surface of the impeller, and arranged along a single circle such that adjacent magnetic polarities thereof are different from each other. The drive unit includes a plurality of fourth magnetic materials arranged to face the plurality of third magnetic materials, and a plurality of coils provided correspondingly to the plurality of fourth magnetic materials, respectively, each being wound around a corresponding one of the fourth magnetic materials for generating a rotating magnetic field. During rotation of the impeller, a first attractive force between the first and second magnetic materials and a second attractive force between the plurality of third magnetic materials and the plurality of fourth magnetic materials are balanced with each other substantially in a center of a movable range of the impeller in the first chamber. A first grooves for hydrodynamic bearing is formed in the one surface of the impeller or in the inner wall of the first chamber facing the one surface, and a second grooves for hydrodynamic bearing is formed in the other surface of the impeller or in the diaphragm facing the other surface. In this manner, each of the fourth magnetic materials is provided in each coil of the drive unit, and the fourth magnetic materials are magnetically coupled to the third magnetic materials in the impeller. Accordingly, the impeller can be rotated at high speed by adjusting a coil current, and a force for activating the impeller to rotate can be increased while maintaining a small pump size.

Preferably, a sum of an absolute value of a negative axial supporting rigidity value of the impeller which is constituted of the first and second attractive forces and an absolute value of a positive radial rigidity value of the impeller is smaller than an absolute value of a positive rigidity value obtained by the first and second grooves for hydrodynamic bearing in a normal rotation speed range where the impeller rotates. In this case, movement of the impeller by the action of disturbance force on the impeller can be suppressed, thereby avoiding mechanical contact between the impeller and the housing.

Preferably, a hydrodynamic pressure generated by the first grooves for hydrodynamic bearing is different from a hydrodynamic pressure generated by the second grooves for hydrodynamic bearing. In this case, when disturbance such as hydrodynamic force acts on the impeller always in one direction during pumping, the function of the grooves for hydrodynamic bearing in the disturbance direction may be made greater than the function of the other grooves for hydrodynamic bearing in the impeller, thereby levitating and rotating the impeller in the central position of the housing. As a result, mechanical contact between the impeller and the housing can be reduced, thereby stably levitating the impeller.

Preferably, at least one of the first and second grooves for hydrodynamic bearing is an inward spiral groove. In this case, the liquid can be smoothly flown.

Preferably, each of the first to third magnetic materials is a permanent magnet. Preferably, the fourth magnetic materials are made of a soft magnetic material.

Preferably, the impeller is in contact with the diaphragm when the impeller is activated to rotate. In this case, the impeller can be smoothly activated to rotate.

Preferably, the centrifugal pump apparatus further includes a control unit for causing the impeller to contact the diaphragm when the impeller is activated to rotate.

Preferably, the control unit causes the impeller to contact the diaphragm when the impeller is activated to rotate, by causing a current to flow through the plurality of coils such that the second attractive force becomes higher than the first attractive force.

Preferably, the control unit causes the impeller to contact the diaphragm when the impeller is activated to rotate, by causing a first current to flow through the plurality of coils, and then causes the impeller to rotate by causing a second current smaller than the first current to flow through the plurality of coils.

Preferably, a diamond-like carbon coating for reducing frictional force is formed on at least one of a surface of the impeller and the inner wall of the first chamber. In this case, friction between the impeller and the housing can be alleviated, to smoothly activate the impeller to rotate.

Preferably, surfaces facing each other of every two adjacent fourth magnetic materials are provided substantially parallel to each other. In this case, large space for the coils can be secured, to increase turns of the coils. As a result, large torque for driving the impeller to rotate can be generated. Further, copper loss that occurs in the motor coils can be reduced, thereby increasing energy efficiency when driving the impeller to rotate.

Preferably, the centrifugal pump apparatus further includes a fifth magnetic material provided correspondingly to each of the fourth magnetic materials, on a tip surface of a corresponding one of the fourth magnetic materials facing one of the third magnetic materials, wherein a surface of the fifth magnetic material facing the third magnetic material has an area larger than an area of the tip surface of the fourth magnetic material. In this case, the attractive force between the third magnetic materials and the drive unit can be increased, thereby increasing energy efficiency when driving the impeller to rotate.

Preferably, each of the fourth magnetic materials includes a plurality of steel plates stacked in a length direction of a rotation axis of the impeller. In this case, eddy current loss that occurs in the fourth magnetic materials can be reduced, thus increasing energy efficiency when driving the impeller to rotate.

Preferably, each of the fourth magnetic materials includes a plurality of steel plates stacked in a rotation direction of the impeller. In this case, eddy current loss that occurs in the fourth magnetic materials can be reduced, thus increasing energy efficiency when driving the impeller to rotate.

Preferably, each of the fourth magnetic materials includes a plurality of steel plates stacked in a radial direction of the impeller. In this case, eddy current loss that occurs in the fourth magnetic materials can be reduced, thus increasing energy efficiency when driving the impeller to rotate.

Preferably, each of the fourth magnetic materials is made of powders of pure iron, soft iron, or ferrosilicon. In this case, iron loss in the fourth magnetic materials can be reduced, thus increasing energy efficiency when driving the impeller to rotate.

Preferably, the centrifugal pump apparatus further includes a magnetic sensor provided in the second chamber to face a path through which the plurality of third magnetic materials pass, for detecting variation in magnetic field associated with rotation and change of position of the impeller, and a control unit for causing a current to flow through the plurality of coils based on a detection result from the magnetic sensor, to generate a rotating magnetic field to drive the impeller to rotate.

Preferably, the centrifugal pump apparatus further includes a first operation unit for determining an axial position of the impeller in the first chamber based on the detection result from the magnetic sensor. In this case, the axial position of the impeller is determined by using the magnetic sensor for detecting timing for feeding a current through the plurality of coils, thereby increasing reliability of the apparatus without increasing the number of components.

Preferably, the first operation unit outputs information indicating the axial position of the impeller to outside.

Preferably, the centrifugal pump apparatus further includes a determination unit for determining whether or not the axial position of the impeller determined by the first operation unit is within a normal range, and outputting a signal indicating a determination result.

Preferably, the centrifugal pump apparatus further includes a second operation unit for determining a rotation speed of the impeller based on the detection result from the magnetic sensor, and a determination unit for determining whether or not an axial position of the impeller is within a normal range based on the axial position of the impeller determined by the first operation unit and the rotation speed of the impeller determined by the second operation unit, and outputting a signal indicating a determination result.

Preferably, the centrifugal pump apparatus further includes a determination unit for determining whether or not an axial position of the impeller is within a normal range based on the axial position of the impeller determined by the first operation unit and viscosity information on the liquid, and outputting a signal indicating a determination result.

Preferably, the centrifugal pump apparatus further includes a first detection unit for detecting a voltage applied to each of the coils, a second detection unit for detecting a current flowing through each of the coils, and an operation unit for determining an axial position of the impeller in the first chamber based on detection results from the first and second detection units and information indicating a rotation speed of the impeller. In this case, since the axial position of the impeller is determined based on the coil voltage, the coil current, and the information indicating a rotation speed of the impeller, a levitation state of the impeller can be monitored while maintaining the dimensions of the housing without increasing the number of components in the housing, thereby increasing reliability of the apparatus.

Preferably, the operation unit determines a ratio between the voltage detected by the first detection unit and the current detected by the second detection unit, and determines the axial position of the impeller in the first chamber based on the ratio and the information indicating a rotation speed of the impeller.

Preferably, the centrifugal pump apparatus further includes a determination unit for determining whether or not the axial position of the impeller determined by the operation unit is within a normal range, and outputting a signal indicating a determination result.

Preferably, the centrifugal pump apparatus further includes a determination unit for determining whether or not an axial position of the impeller is within a normal range based on the axial position of the impeller determined by the operation unit and the information indicating a rotation speed of the impeller, and outputting a signal indicating a determination result.

Preferably, the centrifugal pump apparatus further includes a determination unit for determining whether or not an axial position of the impeller is within a normal range based on the axial position of the impeller determined by the operation unit, the information indicating a rotation speed of the impeller, and viscosity information on the liquid, and outputting a signal indicating a determination result.

Preferably, the liquid is blood, and the centrifugal pump apparatus is used for circulating the blood. In this case, the impeller is smoothly activated to rotate, and a distance between the impeller and the housing is secured, thereby preventing occurrence of hemolysis.

Effects of the Invention

As described above, according to the present invention, the impeller can be rotated at high speed, and a force to activate the impeller to rotate can be increased while maintaining a small pump size. Further, mechanical contact between the impeller and the housing can be reduced, to stably levitate the impeller. Further, liquid can be smoothly flown. Further, the impeller can be smoothly activated to rotate. Further, large torque for driving the impeller to rotate can be generated. Further, energy efficiency when driving the impeller to rotate can be increased. Moreover, reliability of the apparatus can be enhanced without increasing the number of components. Furthermore, hemolysis can be avoided when circulating blood.

MODES FOR CARRYING OUT THE INVENTION

First Embodiment

Figure 1:
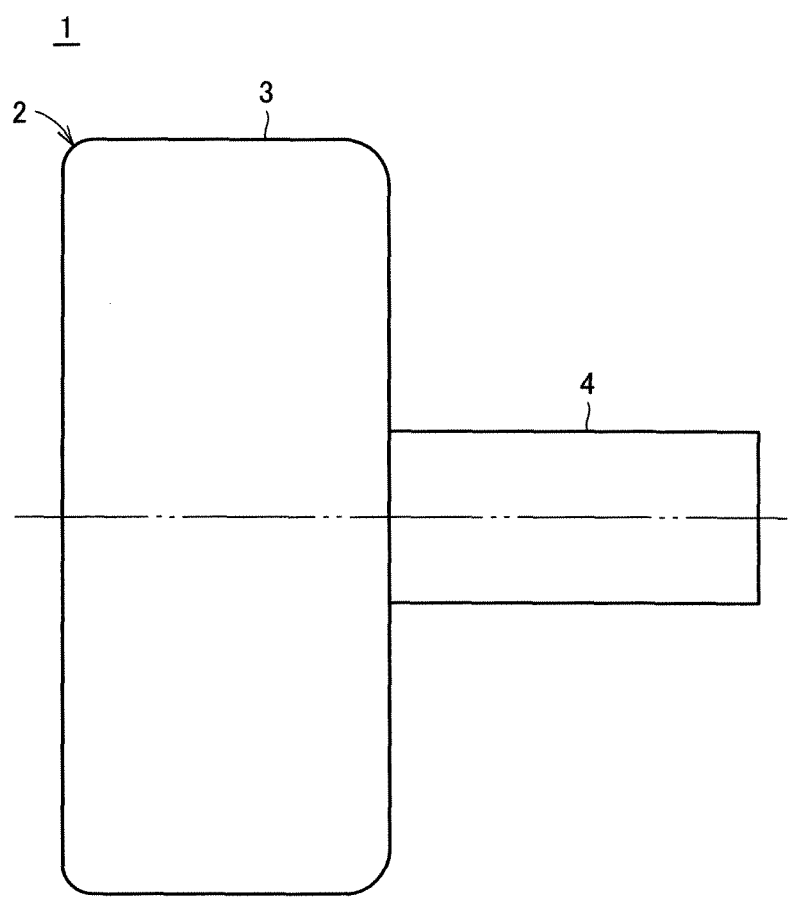
FIG. 1 is a front view showing the appearance of a pump unit of a centrifugal blood pump apparatus according to a first embodiment of the present invention.
Figure 2:
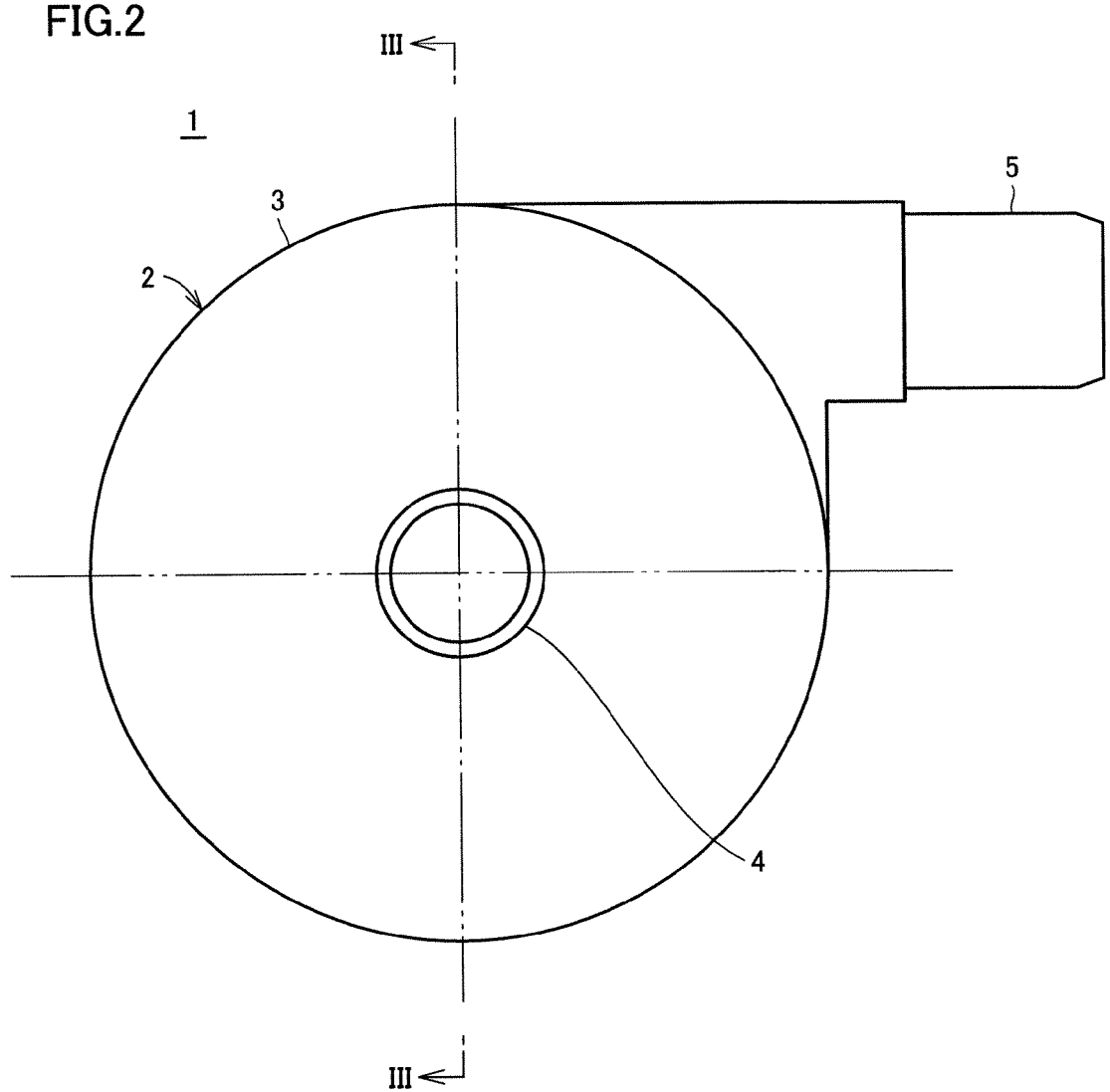
FIG. 2 is a side view of the pump unit shown in FIG. 1.
Figure 3:
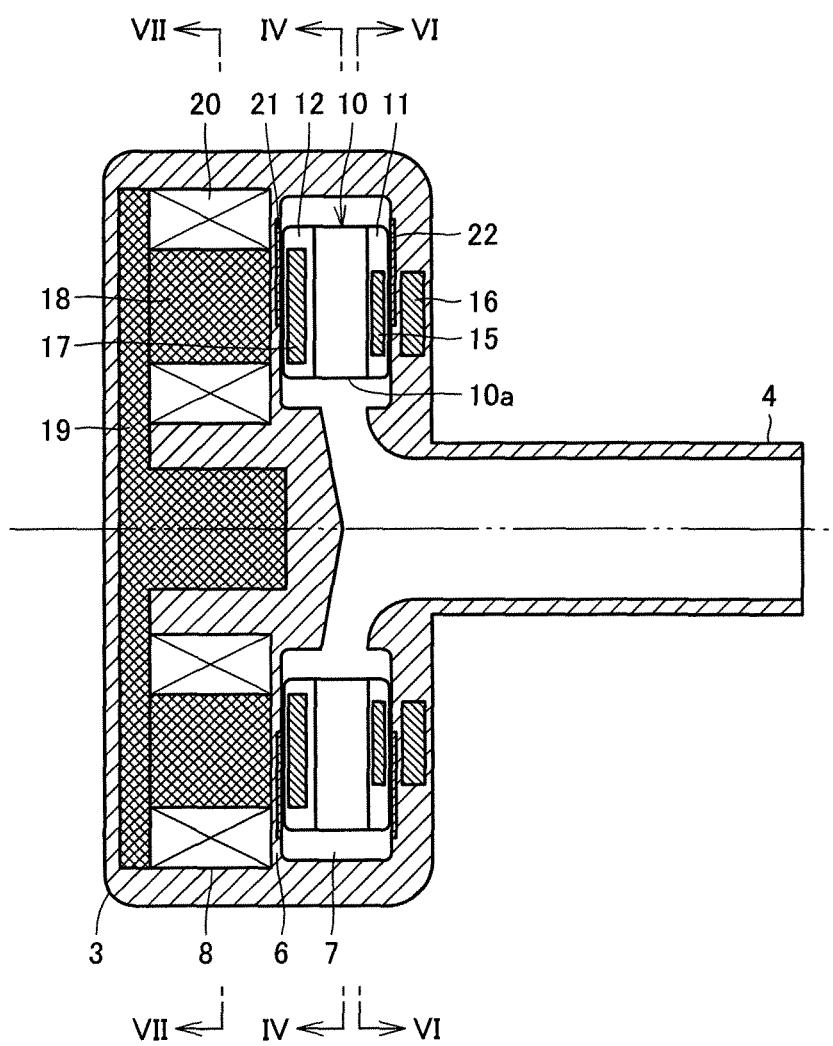
FIG. 3 is a cross-sectional view along the line in FIG. 2.
Figure 4:
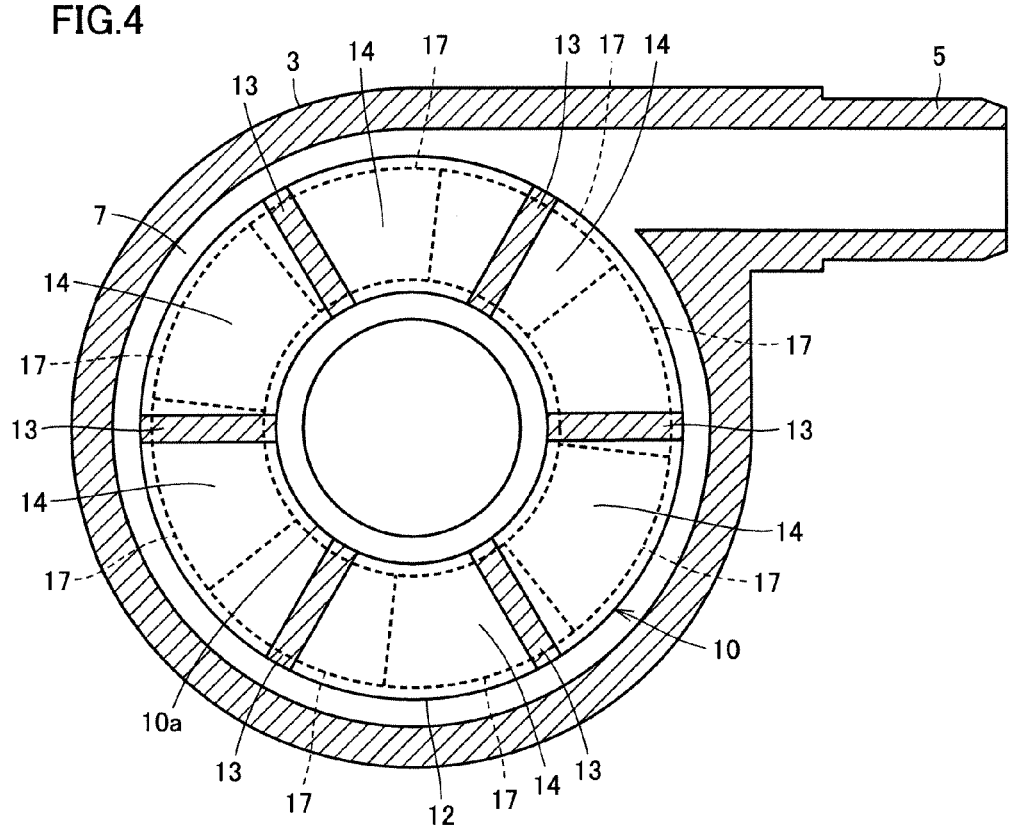
FIG. 4 is a cross-sectional view along the line IV-IV in FIG. 3.
Figure 5:
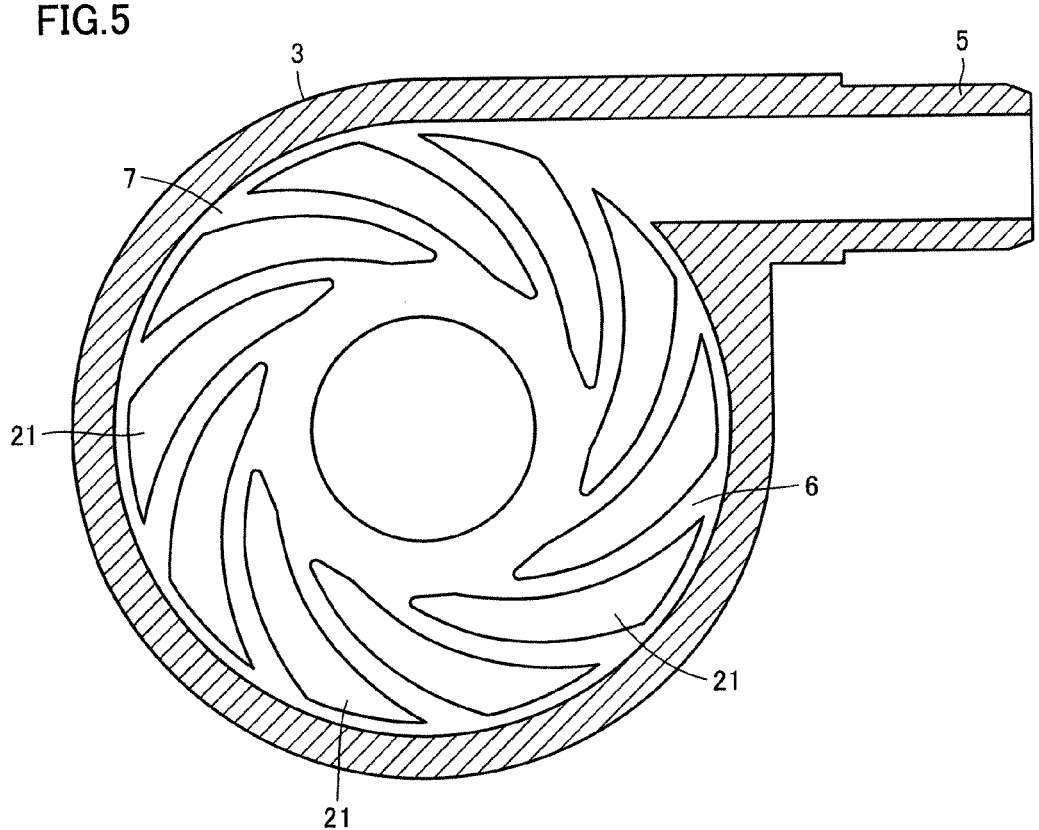
FIG. 5 is a cross-sectional view showing a state where an impeller has been removed from the cross-sectional view along the line IV-IV in FIG. 3.
Figure 6:
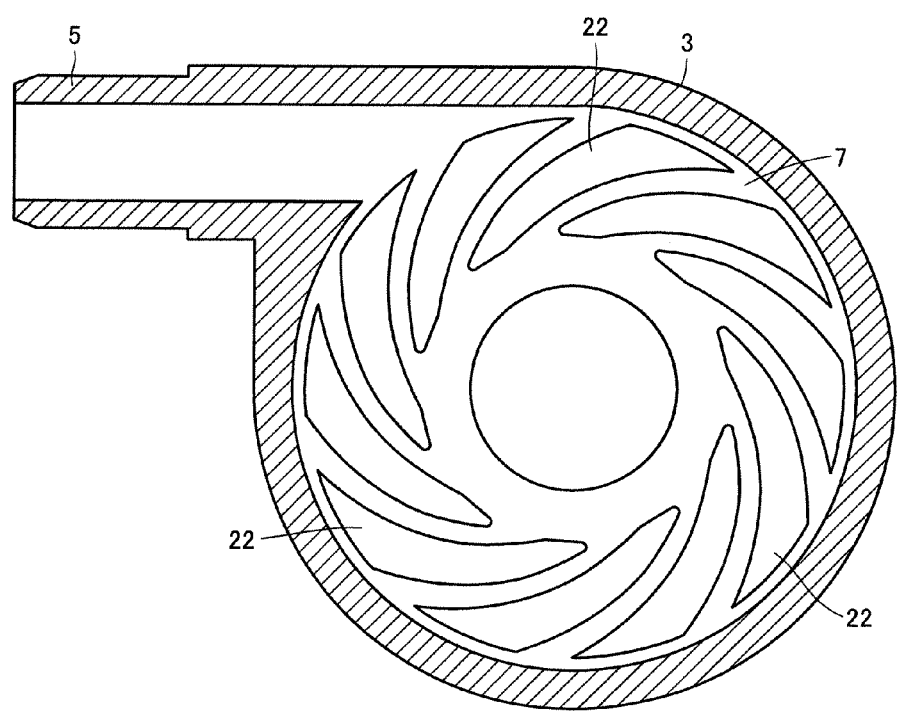
FIG. 6 is a cross-sectional view showing the state where the impeller has been removed from a cross-sectional view along the line VI-VI in FIG. 3.
Figure 7:
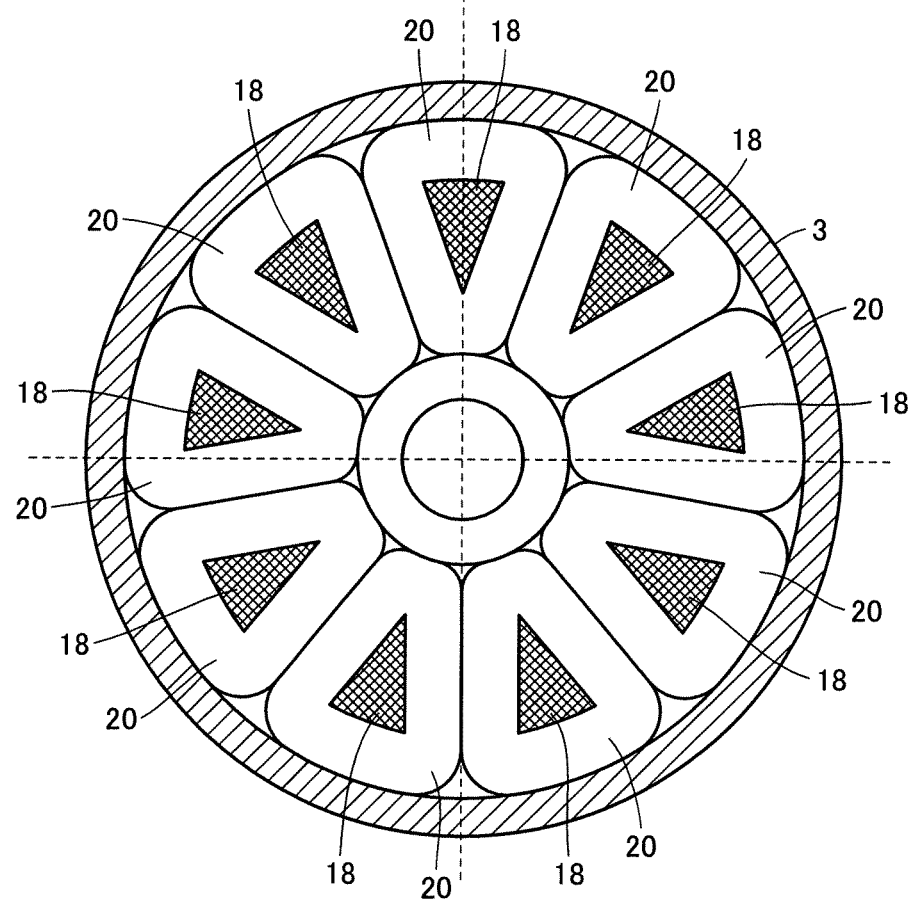
FIG. 7 is a cross-sectional view along the line VII-VII in FIG. 3.

FIG. 1 is a front view showing the appearance of a pump unit 1 of a centrifugal blood pump apparatus according to a first embodiment of the present invention, and FIG. 2 is a side view thereof. FIG. 3 is a cross-sectional view along the line in FIG. 2, FIG. 4 is a cross-sectional view along the line IV-IV in FIG. 3, and FIG. 5 is a cross-sectional view showing a state where an impeller has been removed from the cross-sectional view along the line IV-IV in FIG. 3. FIG. 6 is a cross-sectional view showing the state where the impeller has been removed from a cross-sectional view along the line VI-VI in FIG. 3, and FIG. 7 is a cross-sectional view along the line VII-VII in FIG. 3.

In FIGS. 1 to 7, pump unit 1 of this centrifugal blood pump apparatus includes a housing 2 made of a nonmagnetic material. Housing 2 includes a cylindrical body portion 3, a cylindrical blood inlet port 4 provided to stand at a center of one end surface of body portion 3, and a cylindrical blood outlet port 5 provided on an outer circumferential surface of body portion 3. Blood outlet port 5 extends in a tangential direction of the outer circumferential surface of body portion 3.

In housing 2, as shown in FIG. 3, a blood chamber 7 and a motor chamber 8 partitioned from each other by a diaphragm 6 are provided. In blood chamber 7, as shown in FIGS. 3 and 4, a disc-shaped impeller 10 having a through hole 10a in a center thereof is rotatably provided. Impeller 10 includes two shrouds 11, 12 in a doughnut plate shape, and a plurality of (e.g., six) vanes 13 formed between two shrouds 11 and 12. Shroud 11 is arranged on the blood inlet port 4 side, and shroud 12 is arranged on the diaphragm 6 side. Shrouds 11, 12 and vanes 13 are made of a nonmagnetic material.

A plurality of (six in this case) blood passages 14 partitioned from one another by the plurality of vanes 13 are formed between two shrouds 11 and 12. As shown in FIG. 4, blood passage 14 is in communication with through hole 10a in the center of impeller 10, and extends with through hole 10a in impeller 10 as a starting point to an outer circumference such that blood passage 14 gradually increases in width. In other words, vane 13 is formed between two adjacent blood passages 14. In the first embodiment, the plurality of vanes 13 are formed at equiangular intervals, and have the same shape. Thus, the plurality of blood passages 14 are provided at equiangular intervals, and have the same shape.

When impeller 10 is driven to rotate, blood that has flowed in through blood inlet port 4 is delivered by centrifugal force from through hole 10a to an outer circumferential portion of impeller 10 via blood passages 14, and flows out through blood outlet port 5.

A permanent magnet 15 is embedded in shroud 11, and a permanent magnet 16 for attracting permanent magnet 15 is embedded in an inner wall of blood chamber 7 facing shroud 11. Permanent magnets 15 and 16 are provided to attract (in other words, bias) impeller 10 to the side opposite to motor chamber 8, namely, toward blood inlet port 4.

Instead of providing permanent magnets 15 and 16 in shroud 11 and the inner wall of blood chamber 7, respectively, a permanent magnet may be provided in one of shroud 11 and the inner wall of blood chamber 7, and a magnetic material may be provided in the other. Alternatively, shroud 11 itself may be formed of permanent magnet 15 or a magnetic material. Either a soft magnetic material or a hard magnetic material may be used as the magnetic material.

Permanent magnet 16 may be a single magnet, or a plurality of magnets. If it is a single magnet, permanent magnet 16 is formed in a ring shape. If it is a plurality of magnets, permanent magnets 16 are arranged at equiangular intervals along a single circle. As with permanent magnet 16, permanent magnet 15 may also be a single magnet, or a plurality of magnets.

As shown in FIG. 4, a plurality of (e.g., eight) permanent magnets 17 are embedded in shroud 12. The plurality of permanent magnets 17 are arranged at equiangular intervals along a single circle such that adjacent magnetic polarities thereof are different from each other. In other words, permanent magnet 17 having the N-pole toward motor chamber 8 and permanent magnet 17 having the S-pole toward motor chamber 8 are alternately arranged at equiangular intervals along a single circle.

As shown in FIG. 7, a plurality of (e.g., nine) magnetic materials 18 are provided in motor chamber 8. The plurality of magnetic materials 18 are arranged at equiangular intervals along a single circle to face the plurality of permanent magnets 17 in impeller 10. A base end of each of the plurality of magnetic materials 18 is joined to one disc-shaped yoke 19. A coil 20 is wound around each magnetic material 18.

Each of the plurality of magnetic materials 18 is formed in a shape of a triangular prism of the same dimensions. In addition, space for winding coil 20 is equally secured around the plurality of magnetic materials 18, and surfaces facing each other of every two adjacent magnetic materials 18 are provided substantially parallel to each other. Thus, large space for coils 20 can be secured, to increase turns of coils 20. As a result, large torque for driving impeller 10 to rotate can be generated. Further, copper loss that occurs in coils 20 can be reduced, thereby increasing energy efficiency when driving impeller 10 to rotate.

An outline surface surrounding the plurality of magnetic materials 18 (a circle surrounding the peripheries of the plurality of magnetic materials 18 in FIG. 7) may correspond to an outline surface surrounding the plurality of permanent magnets 17 (a circle surrounding the peripheries of the plurality of magnetic materials 17 in FIG. 4), or the outline surface surrounding the plurality of magnetic materials 18 may be larger than the outline surface surrounding the plurality of permanent magnets 17. Further, it is preferable that magnetic material 18 be designed not to be magnetically saturated at maximum rating of pump 1 (a condition where torque for driving impeller 10 to rotate becomes maximum).

Figure 8:
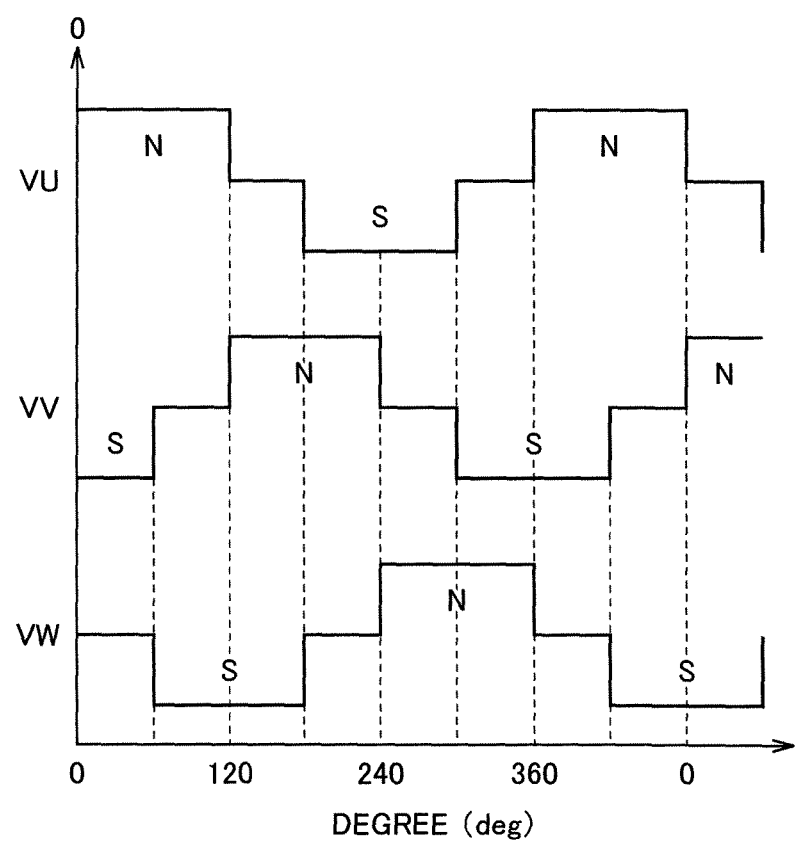
FIG. 8 is a time chart illustrating voltages applied to a plurality of coils shown in FIG. 7.

Voltages are applied to nine coils 20 in a power distribution system shifted by 120 degrees, for example. That is, nine coils 20 are divided into groups each including three coils. Voltages VU, VV and VW as shown in FIG. 8 are applied to first to third coils 20 of each group, respectively. To first coil 20, a positive voltage is applied during a period of 0 to 120 degrees, 0 V is applied during a period of 120 to 180 degrees, a negative voltage is applied during a period of 180 to 300 degrees, and 0 V is applied during a period of 300 to 360 degrees. Accordingly, a tip surface of magnetic material 18 having first coil 20 wound therearound (end surface on the impeller 10 side) becomes the N-pole during the period of 0 to 120 degrees, and becomes the S-pole during the period of 180 to 300 degrees. Voltage VV is delayed in phase from voltage VU by 120 degrees, and voltage VW is delayed in phase from voltage VV by 120 degrees. Thus, a rotating magnetic field can be generated by applying voltages VU, VV and VW to first to third coils 20, respectively, and impeller 10 can be rotated by attractive force and repulsion force between the plurality of magnetic materials 18 and the plurality of permanent magnets 17 in impeller 10.

When impeller 10 is rotating with a rated rotation speed, the attractive force between permanent magnets 15 and 16, and the attractive force between the plurality of permanent magnets 17 and the plurality of magnetic materials 18 are set to be balanced with each other substantially in a center of a movable range of impeller 10 in blood chamber 7. Thus, acting force due to the attractive force on impeller 10 is very small throughout the movable range of impeller 10. Consequently, frictional resistance during relative slide between impeller 10 and housing 2 which occurs when impeller 10 is activated to rotate can be reduced. In addition, a surface of impeller 10 and a surface of an inner wall of housing 2 are not damaged (no projections and depressions in the surfaces) during the relative slide, and moreover, impeller 10 is readily levitated from housing 2 without contacting even when hydrodynamic pressure is small during low-speed rotation. Accordingly, occurrence of hemolysis/thrombus due to the relative slide between impeller 10 and housing 2, or occurrence of thrombus due to small damage (projections and depressions) to the surfaces which occurs during the relative slide can be avoided.

A plurality of grooves for hydrodynamic bearing 21 are formed in a surface of diaphragm 6 facing shroud 12 of impeller 10, and a plurality of grooves for hydrodynamic bearing 22 are formed in the inner wall of blood chamber 7 facing shroud 11. When a rotation speed of impeller 10 becomes higher than a predetermined rotation speed, a hydrodynamic bearing effect is produced between grooves for hydrodynamic bearing 21, 22 and impeller 10, respectively. As a result, drag is generated on impeller 10 from grooves for hydrodynamic bearing 21 and 22, causing impeller 10 to rotate without contacting in blood chamber 7.

Specifically, as shown in FIG. 5, the plurality of grooves for hydrodynamic bearing 21 are formed with a size corresponding to shroud 12 of impeller 10. Each of grooves for hydrodynamic bearing 21 has one end on an edge (circumference) of a circular portion slightly distant from a center of diaphragm 6, and extends spirally (in other words, in a curved manner) to a portion near an outer edge of diaphragm 6 such that grooves for hydrodynamic bearing 21 gradually increases in width. The plurality of grooves for hydrodynamic bearing 21 have substantially the same shape, and are arranged at substantially the same intervals. Grooves for hydrodynamic bearing 21 is a concave portion, and preferably has a depth of about 0.005 to 0.4 mm. It is preferable that about 6 to 36 grooves for hydrodynamic bearing 21 be provided.

In FIG. 5, ten grooves for hydrodynamic bearing 21 are equiangularly arranged with respect to a central axis of impeller 10. Since grooves for hydrodynamic bearing 21 have a so-called inward spiral groove shape, clockwise rotation of impeller 10 causes increase in liquid pressure from an outer diameter portion toward an inner diameter portion of grooves for hydrodynamic bearing 21. As a result, repulsion force is generated between impeller 10 and diaphragm 6, and acts as hydrodynamic pressure.

Instead of providing grooves for hydrodynamic bearing 21 in diaphragm 6, grooves for hydrodynamic bearing 21 may be provided in a surface of shroud 12 of impeller 10.

In this manner, owing to the hydrodynamic bearing effect produced between impeller 10 and the plurality of grooves for hydrodynamic bearing 21, impeller 10 moves away from diaphragm 6, and rotates without contacting. Accordingly, a blood flow path is secured between impeller 10 and diaphragm 6, thus preventing occurrence of blood accumulation therebetween and the resultant thrombus. Further, in a normal state, grooves for hydrodynamic bearing 21 exercise a stirring effect between impeller 10 and diaphragm 6, thus preventing occurrence of partial blood accumulation therebetween.

It is preferable that a corner portion of grooves for hydrodynamic bearing 21 be rounded to have R of at least equal to higher than 0.05 mm. As a result, occurrence of hemolysis can be further reduced.

As with the plurality of grooves for hydrodynamic bearing 21, as shown in FIG. 6, the plurality of grooves for hydrodynamic bearing 22 are formed with a size corresponding to shroud 11 of impeller 10. Each of grooves for hydrodynamic bearing 22 has one end on an edge (circumference) of a circular portion slightly distant from a center of the inner wall of blood chamber 7, and extends spirally (in other words, in a curved manner) to a portion near an outer edge of the inner wall of blood chamber 7 such that grooves for hydrodynamic bearing 22 gradually increases in width. The plurality of grooves for hydrodynamic bearing 22 have substantially the same shape, and are arranged at substantially the same intervals. Grooves for hydrodynamic bearing 22 is a concave portion, and preferably has a depth of about 0.005 to 0.4 mm. It is preferable that about 6 to 36 grooves for hydrodynamic bearing 22 be provided. In FIG. 6, ten grooves for hydrodynamic bearing 22 are equiangularly arranged with respect to the central axis of impeller 10.

Grooves for hydrodynamic bearing 22 may be provided in a surface of shroud 11 of impeller 10, rather than on the inner surface side of blood chamber 7. It is preferable that a corner portion of grooves for hydrodynamic bearing 22 be rounded to have R of at least equal to or higher than 0.05 mm. As a result, occurrence of hemolysis can be further reduced.

In this manner, owing to the hydrodynamic bearing effect produced between impeller 10 and the plurality of grooves for hydrodynamic bearing 22, impeller 10 moves away from the inner wall of blood chamber 7, and rotates without contacting. In addition, when pump unit 1 is subject to external impact, or when the hydrodynamic pressure by grooves for hydrodynamic bearing 21 becomes excessive, impeller 10 can be prevented from being in close contact with the inner wall of blood chamber 7. The hydrodynamic pressure generated by grooves for hydrodynamic bearing 21 may be different from the hydrodynamic pressure generated by grooves for hydrodynamic bearing 22.

It is preferable that impeller 10 rotate in a state where a gap between shroud 12 of impeller 10 and diaphragm 6 is substantially equal to a gap between shroud 11 of impeller 10 and the inner wall of blood chamber 7. If one of the gaps becomes narrower due to serious disturbance such as hydrodynamic force acting on impeller 10, it is preferable that grooves for hydrodynamic bearing 21 and 22 have different shapes, so that the hydrodynamic pressure by the grooves for hydrodynamic bearing on the narrower side becomes higher than the hydrodynamic pressure by the other grooves for hydrodynamic bearing to make the gaps substantially equal to each other.

While both of grooves for hydrodynamic bearing 21 and 22 have the inward spiral groove shape in FIGS. 5 and 6, grooves for hydrodynamic bearing 21 and 22 having another shape may be used. Nevertheless, for blood circulation, it is preferable to employ grooves for hydrodynamic bearing 21 and 22 having the inward spiral groove shape that allows a smooth flow of blood.

Figure 9:
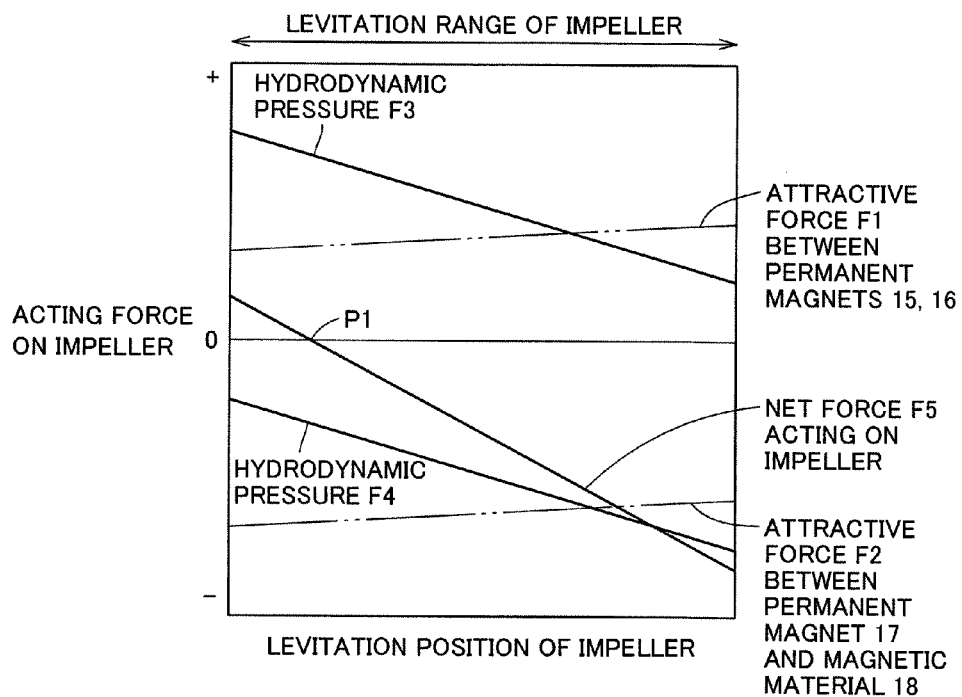
FIG. 9 illustrates an effect of the present invention.

FIG. 9 illustrates forces acting on impeller 10 when magnitude of a resultant force of an attractive force F1 between permanent magnets 15 and 16 and an attractive force F2 between permanent magnet 17 and magnetic material 18 is adjusted to be zero in a position P1 other than a central position of the movable range of impeller 10 in blood chamber 7. The rotation speed of impeller 10 is kept at a rated value.

That is, a levitation position of impeller 10 when attractive force F1 between permanent magnets 15 and 16 is set to be smaller than attractive force F2 between permanent magnet 17 and magnetic material 18 and their resultant force becomes zero is on the diaphragm 6 side relative to the center of the movable range of the impeller. Grooves for hydrodynamic bearing 21 and 22 have the same shape.

A horizontal axis of FIG. 9 represents a position of impeller 10 (the left side in the figure being the diaphragm 6 side), and a vertical axis represents acting forces on impeller 10. An acting force on impeller 10 toward the diaphragm 6 side is expressed as a negative acting force. As the acting forces on impeller 10, attractive force F1 between permanent magnets 15 and 16, attractive force F2 between permanent magnet 17 and magnetic material 18, a hydrodynamic pressure F3 by grooves for hydrodynamic bearing 21, a hydrodynamic pressure F4 by grooves for hydrodynamic bearing 22, and a "net force F5 acting on impeller" which is their resultant force are illustrated.

As can be seen from FIG. 9, in a position where net force F5 acting on impeller 10 becomes zero, the levitation position of impeller 10 is significantly deviated from the central position of the movable range of impeller 10. As a result, a distance between rotating impeller 10 and diaphragm 6 becomes narrower, and impeller 10 is brought into contact with diaphragm 6 even by the action of a small disturbance force on impeller 10.

Figure 10:
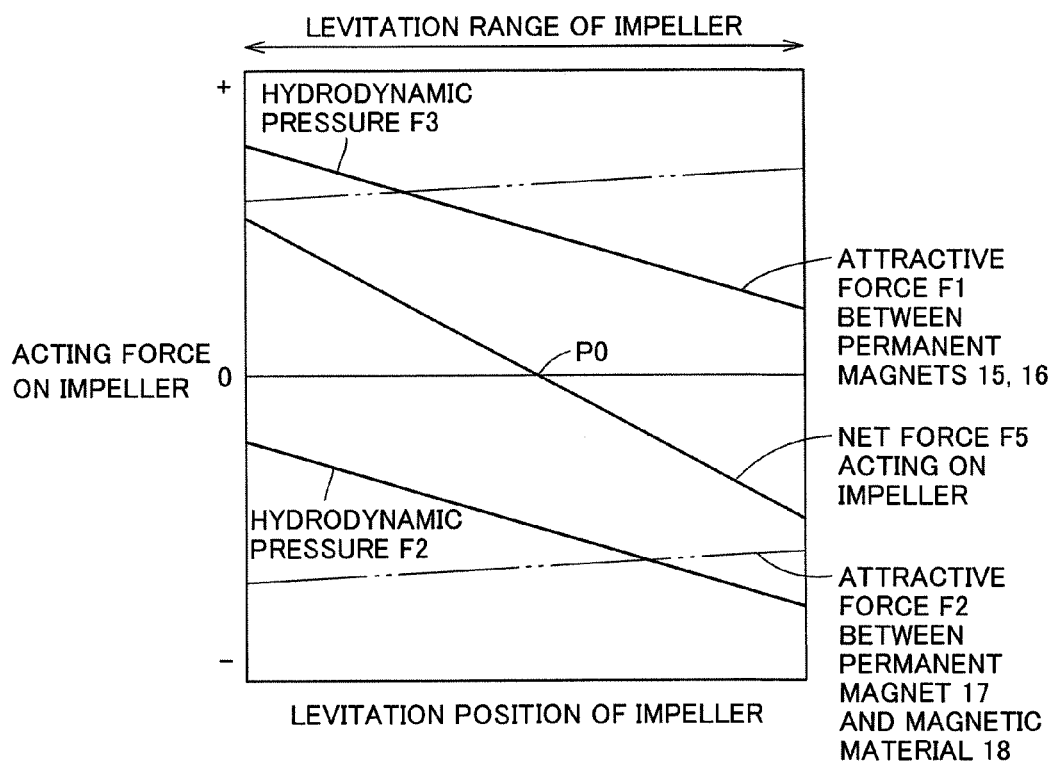
FIG. 10 illustrates the effect of the present invention.

In contrast, FIG. 10 illustrates forces acting on impeller 10 when the magnitude of the resultant force of attractive force F1 between permanent magnets 15 and 16 and attractive force F2 between permanent magnet 17 and magnetic material 18 is adjusted to be zero in a central position P0 of the movable range of impeller 10 in blood chamber 7. The rotation speed of impeller 10 is kept at the rated value in this case as well.

That is, attractive force F1 between permanent magnets 15 and 16 and attractive force F2 between permanent magnet 17 and magnetic material 18 are set to be substantially equal to each other. In addition, grooves for hydrodynamic bearing 21 and 22 have the same shape. In this case, supporting rigidity for the levitation position of impeller 10 is high as compared to the example shown in FIG. 9. Further, since net force F5 acting on impeller 10 is zero in the center of the movable range, impeller 10 is levitated in the central position when a disturbance force is not acting on impeller 10.

As such, a levitation position of impeller 10 is determined by a balance among attractive force F1 between permanent magnets 15 and 16, attractive force F2 between permanent magnet 17 and magnetic material 18, and hydrodynamic pressures F3, F4 generated by grooves for hydrodynamic bearing 21 and 22 during rotation of impeller 10. By making F1 and F2 substantially equal to each other, and by forming grooves for hydrodynamic bearing 21 and 22 in the same shape, impeller 10 can be levitated substantially in a central portion of blood chamber 7 during rotation of impeller 10. Since impeller 10 has a shape in which the vanes are formed between the two discs, as shown in FIGS. 3 and 4, two surfaces facing the inner wall of housing 2 can be formed in the same shape and of the same dimensions. Therefore, it is possible to provide grooves for hydrodynamic bearing 21 and 22 having substantially the same hydrodynamic pressure generating function on both sides of impeller 10.

In this case, impeller 10 is levitated in the central position of blood chamber 7, and thus held in a position farthest from the inner wall of housing 2. As a result, even if the levitation position of impeller 10 is changed due to application of a disturbance force to levitated impeller 10, the possibility that impeller 10 is brought into contact with the inner wall of housing 2 is reduced, thus reducing the possibility of occurrence of thrombus and hemolysis resulting from such contact.

While two grooves for hydrodynamic bearing 21 and 22 have the same shape in the examples shown in FIGS. 9 and 10, grooves for hydrodynamic bearing 21 and 22 may have different shapes and difference hydrodynamic pressure generating functions. For example, when disturbance acts on impeller 10 always in one direction due to hydrodynamic force or the like during pumping, the function of a groove for hydrodynamic bearing in the disturbance direction may be made greater than the function of the other grooves for hydrodynamic bearing, thereby levitating and rotating impeller 10 in the central position of housing 2. As a result, the possibility of contact between impeller 10 and housing 2 can be reduced, thereby attaining stable levitation function of impeller 10.

Furthermore, when an absolute value of a negative axial supporting rigidity value of impeller 10 which is constituted of attractive force F1 between permanent magnets 15 and 16 and attractive force F2 between permanent magnet 17 and magnetic material 18 is expressed as Ka, an absolute value of a positive radial rigidity value is expressed as Kr, and an absolute value of a positive rigidity value obtained by two grooves for hydrodynamic bearing 21 and 22 in a normal rotation speed range where impeller 10 rotates is expressed as Kg, it is preferable that a relation of Kg>Ka+Kr be satisfied.

Specifically, when absolute value Ka of the negative axial rigidity value is 20000 N/m, and absolute value Kr of the positive radial rigidity value is 10000 N/m, absolute value Kg of the positive rigidity value obtained by two grooves for hydrodynamic bearing 21 and 22 in the rotation speed range where impeller 10 normally rotates is set to a value higher than 30000 N/m.

The axial supporting rigidity for impeller 10 is a value obtained by subtracting negative rigidity due to the attractive force between the magnetic materials and the like from rigidity resulting from the hydrodynamic pressures generated by grooves for hydrodynamic bearing 21 and 22. Thus, by satisfying the relation of Kg>Ka+Kr, the axial supporting rigidity for impeller 10 can be made higher than the radial supporting rigidity. With such setting, movement of impeller 10 can be suppressed more in the axial direction than in the radial direction when a disturbance force acts on impeller 10, thereby avoiding mechanical contact between impeller 10 and housing 2 in a portion where grooves for hydrodynamic bearing 21 are formed.

In particular, since grooves for hydrodynamic bearing 21 and 22 are provided as concave portions in the planes as shown in FIGS. 3 and 5, mechanical contact between housing 2 and impeller 10 in these sites during rotation of impeller 10 may result in damage to one or both of a surface of impeller 10 and a surface of the inner wall of housing 2 (projections and depressions in the surfaces), and blood passage through this portion may cause occurrence of thrombus and hemolysis. In order to prevent mechanical contact at grooves for hydrodynamic bearing 21 and 22 to suppress thrombus and hemolysis, it is effective to make the axial rigidity higher than the radial rigidity.

Whirl occurs in unbalanced impeller 10 during rotation, and this whirl is greatest when a natural frequency determined by the mass of impeller 10 and the supporting rigidity value of impeller 10 matches the rotation speed of impeller 10.

Since the radial supporting rigidity for impeller 10 is smaller than the axial supporting rigidity in pump unit 1, it is preferable to set a maximum rotation speed of impeller 10 to be equal to or lower than the radial natural frequency. Accordingly, in order to prevent mechanical contact between impeller 10 and housing 2, when a radial rigidity value of impeller 10 which is constituted of attractive force F1 between permanent magnets 15 and 16 and attractive force F2 between permanent magnet 17 and magnetic material 18 is expressed as Kr (N/m), the mass of impeller 10 is expressed as m (kg), and the rotation speed of the impeller is expressed as ω (rad/s), it is preferable that a relation of a $\omega<(Kr/m)^{0.5}$ be satisfied.

Specifically, when the mass of impeller 10 is 0.03 kg and the radial rigidity value is 2000 N/m, the maximum rotation speed of impeller 10 is set to be equal to or lower than 258 rad/s (2465 rpm). Conversely, when the maximum rotation speed of impeller 10 is set to 366 rad/s (3500 rpm), the radial rigidity is set to be equal to or higher than 4018 N/m.

It is further preferable to set the maximum rotation speed of impeller 10 to be equal to or lower than 80% of this ω. Specifically, when the mass of impeller 10 is 0.03 kg and the radial rigidity value is 2000 N/m, the maximum rotation speed is set to be equal to or lower than 206.4 rad/s (1971 rpm). Conversely, when it is desired to set the maximum rotation speed of impeller 10 to 366 rad/s (3500 rpm), the radial rigidity value is set to be equal to or higher than 6279 N/m. By setting the maximum rotation speed of impeller 10 in this manner, contact between rotating impeller 10 and housing 2 can be suppressed.

When the rigidity due to the hydrodynamic pressures by grooves for hydrodynamic bearing 21 and 22 becomes higher than the negative axial rigidity value of impeller 10 which is constituted of attractive force F1 between permanent magnets 15 and 16 and attractive force F2 between permanent magnet 17 and magnetic material 18, impeller 10 and housing 2 are not in contact with each other. It is thus preferable to minimize this negative rigidity value. In order to keep the negative rigidity value low, it is preferable that the surfaces facing each other of permanent magnets 15 and 16 have different sizes. For example, by making the size of permanent magnet 16 smaller than that of permanent magnet 15, a rate of change in attractive force that varies with a distance between the magnets, namely, the negative rigidity can be minimized, thereby preventing reduction in supporting rigidity for the impeller.

It is also preferable to check to see that impeller 10 is in contact with diaphragm 6 before activating impeller 10 to rotate.

Namely, when impeller 10 is not rotating, impeller 10 is not supported without contacting by grooves for hydrodynamic bearing 21 and 22, but is in contact with housing 2 with a high surface pressure due to attractive force F1 between permanent magnets 15 and 16 and attractive force F2 between permanent magnet 17 and magnetic material 18. Further, when impeller 10 is rotated by magnetic interaction between coil 20 and magnetic material 18 in motor chamber 8 and permanent magnet 7 in impeller 10 as in pump unit 1, starting torque is small as compared to an example where an impeller is driven to rotate through magnetic coupling between permanent magnets as shown in FIG. 3 of Patent Document 2. It is thus difficult to smoothly activate impeller 10 to rotate.

When shroud 12 of impeller 10 is in contact with diaphragm 6, however, permanent magnet 17 in impeller 10 and magnetic material 18 in motor chamber 8 are closer to each other than when shroud 11 of impeller 10 is in contact with the inner wall of blood chamber 7, which allows increase in rotational torque during activation of impeller 10, thereby smoothly activating impeller 10 to rotate.

As described above, however, when impeller 10 is rotating, attractive force F1 between permanent magnets 15 and 16 and attractive force F2 between permanent magnet 17 and magnetic material 18 are set to be balanced with each other when the position of impeller 10 is near the center of the movable range of impeller 10. Thus, impeller 10 is not necessarily in contact with diaphragm 6 when impeller 10 is not rotating.

For this reason, this centrifugal blood pump apparatus is provided with means for moving impeller 10 toward diaphragm 6 before activating impeller 10 to rotate. Specifically, a current is fed through the plurality of coils 20 such that attractive force F2 between permanent magnet 17 and magnetic material 18 becomes higher, to move impeller 10 toward diaphragm 6.

Figure 11:
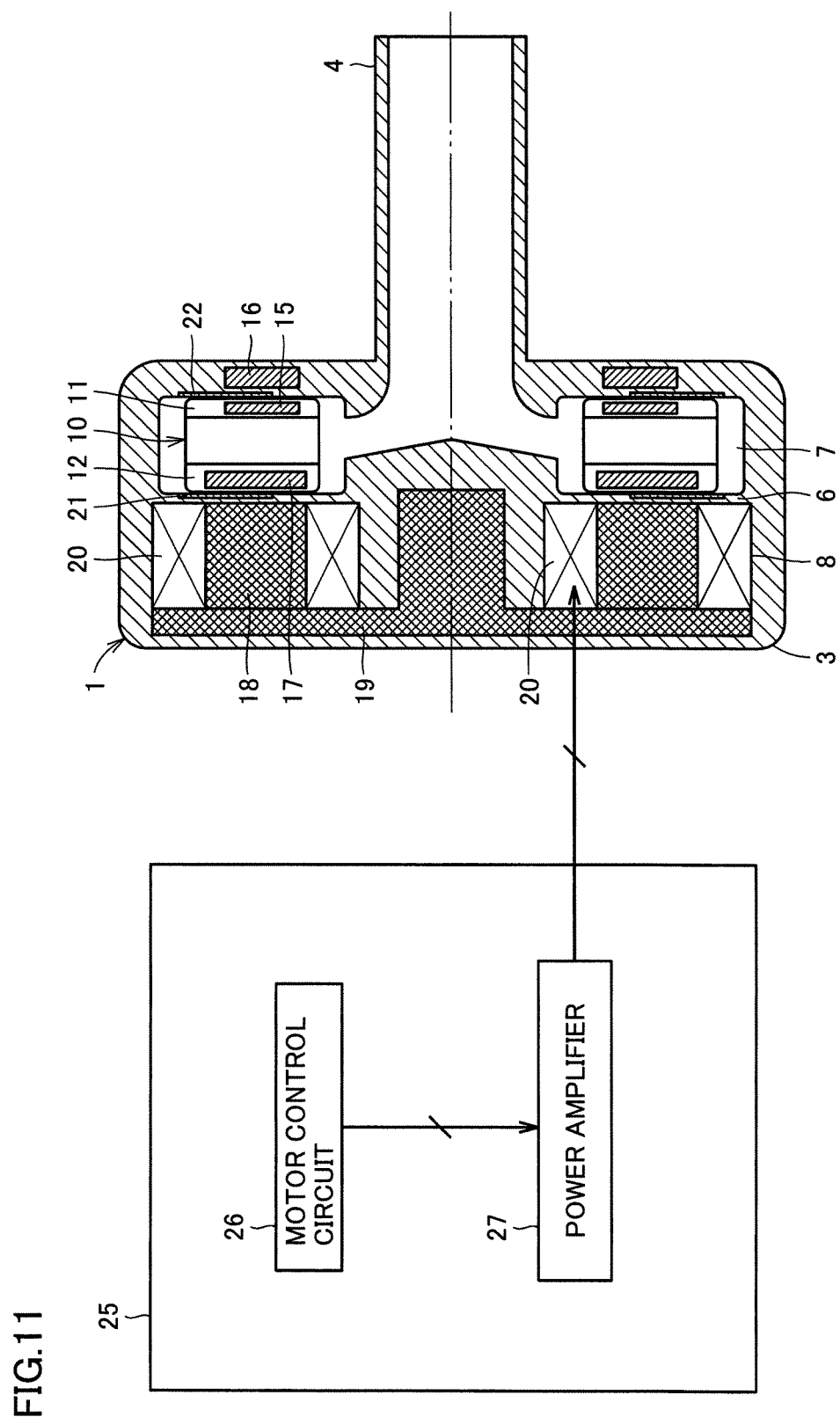
FIG. 11 is a block diagram showing a structure of a controller for controlling the pump unit shown in FIGS. 1 to 7.

FIG. 11 is a block diagram showing a structure of a controller 25 for controlling pump unit 1. In FIG. 11, controller 25 includes a motor control circuit 26 and a power amplifier 27. Motor control circuit 26 outputs three-phase control signals in the power distribution system shifted by 120 degrees, for example. Power amplifier 27 amplifies the three-phase control signals from motor control circuit 26, and generates three-phase voltages VU, VV and VW shown in FIG. 8. Three-phase voltages VU, VV and VW are applied to first to third coils 20 described with reference to FIGS. 7 and 8, respectively. As a result, during normal operation, impeller 10 rotates with a predetermined rotation speed in the central position of the movable range.

Figure 12:
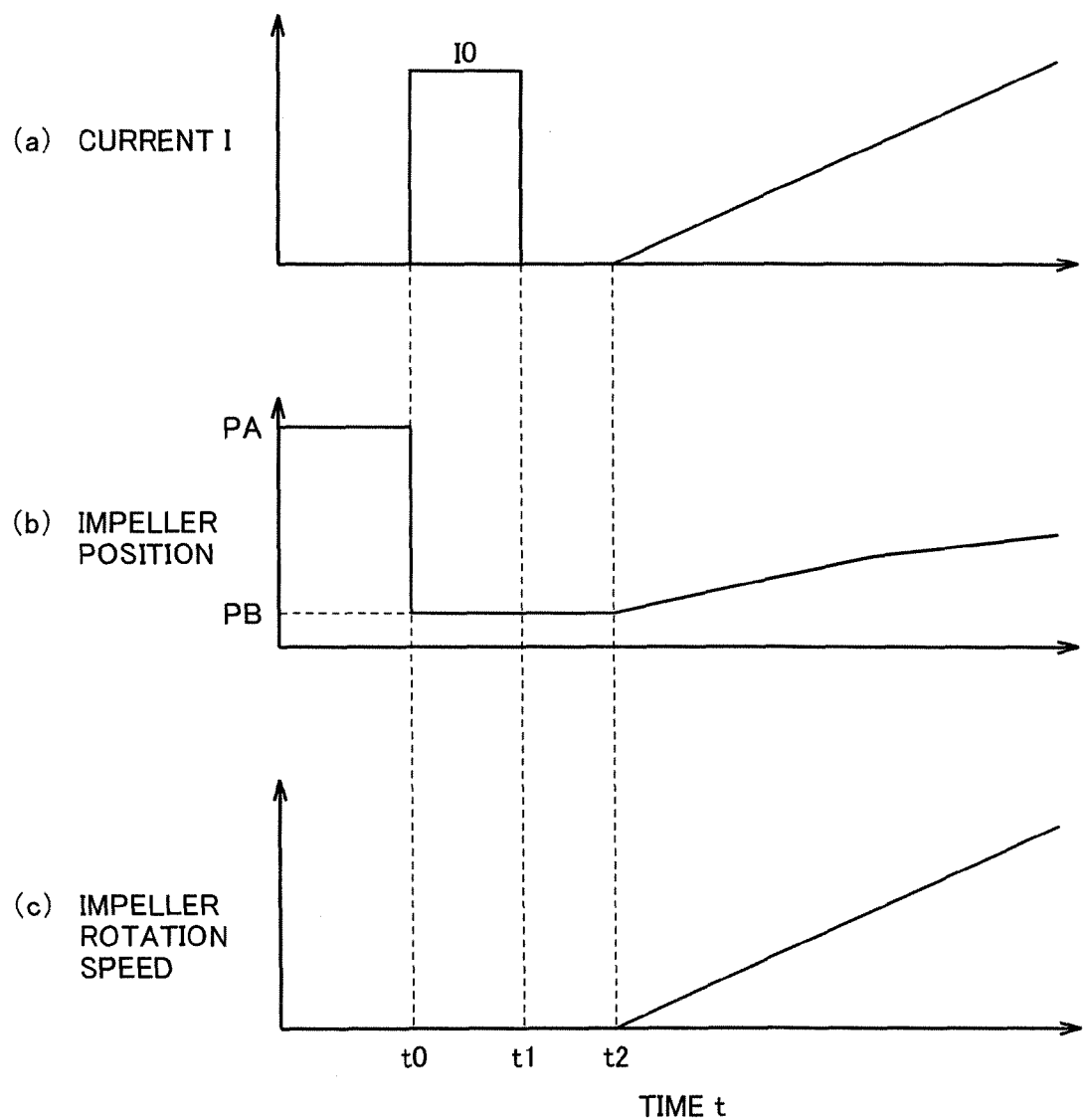
FIG. 12 is a time chart illustrating operation of the controller shown in FIG. 11.

FIG. 12 (a) to (c) are time charts illustrating temporal variations of a coil current I when activating impeller 10 to rotate, the position of impeller 10, and the rotation speed of impeller 10. Referring to FIG. 12 (a) to (c), in an initial state, shroud 11 of impeller 10 is in contact with the inner wall of blood chamber 7 due to the attractive force between permanent magnets 15 and 16, and impeller 10 is in a position PA. Since it is difficult to rotate impeller 10 in this state, impeller 10 is moved to a position PB where shroud 12 of impeller 10 is in contact with diaphragm 6.

At time t0, voltages VU, VV and VW of any one of the six patterns (0 to 60 degrees, 60 to 120 degrees, . . . , 300 to 360 degrees) shown in FIG. 8 are applied to first to third coils 20, respectively, and a predetermined current J0 is fed through coils 20. When current J0 is fed through coils 20, attractive force F2 between permanent magnet 17 and magnetic material 18 becomes higher than attractive force F1 between permanent magnets 15 and 16, so that impeller 10 moves to position PB on the diaphragm 6 side with little rotation, causing shroud 12 of impeller 10 to be in contact with diaphragm 6. When impeller 10 moves to position PB, current J0 is cut off (time t1).

The reason for moving impeller 10 without rotating impeller 10 is that movement of rotating impeller 10 to position PB on the diaphragm 6 side is blocked by the hydrodynamic bearing effect of grooves for hydrodynamic bearing 21. In addition, it is preferable to provide a sensor for detecting a position of impeller 10 in blood chamber 7, and check to see that impeller 10 is in contact with diaphragm 6 before cutting off current I0.

Then, three-phase voltages VU, VV and VW are applied to first to third coils 20 described with reference to FIG. 8, respectively, and coil current I is gradually increased to a predetermined rated value. Here, impeller 10 is in contact with diaphragm 6, and thus smoothly rotates. With the increase in coil current I, impeller 10 moves from position PB on the diaphragm 6 side to the central position of the movable range.

When voltages VU, VV and VW of the six patterns (0 to 60 degrees, 60 to 120 degrees, . . . , 300 to 360 degrees) are applied to first to third coils 20 during activation, respectively, a pattern where the attractive force between permanent magnet 17 and magnetic material 18 becomes maximum varies with positional relation between permanent magnet 17 and magnetic material 18. Thus, instead of applying only voltages VU, VV and VW of the constant patterns to first to third coils 20 during activation, respectively, voltages VU, VV and VW of the six patterns may be successively applied to first to third coils 20 for a predetermined time. In this case, impeller 10 slightly rotates (strictly speaking, equal to or less than a quarter rotation, i.e., rotates equal to or smaller than 360 degrees in electrical angle), and moves to position PB on the diaphragm 6 side.

When voltages VU, VV and VW of the six patterns are applied, a current does not flow through one of first to third coils 20, six of nine magnetic materials 18 become the N-pole or the S-pole, and three remaining magnetic materials 18 do not generate a magnetic polarity. Thus, voltages that cause a current to flow through all of first to third coils 20 and each of nine magnetic materials 18 to become the N-pole or the S-pole may be applied to first to third coils 20, to increase the attractive force between permanent magnet 17 and magnetic material 18.

Figure 13:
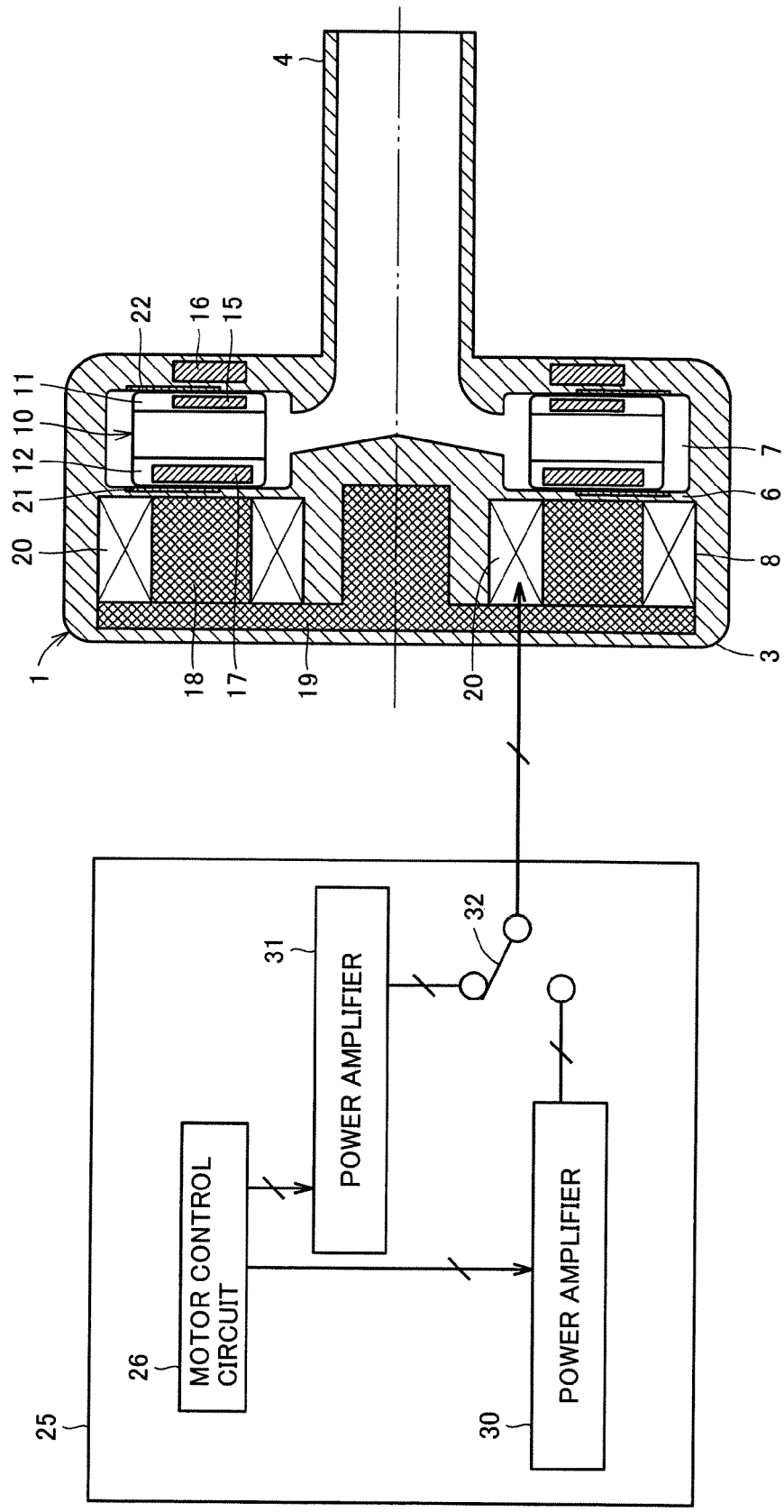
FIG. 13 is a block diagram showing a modification of the first embodiment.

FIG. 13 is a block diagram showing a modification of the first embodiment. In this modification, a power source is switched between during activation of impeller 10 for rotation and a subsequent time period. That is, referring to FIG. 13, in this modification, power amplifier 27 in FIG. 11 is replaced with power amplifiers 30, 31 and a switch 32. Between time t0 and t1 in FIG. 12, an output signal from motor control circuit 26 is provided to power amplifier 30, and an output voltage from power amplifier 30 is applied to coils 20 via switch 32, causing current I0 to flow through coils 20. After time t2, an output signal from motor control circuit 26 is provided to power amplifier 31, and an output voltage from power amplifier 31 is applied to coils 20 via switch 32, causing a current to flow through coils 20.

Figure 14:
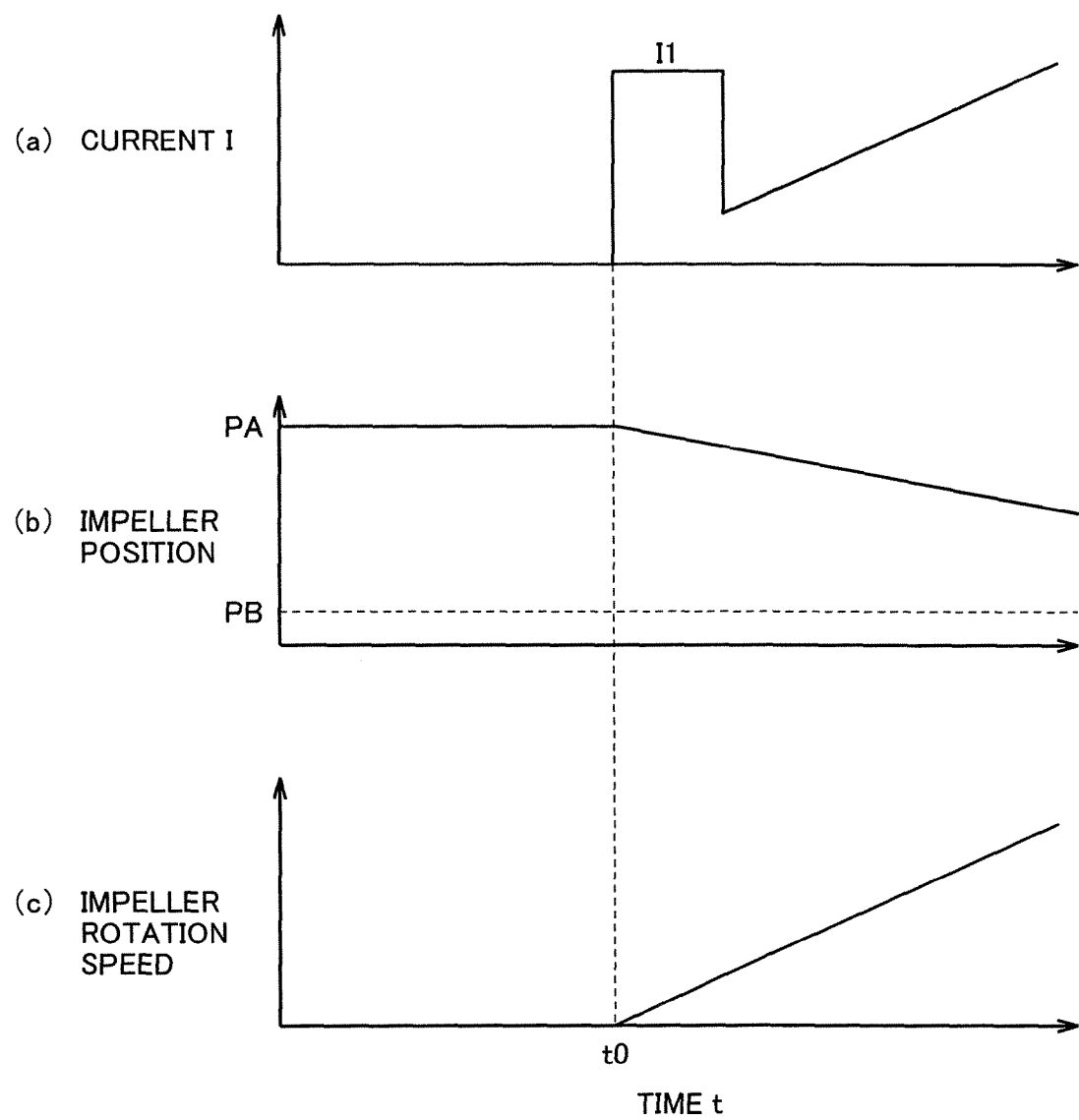
FIG. 14 is a time chart illustrating another modification of the first embodiment.

FIG. 14 (a) to (c) are time charts illustrating another modification of the first embodiment. Referring to FIG. 14 (a) to (c), in an initial state, shroud 11 of impeller 10 is in contact with the inner wall of blood chamber 7, and impeller 10 is in position PA. At time t0, a predetermined current I1 is fed through coils 20. That is, motor control circuit 26 outputs three-phase control signals in the power distribution system shifted by 120 degrees, for example. Power amplifier 27 amplifies the three-phase control signals from motor control circuit 26, and generates three-phase voltages VU, VV and VW shown in FIG. 8. Three-phase voltages VU, VV and VW are applied to first to third coils 20 described with reference to FIGS. 7 and 8, respectively.

Accordingly, a rotating magnetic field is applied to impeller 10 by current I1. Current I1 is larger than current I0 in FIG. 12, and can activate impeller 10 to rotate even when shroud 11 of impeller 10 is in contact with the inner wall of blood chamber 7. After activation for rotation is confirmed, coil current I is reduced, and gradually increased to the predetermined rated value. In this manner, even when impeller 10 is on the position PA side, an overcurrent may be fed through coils 20 only when activating impeller 10 to rotate.

In addition, a diamond-like carbon (DLC) coating may be formed on at least one of the surface of the inner wall of blood chamber 7 and the surface of diaphragm 6, and the surface of impeller 10. As a result, frictional force between impeller 10, and the inner wall of blood chamber 7 and diaphragm 6 can be reduced to smoothly activate the impeller to rotate. A fluorine-based resin coating, a paraxylylene-based resin coating or the like may be formed instead of the diamond-like carbon coating.

Figure 15:
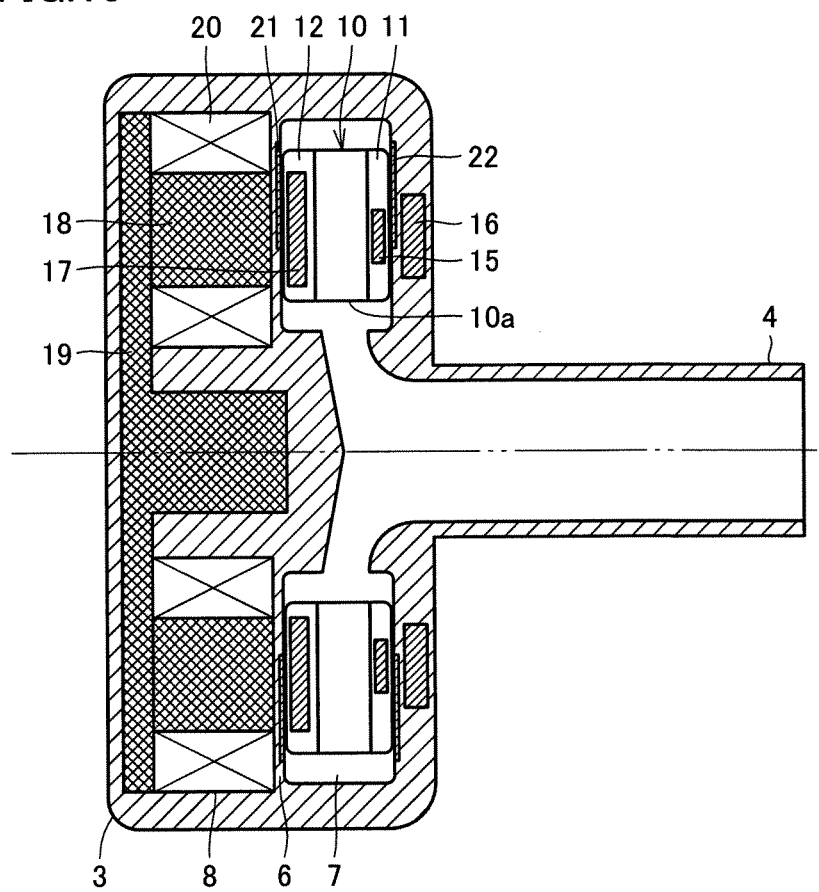
FIG. 15 is a cross-sectional view showing yet another modification of the first embodiment.

FIG. 15 is a cross-sectional view showing yet another modification of the first embodiment, which is compared to FIG. 3. Referring to FIG. 15, in this modification, the surfaces facing each other of permanent magnets 15 and 16 have different sizes. While the surfaces facing each other of permanent magnets 15 and 16 have the same size in FIG. 3, by making the surfaces facing each other of permanent magnets 15 and 16 have different sizes, the amount of change in attractive force which varies with a distance between the magnets, namely, the negative rigidity can be minimized, thereby preventing reduction in supporting rigidity for impeller 10.

Figure 16:
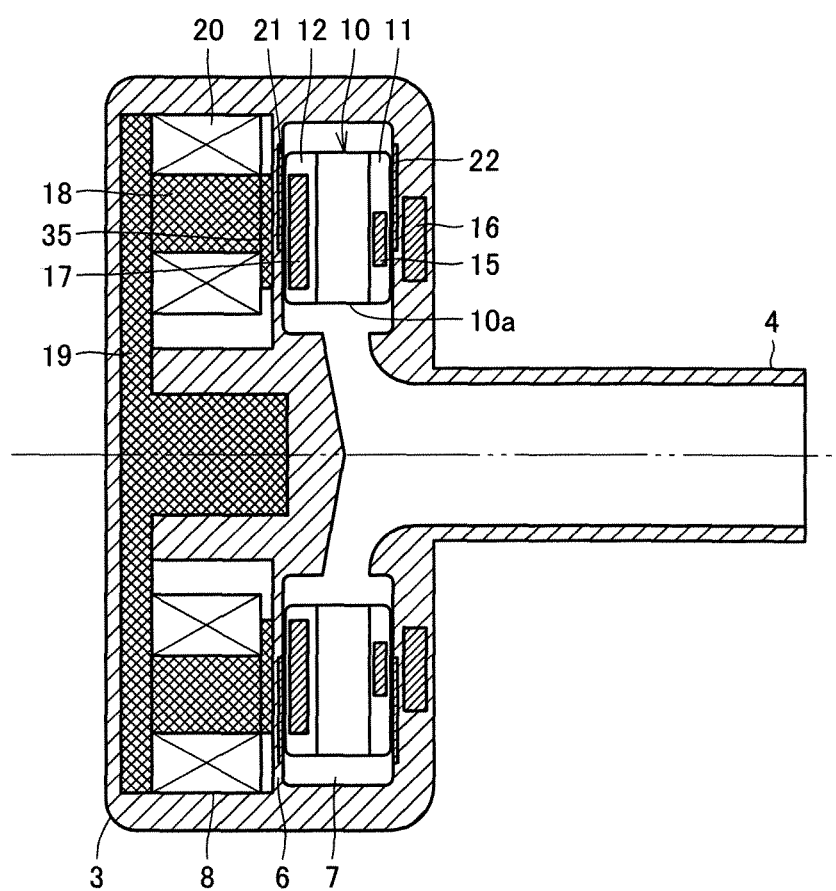
FIG. 16 is a cross-sectional view showing yet another modification of the first embodiment.

FIG. 16 is a cross-sectional view showing yet another modification of the first embodiment, which is compared to FIG. 15. Referring to FIG. 16, in this modification, a magnetic material 35 is provided on a tip surface of each magnetic material 18 facing permanent magnet 17. A surface of magnetic material 35 facing permanent magnet 17 has an area larger than an area of the tip surface of magnetic material 18. In this modification, attractive force of magnetic materials 18 and 35 on permanent magnet 17 can be increased, thus increasing energy efficiency when driving impeller 10 to rotate.

Figure 17:
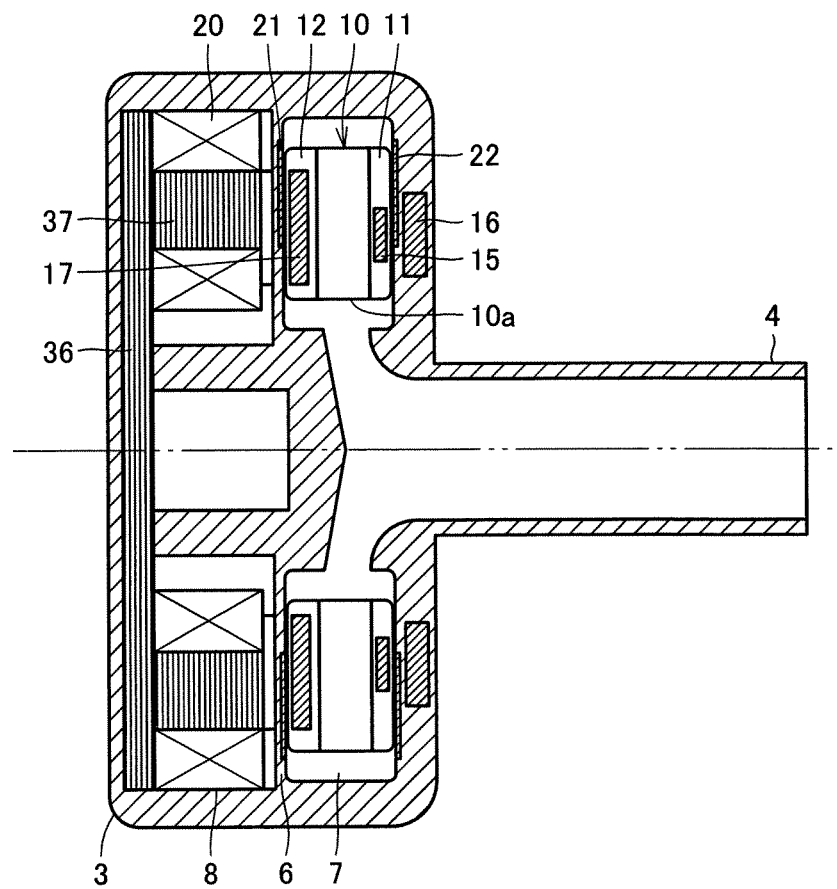
FIG. 17 is a cross-sectional view showing yet another modification of the first embodiment.

FIG. 17 is a cross-sectional view showing yet another modification of the first embodiment, which is compared to FIG. 15. Referring to FIG. 17, in this modification, yoke 19 is replaced with a yoke 36, and magnetic material 18 is replaced with a magnetic material 37. Yoke 36 and magnetic material 37 each include a plurality of steel plates stacked in a length direction of a rotation axis of impeller 10. In this modification, eddy current loss that occurs in yoke 36 and magnetic material 37 can be reduced, thus increasing energy efficiency when driving impeller 10 to rotate.

Figure 18:
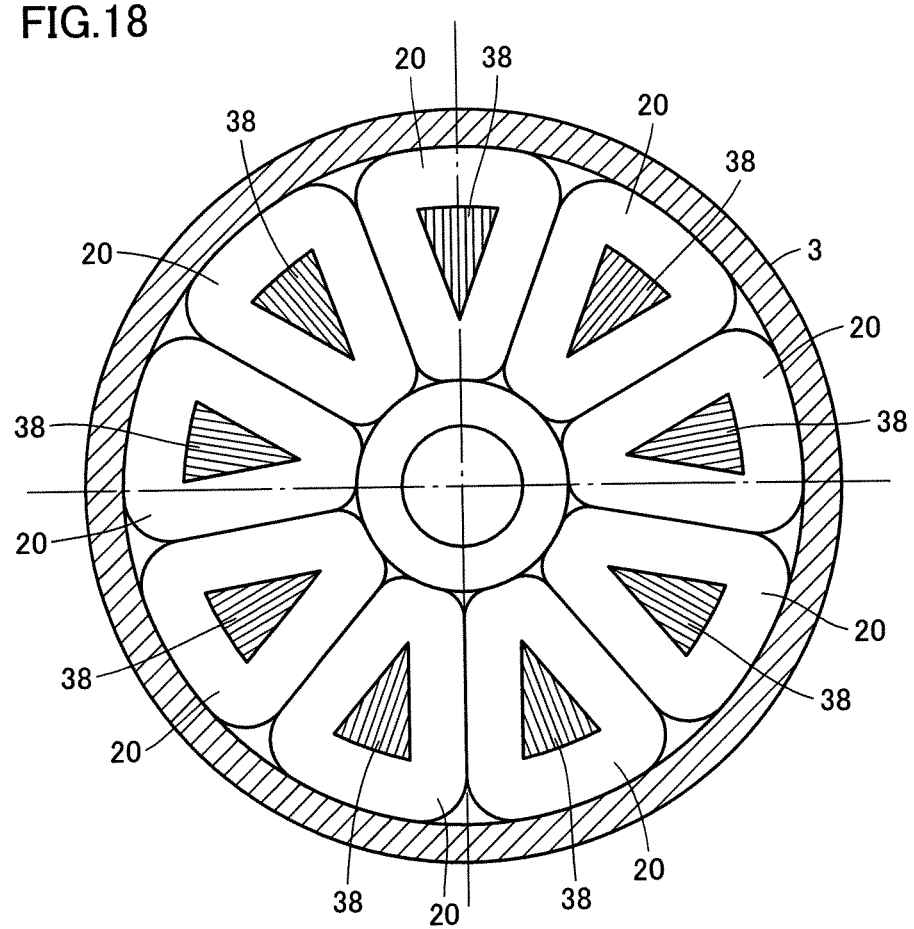
FIG. 18 is a cross-sectional view showing yet another modification of the first embodiment.
Figure 19:
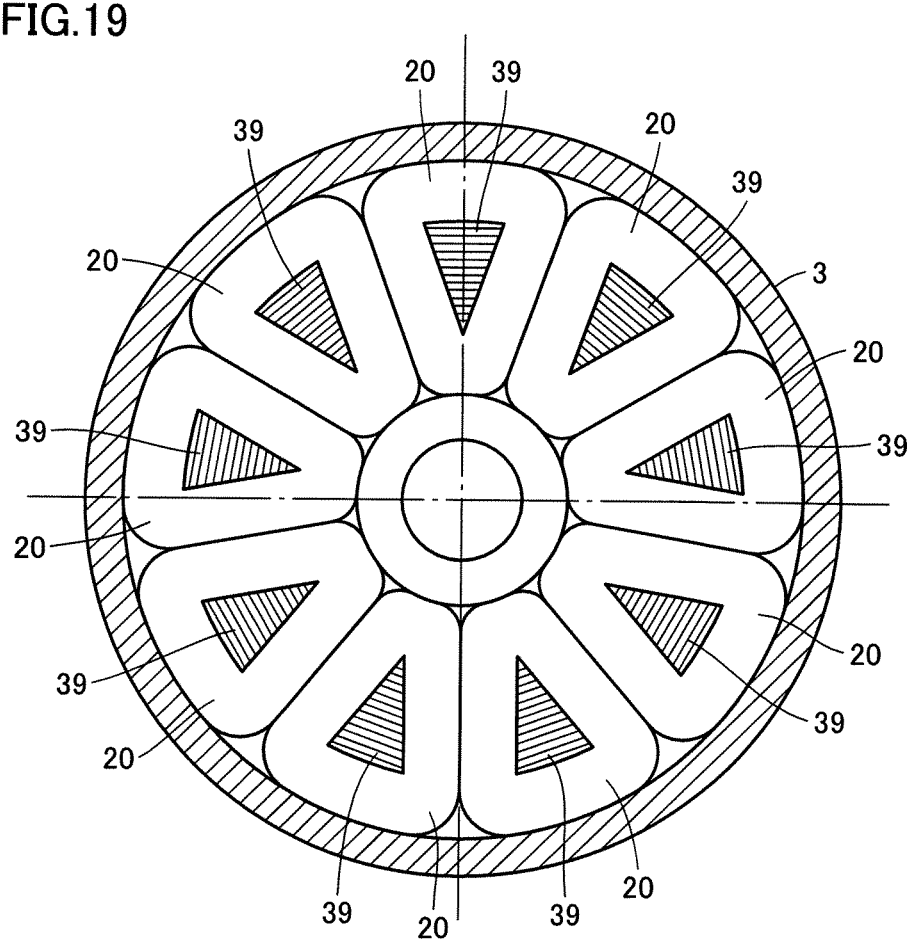
FIG. 19 is a cross-sectional view showing yet another modification of the first embodiment.

Alternatively, as shown in FIG. 18, magnetic material 37 may be replaced with a magnetic material 38 including a plurality of steel plates stacked in a rotation direction of impeller 10. Alternatively, as shown in FIG. 19, magnetic material 37 may be replaced with a magnetic material 39 including a plurality of steel plates stacked in a radial direction of impeller 10. The same effect as in the modification in FIG. 17 can be obtained in these cases as well.

Alternatively, each of yoke 19 and magnetic material 18 in FIG. 3 may be made of powders of pure iron, soft iron, or ferrosilicon. In this case, iron loss in yoke 19 and magnetic material 18 can be reduced, thus increasing energy efficiency when driving impeller 10 to rotate.

Second Embodiment

Figure 20:
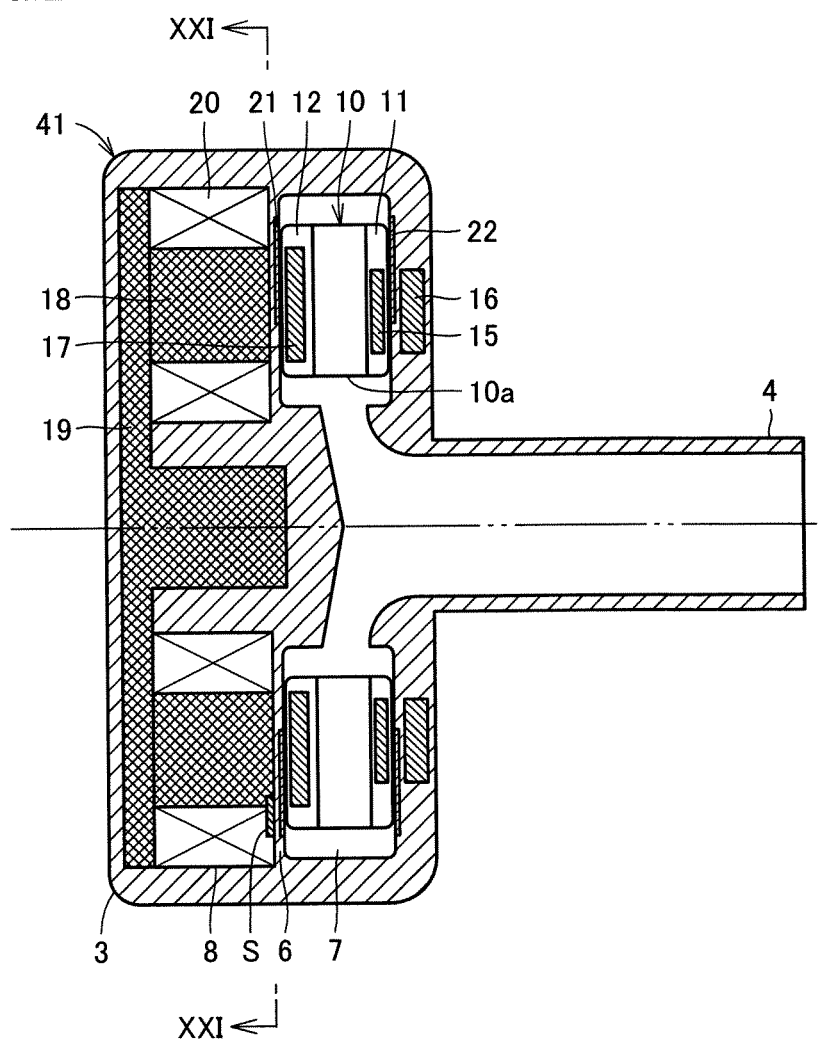
FIG. 20 is a cross-sectional view showing a structure of a pump unit of a centrifugal blood pump apparatus according to a second embodiment of the present invention.
Figure 21:
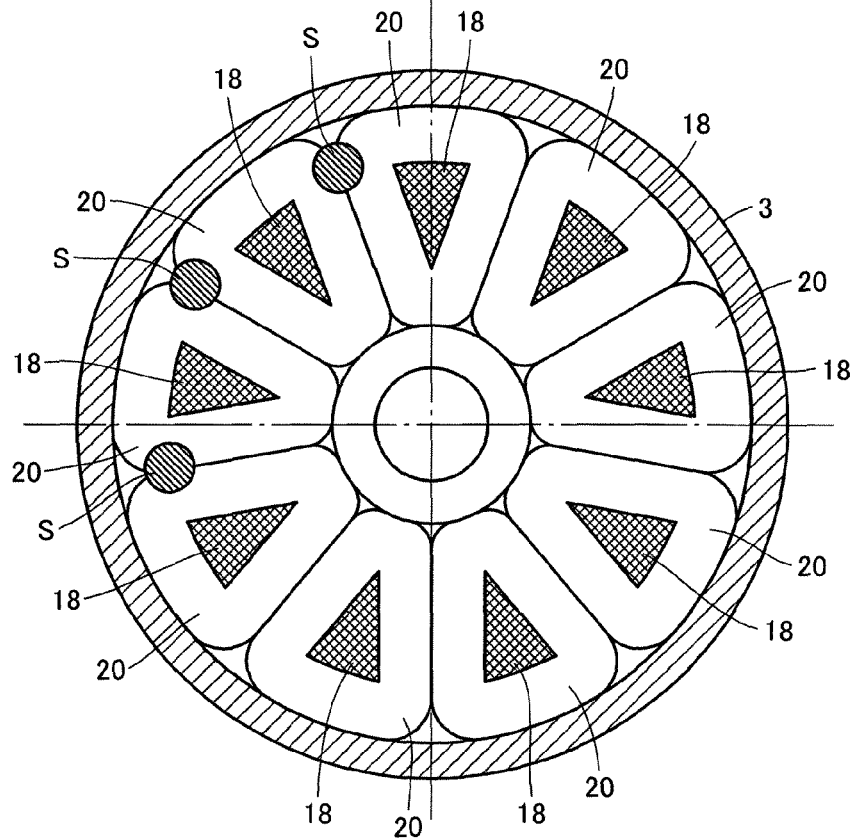
FIG. 21 is a cross-sectional view along the line XXI-XXI in FIG. 20.

FIG. 20 is a cross-sectional view showing a structure of a pump unit 41 of a centrifugal blood pump apparatus according to a second embodiment of the present invention, which is compared to FIG. 3. FIG. 21 is a cross-sectional view along the line XXI-XXI in FIG. 20, which is compared to FIG. 7.

Figure 22:
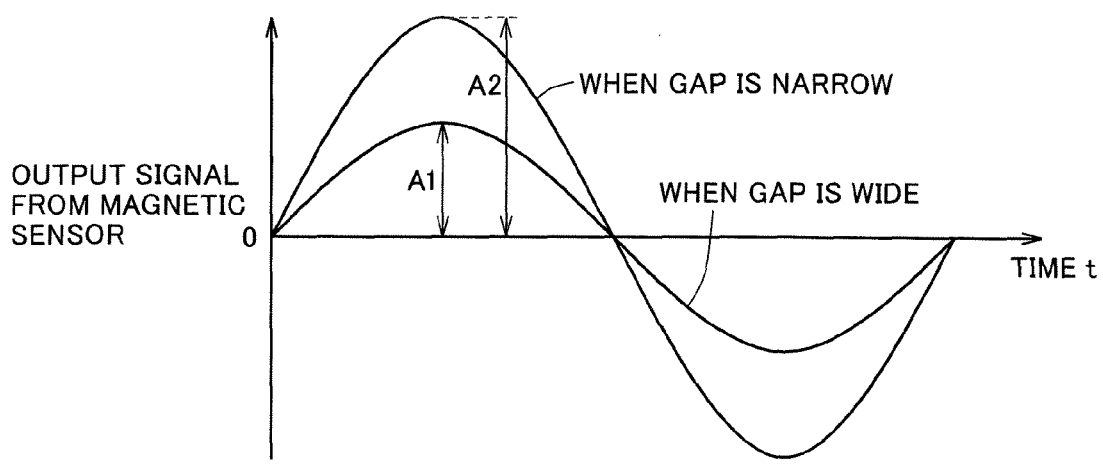
FIG. 22 is a time chart illustrating an output signal from a magnetic sensor shown in FIG. 21.

Referring to FIGS. 20 and 21, pump unit 41 is different from pump unit 1 in the first embodiment in that three magnetic sensors S are provided in three portions among four adjacent magnetic materials 18 out of nine magnetic materials 18. Three magnetic sensors S are arranged to face a path through which the plurality of permanent magnets 17 in impeller 10 pass. When impeller 10 rotates and the S-pole and the N-pole of the plurality of permanent magnets 17 alternately pass near magnetic sensor S, level of an output signal from magnetic sensor S sinusoidally varies as shown in FIG. 22. Accordingly, by detecting temporal variation in output signal from magnetic sensor S, positional relation between the plurality of permanent magnets 17 and the plurality of magnetic materials 18 can be detected, to determine timing for feeding a current through the plurality of coils 20, and a rotation speed of impeller 10.

When a gap between impeller 10 and diaphragm 6 is wide, a magnetic field near magnetic sensor S becomes weaker, and an amplitude A1 of an output signal from magnetic sensor S becomes small. When the gap between impeller 10 and diaphragm 6 is narrow, the magnetic field near magnetic sensor S becomes stronger, and an amplitude A2 of the output signal from magnetic sensor S becomes large. As such, by detecting the amplitude of the output signal from magnetic sensor S, a position of impeller 10 in the movable range of impeller 10 can be detected.

Figure 23:
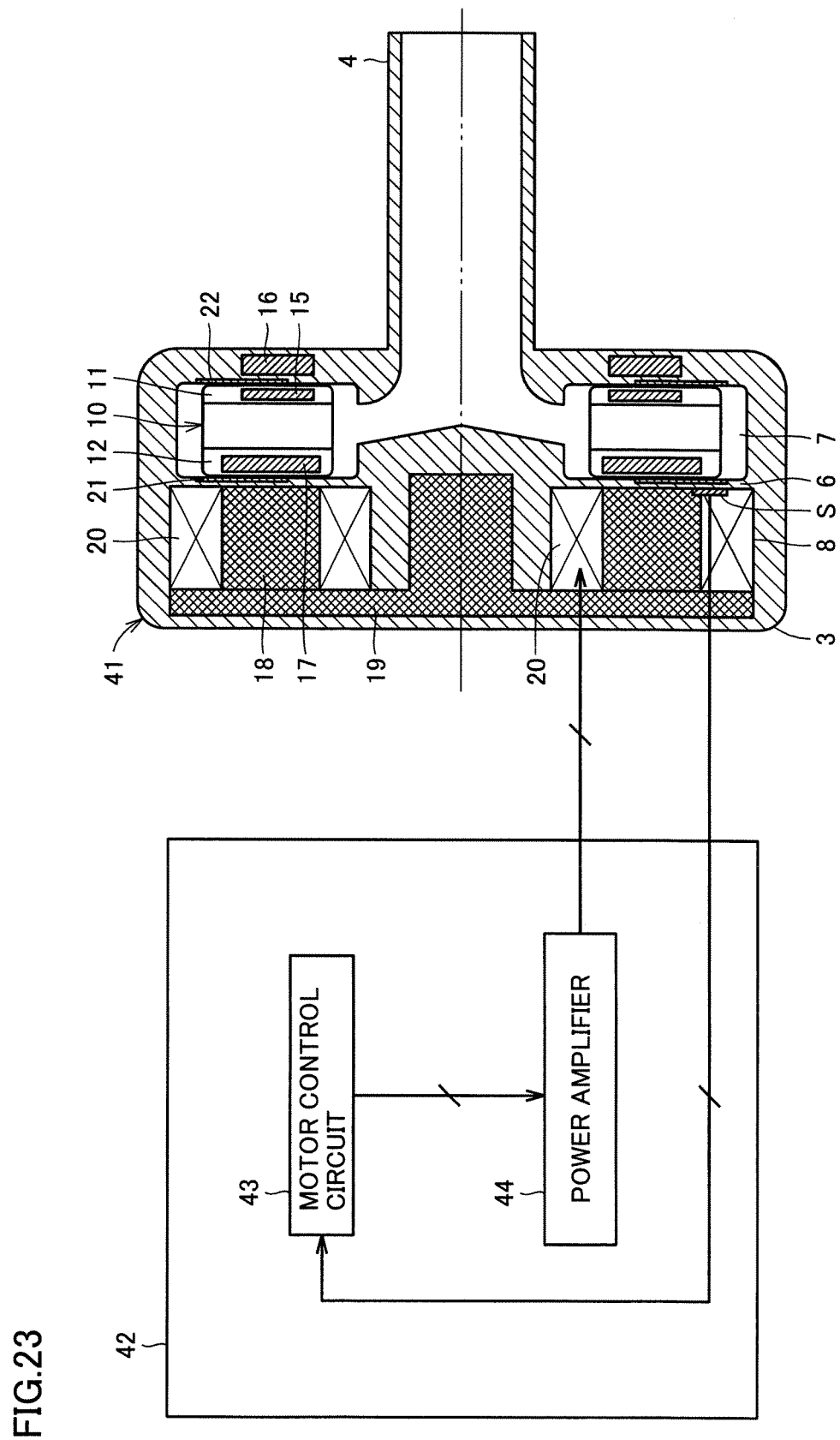
FIG. 23 is a block diagram showing a structure of a controller for controlling the pump unit shown in FIGS. 20 to 22.

FIG. 23 is a block diagram showing a structure of a controller 42 for controlling pump unit 41. In FIG. 23, controller 42 includes a motor control circuit 43 and a power amplifier 44. Motor control circuit 43 outputs three-phase control signals in the power distribution system shifted by 120 degrees, for example, based on output signals from three magnetic sensors S. Power amplifier 44 amplifies the three-phase control signals from motor control circuit 43, and generates three-phase voltages VU, VV and VW shown in FIG. 8. Three-phase voltages VU, VV and VW are applied to first to third coils 20 described with reference to FIGS. 7 and 8, respectively. As a result, during normal operation, impeller 10 rotates with a predetermined rotation speed in the central position of the movable range.

The same effect as in the first embodiment can be obtained in the second embodiment as well.

Figure 24:
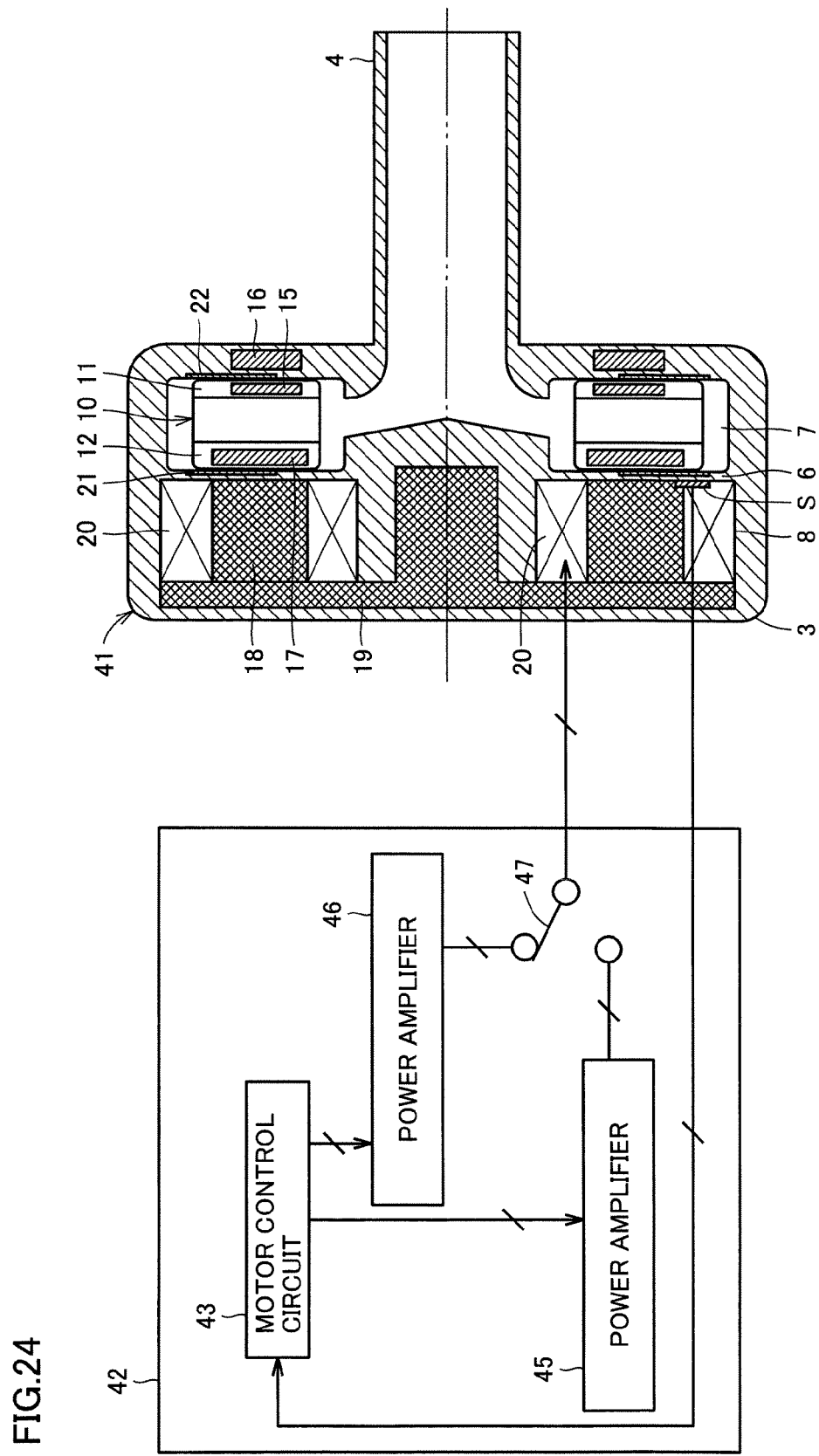
FIG. 24 is a block diagram showing a modification of the second embodiment.

FIG. 24 is a block diagram showing a modification of the second embodiment. In this modification, a power source is switched between during activation of impeller 10 for rotation and a subsequent time period. That is, referring to FIG. 24, in this modification, power amplifier 44 in FIG. 23 is replaced with power amplifiers 45, 46 and a switch 47. Between time t0 and t1 in FIG. 12, an output signal from motor control circuit 43 is provided to power amplifier 45, and an output voltage from power amplifier 45 is applied to coils 20 via switch 47, causing current I0 to flow through coils 20. After time t2, an output signal from motor control circuit 43 is provided to power amplifier 46, and an output voltage from power amplifier 46 is applied to coils 20 via switch 47, causing a current to flow through coils 20.

Figure 25:
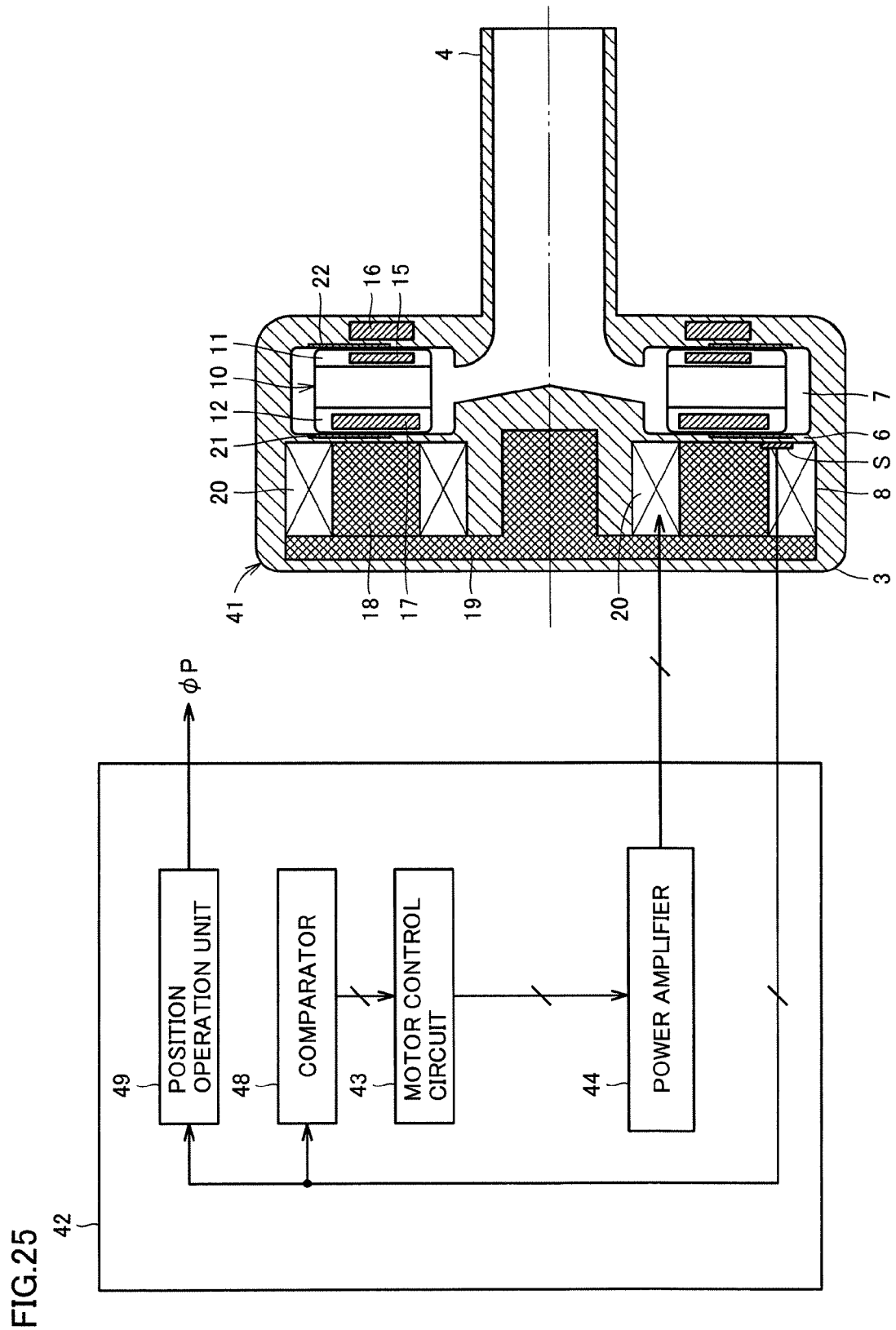
FIG. 25 is a block diagram showing another modification of the second embodiment.

FIG. 25 is a block diagram showing another modification of the second embodiment, which is compared to FIG. 23. In this modification, a comparator 48 and a position operation unit 49 are added into controller 42 in FIG. 23. Comparator 48 generates, based on output signals from three magnetic sensors S, three pulse signal strings which indicate timing when the plurality of permanent magnets 17 in impeller 10 pass near three magnetic sensors S. Motor control circuit 43 generates three-phase control signals in accordance with the three pulse signal strings generated by comparator 48. Power amplifier 44 amplifies the three-phase control signals generated by motor control circuit 43, and generates voltages VU, VV and VW in FIG. 8. Position operation unit 49 determines an axial position of impeller 10 in the movable range of impeller 10 based on the amplitudes of the output signals from three magnetic sensors S, as has been described with reference to FIG. 22, and outputs a signal φP which indicates the determined position. With signal φP, whether or not the position of impeller 10 is within a normal range can be determined.

Figure 26:
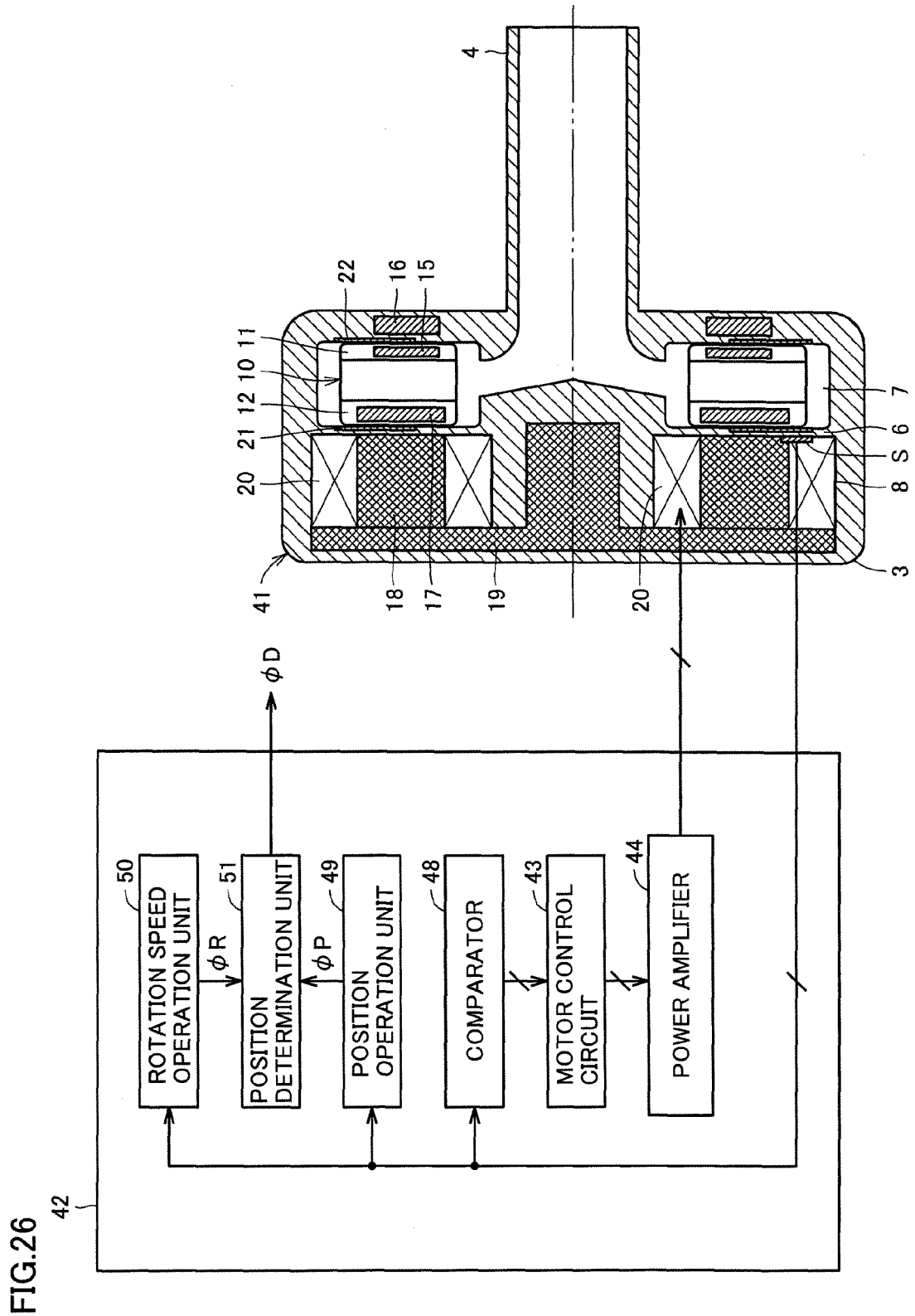
FIG. 26 is a block diagram showing yet another modification of the second embodiment.

FIG. 26 is a block diagram showing yet another modification of the second embodiment, which is compared to FIG. 25. In this modification, a rotation speed operation unit 50 and a position determination unit 51 are added into controller 42 in FIG. 25. Rotation speed operation unit 50 determines a rotation speed of impeller 10 based on output signals from three magnetic sensors S, and outputs a signal φR which indicates the rotation speed. Position determination unit 51 determines whether or not the position of impeller 10 is within the normal range based on signal φP which indicates the position of impeller 10 generated by position operation unit 49 and signal φR which indicates the rotation speed of impeller 10 generated by rotation speed operation unit 50, and outputs a signal φD which indicates a determination result. The reason for referring to the rotation speed of impeller 10 during determination is that the hydrodynamic bearing effect of grooves for hydrodynamic bearing 21 and 22 varies with the rotation speed of impeller 10, causing a change in position of impeller 10. If the rotation speed is fixed, rotation speed operation unit 50 may be removed.

When determining whether or not the position of impeller 10 is within the normal range, viscosity information on liquid (blood in this case) may be referred to instead of or in addition to the rotation speed of impeller 10. This is because the hydrodynamic bearing effect of grooves for hydrodynamic bearing 21 and 22 varies with the viscosity of the liquid, causing a change in position of impeller 10.

When impeller 10 is not rotating in this centrifugal blood pump apparatus, the hydrodynamic bearing effect of grooves for hydrodynamic bearing 21 and 22 is not produced, so that impeller 10 is in contact with the inner wall of housing 2 due to attractive force F1 between permanent magnets 15 and 16 and attractive force F2 between permanent magnet 17 and magnetic material 18. Thus, at the beginning of rotation and during low-speed rotation, impeller 10 does not rotate in a normal axial position. For this reason, when signal φR which indicates the rotation speed is not used for position determination, signal φD output from position determination unit 51 may forcibly act as a signal which indicates that the position of impeller 10 is normal, for a predetermined time period between the beginning of rotation and a time when the rated rotation speed is reached.

Figure 27:
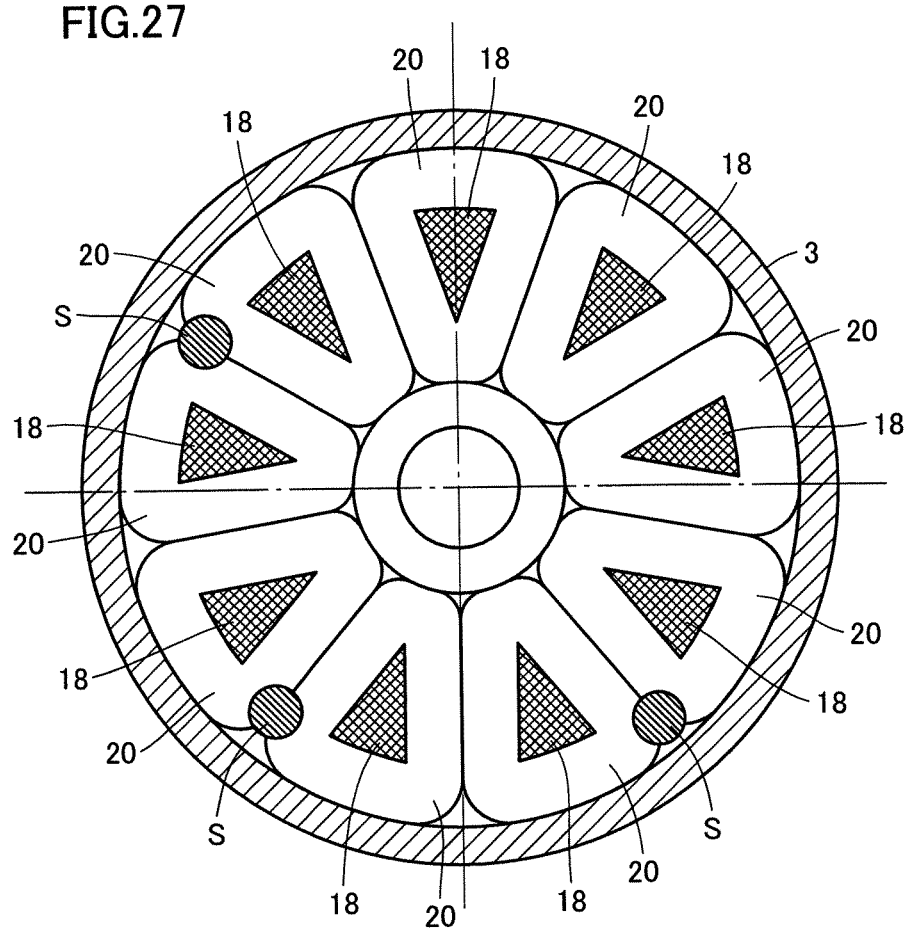
FIG. 27 is a cross-sectional view showing yet another modification of the second embodiment.

FIG. 27 is a cross-sectional view showing yet another modification of the second embodiment, which is compared to FIG. 21. In this modification, nine coils 20 are divided into three groups each including three coils, and voltages VU, VV and VW in FIG. 8 are applied to first to third coils 20 of each group, respectively. First magnetic sensor S is arranged between first and second coils 20 of the first group. Second magnetic sensor S is arranged between third coil 20 of the first group and first coil 20 of the second group. Third magnetic sensor S is arranged between second and third coils 20 of the second group. Accordingly, an electrical angle between adjacent two of first to third magnetic sensors S is kept at 120 degrees. Based on output signals from first to third magnetic sensors S, three-phase control signals can be generated, and an axial position of impeller 10 can be detected. Further, a mechanical angle between adjacent two of first to third magnetic sensors S is 90 degrees, and so a levitation posture of rotating impeller 10 can also be detected.

Figure 28:
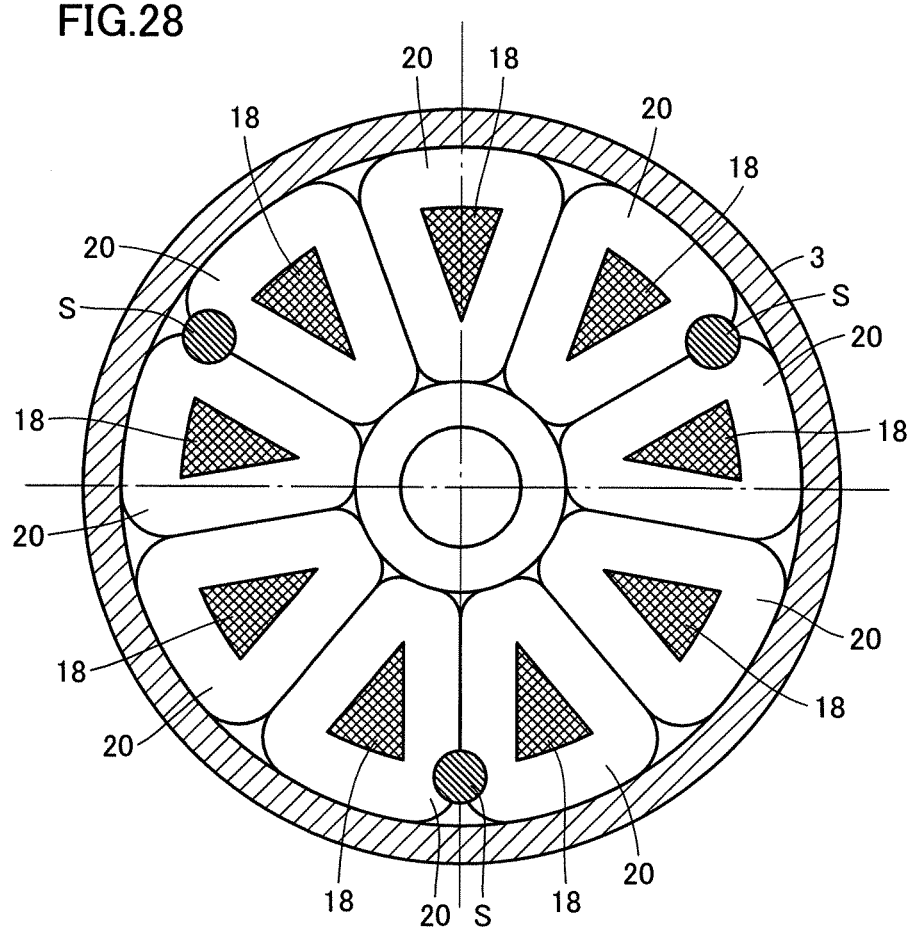
FIG. 28 is a cross-sectional view showing yet another modification of the second embodiment.

FIG. 28 is a cross-sectional view showing yet another modification of the second embodiment, which is compared to FIG. 21. In this modification, nine coils 20 are divided into three groups each including three coils, and three magnetic sensors S are arranged among the three groups, respectively. Accordingly, a mechanical angle between adjacent two of three magnetic sensors S is 120 degrees, allowing easy operation of a levitation posture of rotating impeller 10. Timing for feeding a current through nine coils 20 is operated based on an output signal from any one of three magnetic sensors S.

Third Embodiment

Figure 29:
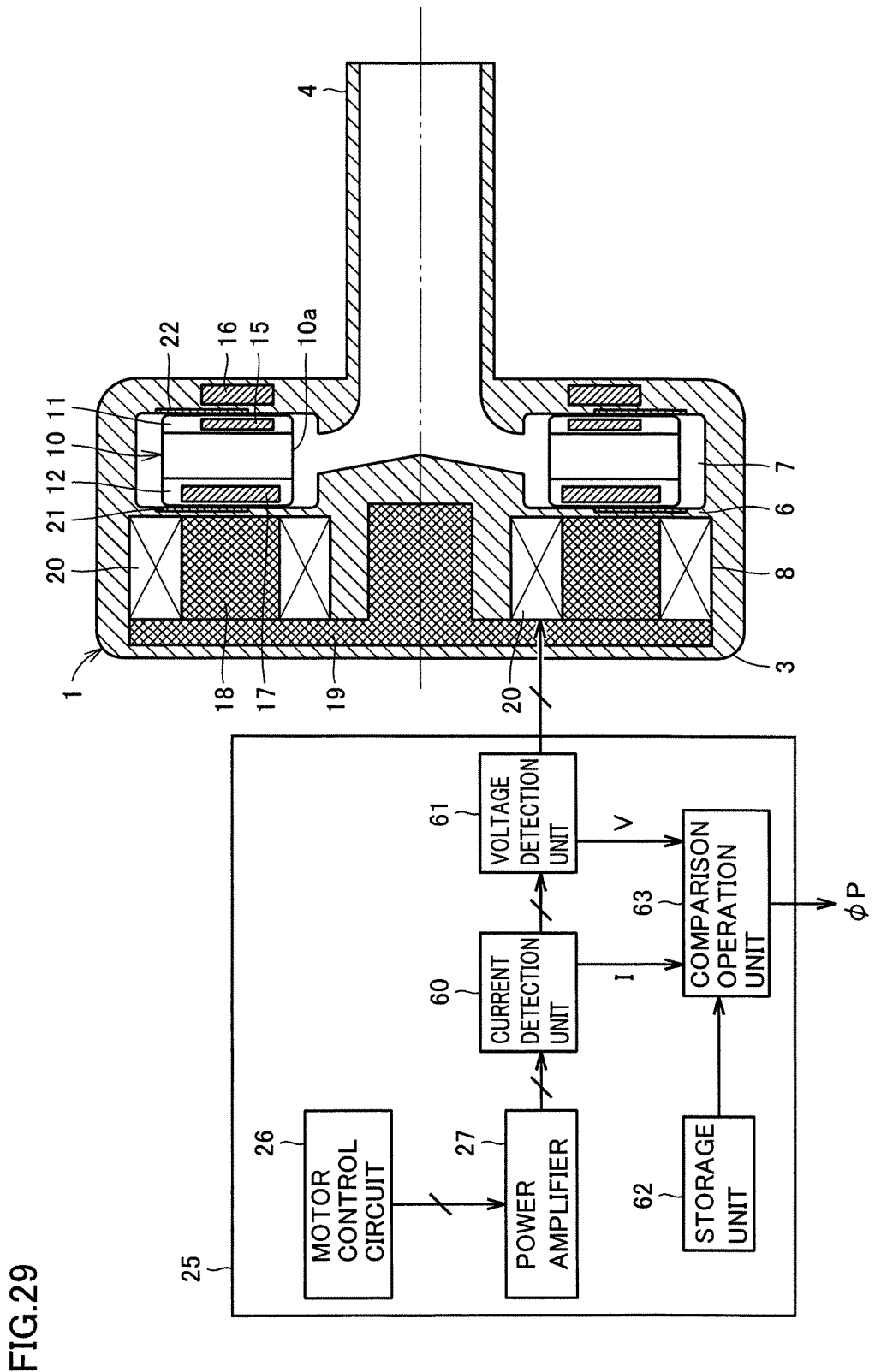
FIG. 29 is a block diagram showing a structure of a centrifugal blood pump apparatus according to a third embodiment of the present invention.

FIG. 29 is a block diagram showing a structure of a centrifugal blood pump apparatus according to a third embodiment of the present invention, which is compared to FIG. 11. In FIG. 29, this centrifugal blood pump apparatus includes pump unit 1, and controller 25 for controlling pump unit 1. The structure of pump unit 1 is as described in the first embodiment. Controller 25 includes motor control circuit 26, power amplifier 27, a current detection unit 60, a voltage detection unit 61, a storage unit 62, and a comparison operation unit 63. Motor control circuit 26 outputs three-phase control signals in the power distribution system shifted by 120 degrees, for example. Power amplifier 27 amplifies the three-phase control signals from motor control circuit 26, and generates three-phase voltages VU, VV and VW shown in FIG. 8. Three-phase voltages VU, VV and VW are applied to first to third coils 20 described with reference to FIGS. 7 and 8, respectively, via current detection unit 60 and voltage detection unit 61. As a result, during normal operation, impeller 10 rotates with a predetermined rotation speed in the central position of the movable range.

Current detection unit 60 detects current I flowing through coil 20. Voltage detection unit 61 detects voltage V applied to coil 20. Current detection unit 60 includes, for example, a resistive element interposed between an output terminal of power amplifier 27 and coil 20, a voltmeter for detecting voltage drop in the resistive element, and an operation unit for determining current I based on a detection result from the voltmeter. Current detection unit 60 may detect current I by using a current probe. Voltage detection unit 61 includes, for example, an operational amplifier for detecting a voltage between an input terminal of coil 20 and a ground voltage line.

Figure 30:
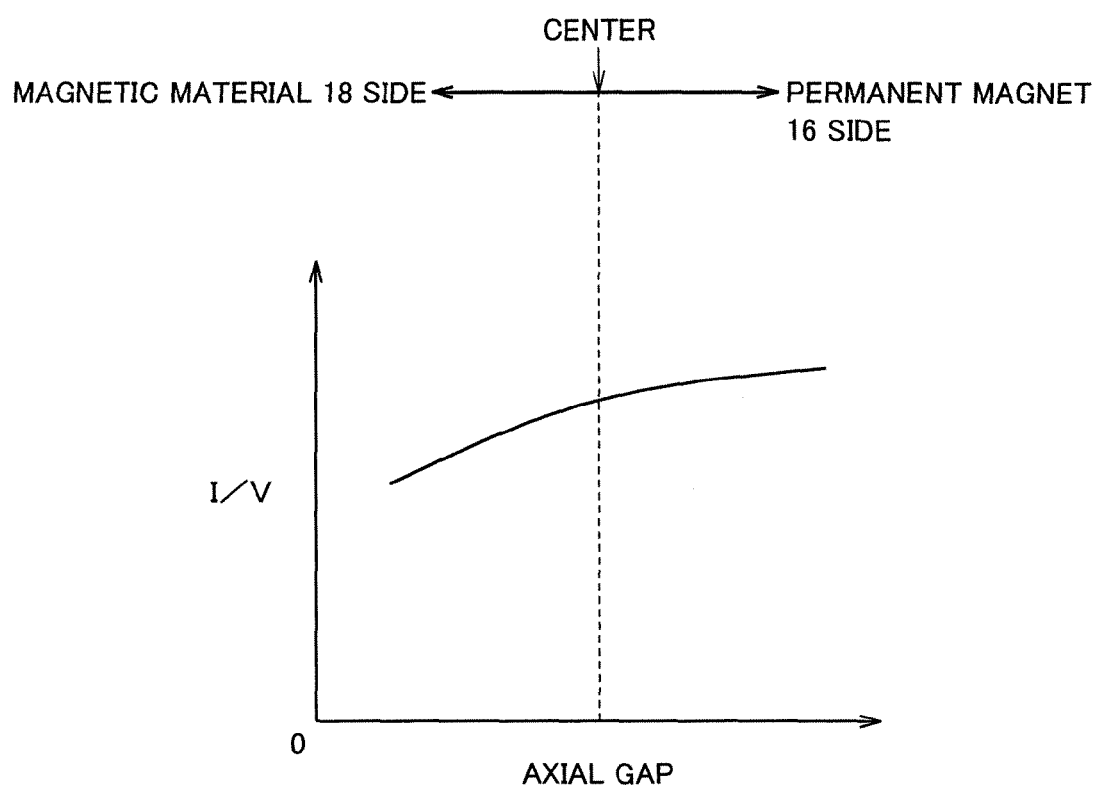
FIG. 30 illustrates relation between I/V shown in FIG. 29 and an axial gap.

FIG. 30 illustrates relation between an axial gap between permanent magnet 17 and magnetic material 18, and I/V. In FIG. 30, the axial gap varies with a levitation position of impeller 10 in blood chamber 7, and variation in axial gap causes variation in inductance of coil 20, and variation in voltage V applied to coil 20. I/V has a predetermined value when impeller 10 is positioned in the center of the movable range, I/V decreases in value as the levitation position of impeller 10 moves toward magnetic material 18, and I/V increases in value as the levitation position of impeller 10 moves toward permanent magnet 16. Thus, the axial gap can be determined based on a detected value of I/V and a curve shown in FIG. 30.

Referring back to FIG. 29, storage unit 62 stores the curve shown in FIG. 30. The curve may be stored as a table indicating the relation between I/V and the axial gap, or as a function indicating the relation between I/V and the axial gap. Comparison operation unit 63 determines IN based on current I detected by current detection unit 60 and voltage V detected by voltage detection unit 61, and further outputs the axial gap, namely, signal φP which indicates the position of impeller 10, based on the I/V and the curve shown in FIG. 30 stored in storage unit 62. Accordingly, even when housing 2 is made of plastic or metal having a low light transmittance, which makes it impossible to visually inspect behavior of impeller 10, whether or not the position of impeller 10 is normal can be readily determined based on signal φP.

The relation between IN and the axial gap varies with a rotation speed of impeller 10, viscosity of liquid, and a load. Thus, the curve which indicates the relation between I/V and the axial gap may be stored in storage unit 30 for each rotation speed of impeller 10, for each viscosity of liquid, for each load, or for each combination thereof. In this case, information about the rotation speed of impeller 10, the viscosity of the liquid, the load, or the combination thereof is separately provided to comparison operation unit 63. If a condition of use for the centrifugal blood pump apparatus is fixed, only a curve under that condition may be stored in storage unit 62.

Figure 31:
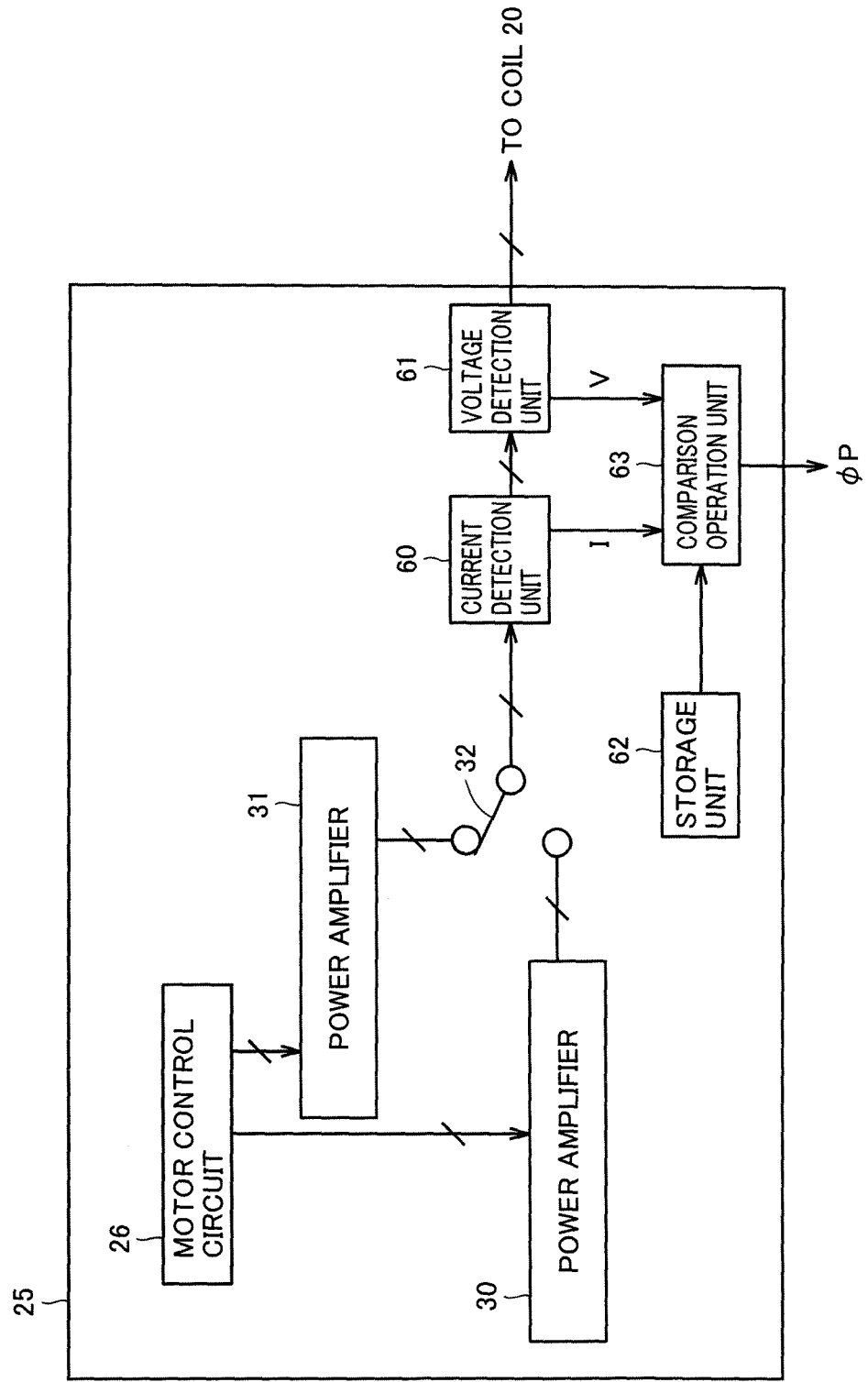
FIG. 31 is a block diagram showing a modification of the third embodiment.

FIG. 31 is a block diagram showing a modification of the third embodiment. In this modification, a power source is switched between during activation of impeller 10 for rotation and a subsequent time period. That is, referring to FIG. 31, in this modification, power amplifier 27 in FIG. 29 is replaced with power amplifiers 30, 31 and switch 32. Between time t0 and t1 in FIG. 12, an output signal from motor control circuit 26 is provided to power amplifier 30, and an output voltage from power amplifier 30 is applied to coils 20 via switch 32, causing current I0 to flow through coils 20. After time t2, an output signal from motor control circuit 26 is provided to power amplifier 31, and an output voltage from power amplifier 31 is applied to coils 20 via switch 32, causing a current to flow through coils 20.

Fourth Embodiment

Figure 32:
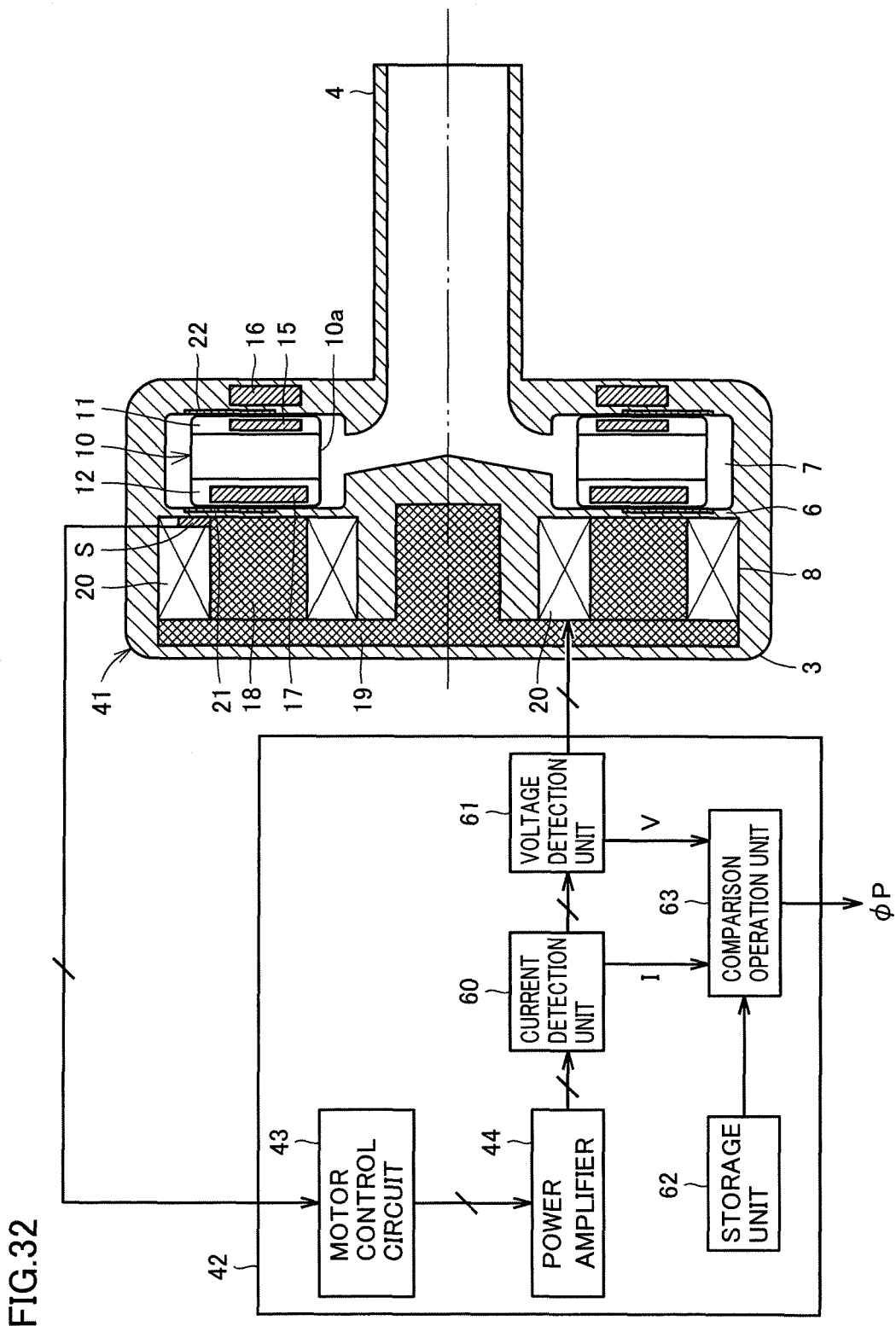
FIG. 32 is a block diagram showing a structure of a centrifugal blood pump apparatus according to a fourth embodiment of the present invention.

FIG. 32 is a block diagram showing a structure of a centrifugal blood pump apparatus according to a fourth embodiment of the present invention, which is compared to FIG. 29. In FIG. 32, this centrifugal blood pump apparatus includes pump unit 41, and controller 42 for controlling pump unit 41. The structure of pump unit 41 is as described in the second embodiment. Controller 42 is different from controller 25 in FIG. 29 in that motor control circuit 26 and power amplifier 27 are replaced with motor control circuit 43 and power amplifier 44, respectively. Motor control circuit 43 outputs three-phase control signals in the power distribution system shifted by 120 degrees, for example, based on output signals from three magnetic sensors S. Power amplifier 44 amplifies the three-phase control signals from motor control circuit 43, and generates three-phase voltages VU, VV and VW shown in FIG. 8. Three-phase voltages VU, VV and VW are applied to first to third coils 20 described with reference to FIGS. 7 and 8, respectively. As a result, during normal operation, impeller 10 rotates with a predetermined rotation speed in the central position of the movable range.

The same effect as in the third embodiment can be obtained in the fourth embodiment as well.

Figure 33:
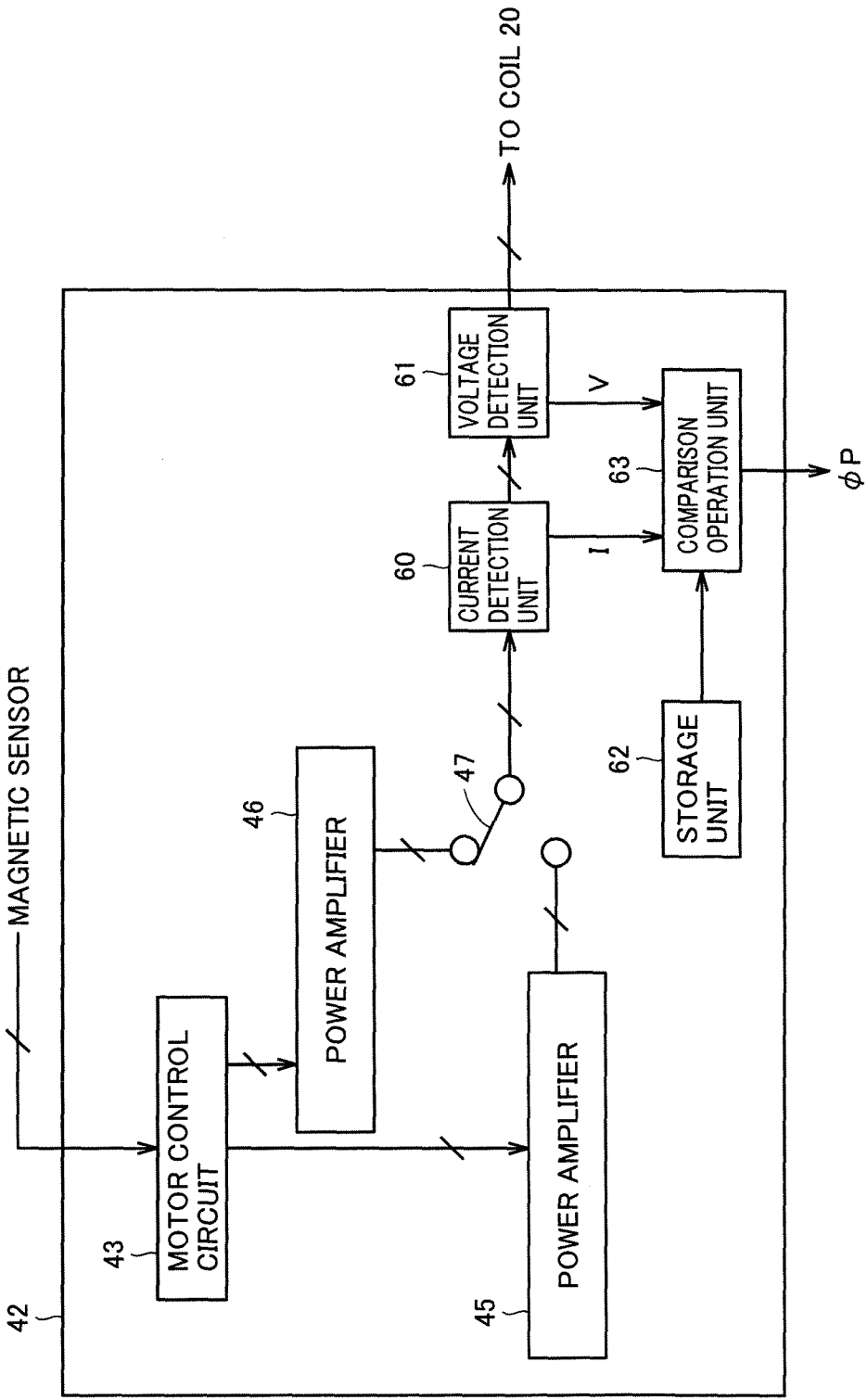
FIG. 33 is a block diagram showing a modification of the fourth embodiment.

FIG. 33 is a block diagram showing a modification of the fourth embodiment. Referring to FIG. 33, in this modification, power amplifier 44 in FIG. 32 is replaced with power amplifiers 45, 46 and switch 47. Between time t0 and t1 in FIG. 13, an output signal from motor control circuit 43 is provided to power amplifier 45, and an output voltage from power amplifier 45 is applied to coils 20 via switch 47 and detection units 60, 61, causing current JO to flow through coils 20. After time t2, an output signal from motor control circuit 43 is provided to power amplifier 46, and an output voltage from power amplifier 46 is applied to coils 20 via switch 47 and detection units 60, 61, causing a current to flow through coils 20.

Figure 34:
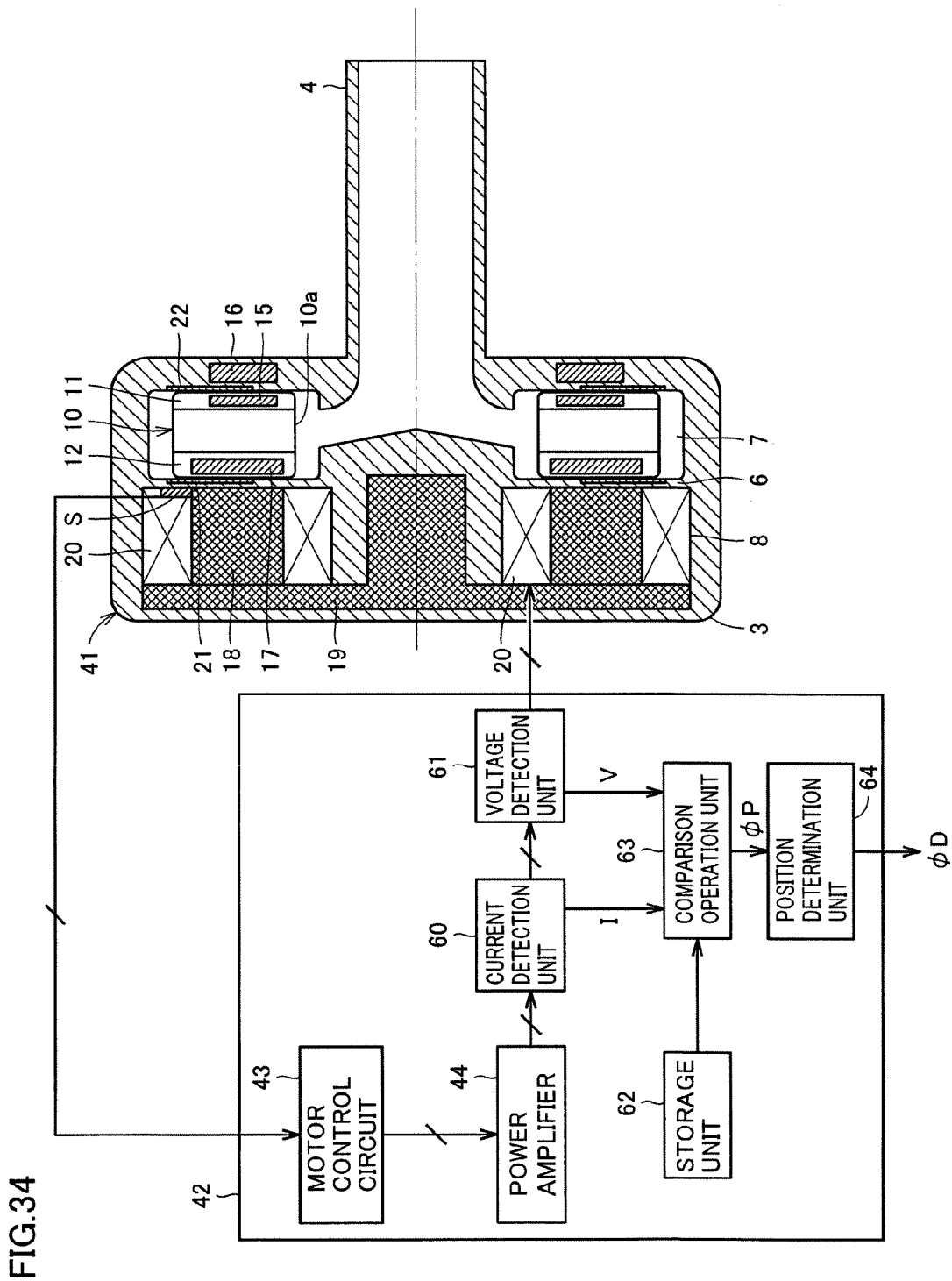
FIG. 34 is a block diagram showing another modification of the fourth embodiment.

FIG. 34 is a block diagram showing yet another modification of the fourth embodiment, which is compared to FIG. 32. In this modification, a position determination unit 64 is added into controller 42 in FIG. 32. Position determination unit 64 determines whether or not a position of impeller 10 is within the normal range based on signal φP which indicates the position of impeller 10 generated by comparison operation unit 63, and outputs signal φD which indicates a determination result.

Figure 35:
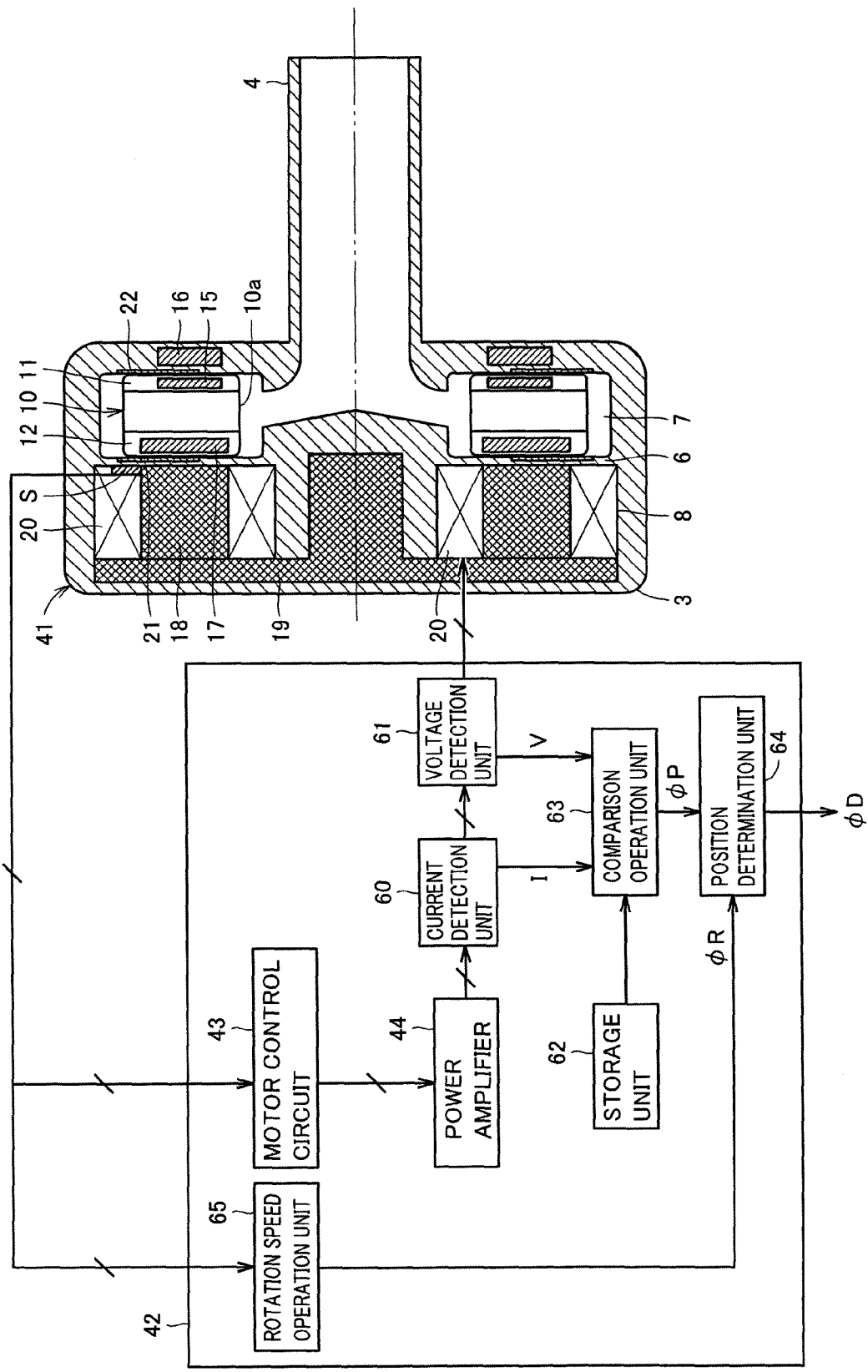
FIG. 35 is a block diagram showing yet another modification of the fourth embodiment.

FIG. 35 is a block diagram showing yet another modification of the fourth embodiment, which is compared to FIG. 34. In this modification, a rotation speed operation unit 65 is added into controller 42 in FIG. 34. Rotation speed operation unit 65 determines a rotation speed of impeller 10 based on output signals from three magnetic sensors S, and outputs signal φR which indicates the rotation speed. Position determination unit 64 determines whether or not a position of impeller 10 is within the normal range based on signal φP which indicates the position of impeller 10 generated by position operation unit 63 and signal φR, which indicates the rotation speed of impeller 10 generated by rotation speed operation unit 65, and outputs signal 40 which indicates a determination result. The reason for referring to the rotation speed of impeller 10 during determination is that the hydrodynamic bearing effect of grooves for hydrodynamic bearing 21 and 22 varies with the rotation speed of impeller 10, causing a change in position of impeller 10.

Figure 36:
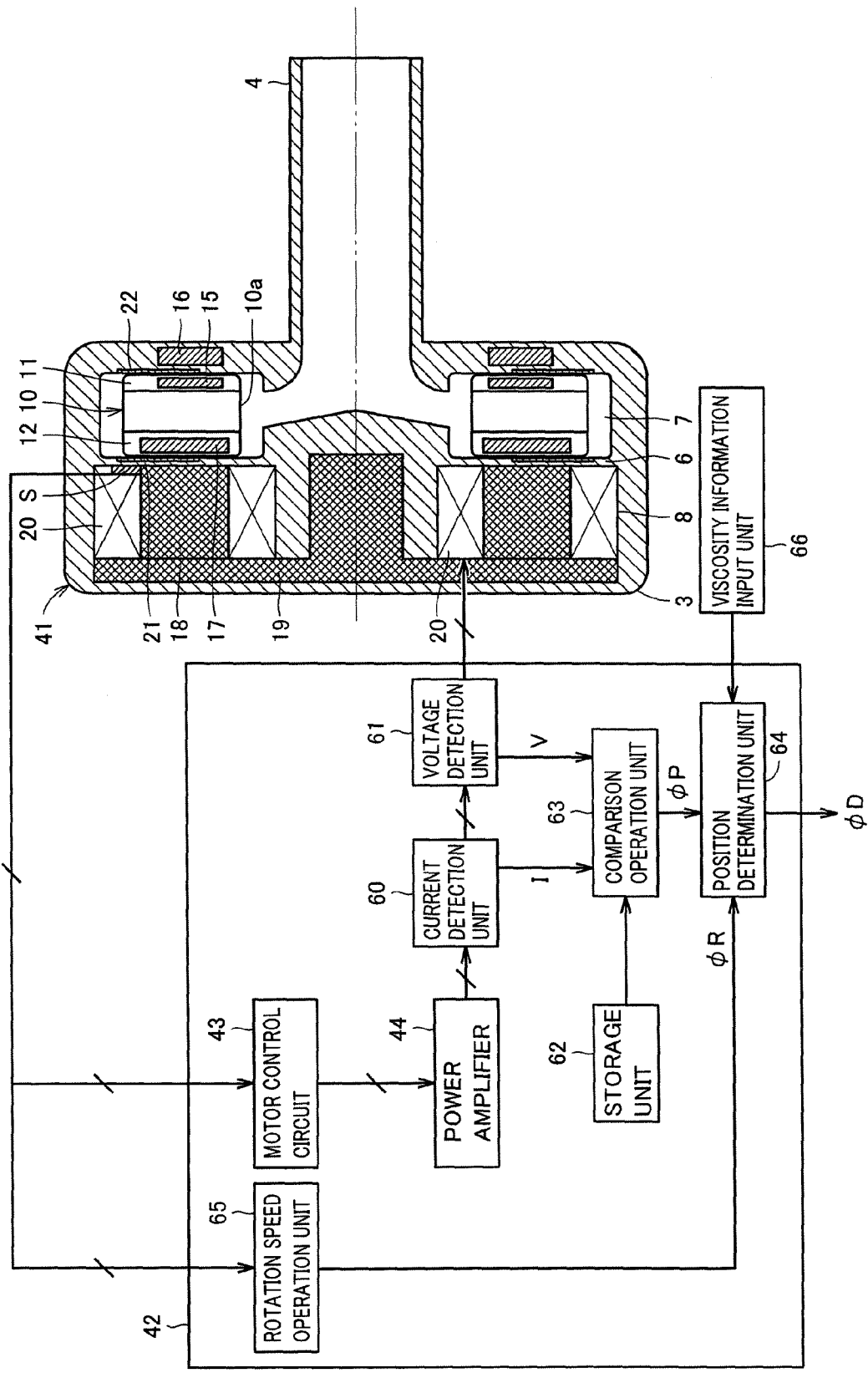
FIG. 36 is a block diagram showing yet another modification of the fourth embodiment.

In the modification of FIG. 36, a viscosity information input unit 66 for providing viscosity information on liquid to position determination unit 64 from outside of controller 42 is added. When determining whether or not the position of impeller 10 is within the normal range, position determination unit 64 refers to the viscosity information on liquid (blood in this case) in addition to the rotation speed of impeller 10. This is because the hydrodynamic bearing effect of grooves for hydrodynamic bearing 21 and 22 varies with the viscosity of the liquid, causing a change in position of impeller 10.

Fifth Embodiment

Figure 37:
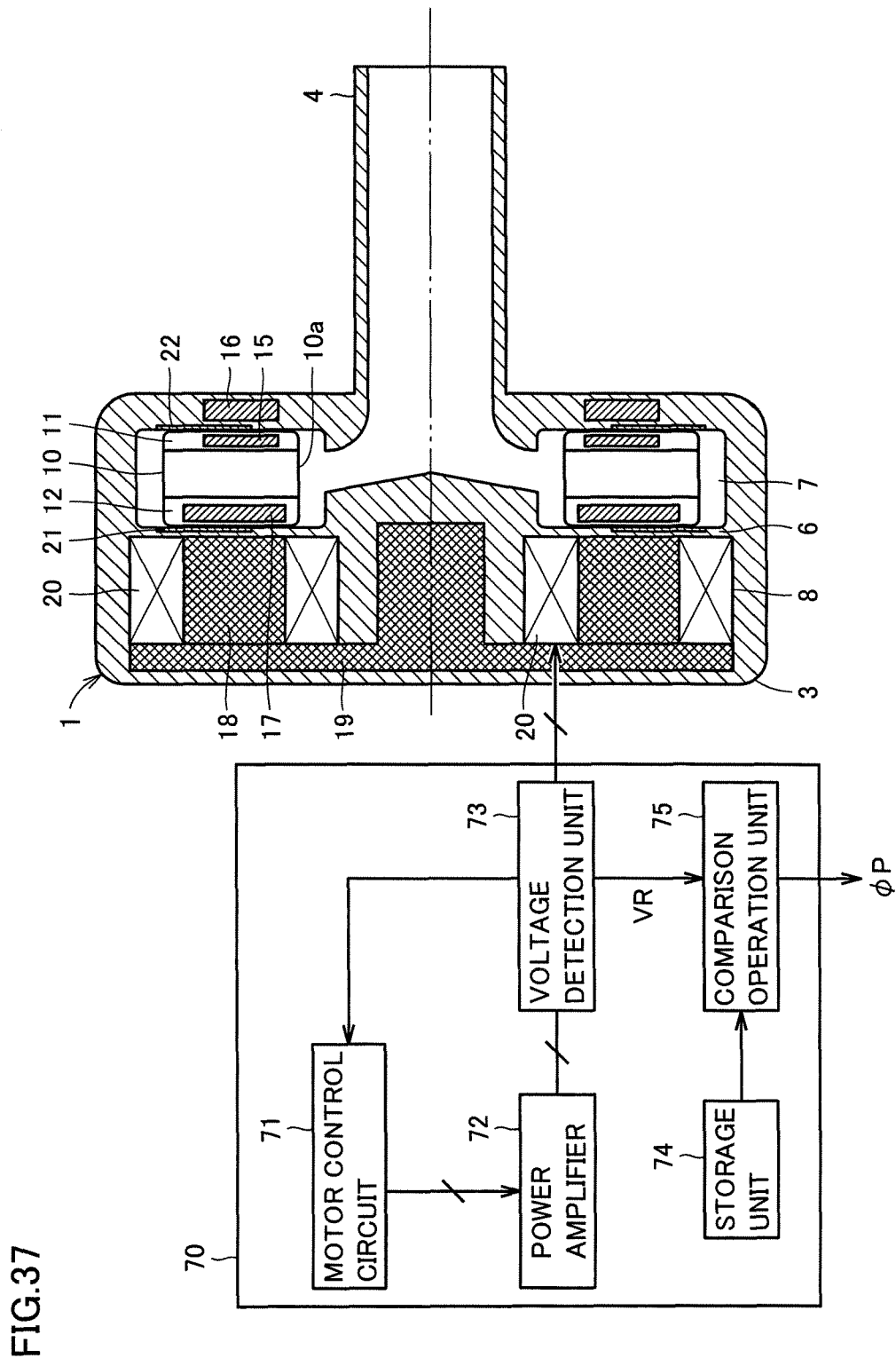
FIG. 37 is a block diagram showing a structure of a centrifugal blood pump apparatus according to a fifth embodiment of the present invention.

FIG. 37 is a block diagram showing a structure of a centrifugal blood pump apparatus according to a fifth embodiment of the present invention. In FIG. 37, this centrifugal blood pump apparatus includes pump unit 1 and a controller 70. The structure of pump unit 1 is as described in the first embodiment. Controller 70 includes a motor control circuit 71, a power amplifier 72, a voltage detection unit 73, a storage unit 74, and a comparison operation unit 75.

When impeller 10 rotates, a rotating magnetic field is generated by permanent magnet 17 in impeller 10, and a back electromotive voltage is generated in each coil 20. Further, as shown in FIG. 8, in the power distribution system shifted by 120 degrees, a positive or negative voltage is applied to two of first to third coils 20 and no voltage is applied to one remaining coil 20 during each period of 60 degrees. Thus, by detecting a back electromotive voltage VR of coil 20 to which no voltage is applied, a rotating state of permanent magnet 17 in impeller 10 can be sensed. Voltage detection unit 73 detects back electromotive voltage VR of coil 20 of a phase to which no voltage is applied.

Motor control circuit 71 outputs three-phase control signals in the power distribution system shifted by 120 degrees based on a detection result from voltage detection unit 73. Power amplifier 72 amplifies the three-phase control signals from motor control circuit 71, and generates three-phase voltages VU, VV and VW shown in FIG. 8. Three-phase voltages VU, VV and VW are applied to first to third coils 20 described with reference to FIGS. 7 and 8, respectively, via voltage detection unit 73. As a result, during normal operation, impeller 10 rotates with a predetermined rotation speed in the central position of the movable range.

There is a correlation between back electromotive voltage VR generated in coil 20 and the axial gap between permanent magnet 17 and magnetic material 18. That is, the axial gap varies with a levitation position of impeller 10 in blood chamber 7, and variation in axial gap causes variation in back electromotive voltage VR. Back electromotive voltage VR has a predetermined value when impeller 10 is positioned in the center of the movable range, back electromotive voltage VR rises as the levitation position of impeller 10 moves toward magnetic material 18, and back electromotive voltage VR decreases as the levitation position of impeller 10 moves toward permanent magnet 16. Relation between back electromotive voltage VR and the axial gap is obtained in advance by experiment.

Storage unit 74 stores a table which indicates the relation between back electromotive voltage VR and the axial gap. Comparison operation unit 75 determines an axial gap, namely, a position of impeller 10, based on back electromotive voltage VR detected by voltage detection unit 73 and the table stored in storage unit 74, and outputs signal φP which indicates the position. Accordingly, even when housing 2 is made of plastic or metal having a low light transmittance, which makes it impossible to visually inspect behavior of impeller 10, whether or not the position of impeller 10 is normal can be readily determined based on signal φP.

The relation between back electromotive voltage VR and the axial gap varies with a rotation speed of impeller 10, viscosity of liquid, and a load. Thus, the curve which indicates the relation between back electromotive voltage VR and the axial gap may be stored in storage unit 74 for each rotation speed of impeller 10, for each viscosity of liquid, for each load, or for each combination thereof. In this case, information about the rotation speed of impeller 10, the viscosity of the liquid, the load, or the combination thereof is separately provided to comparison operation unit 55. If a condition of use for the centrifugal blood pump apparatus is fixed, only a curve under that condition may be stored in storage unit 74.

Alternatively, a position determination unit for determining whether or not a position of impeller 10 is within the normal range based on signal φP which indicates the position of impeller 10, and outputting signal φD which indicates a determination result may be provided (see FIG. 34). Alternatively, a rotation speed operation unit for operating a rotation speed of impeller 10 based on a detection result from voltage detection unit 73, and a position determination unit for determining whether or not a position of impeller 10 is within the normal range based on the operated rotation speed of impeller 10 and signal φP which indicates the position of impeller 10, and outputting signal φD which indicates a determination result may be provided (see FIG. 35). Alternatively, a position determination unit for determining whether or not a position of impeller 10 is within the normal range based on the rotation speed of impeller 10 operated by the rotation speed operation unit, the viscosity information on liquid, and signal φP which indicates the position of impeller 10, and outputting signal φD which indicates a determination result may be provided (see FIG. 36).

It should be understood that the embodiments disclosed herein are illustrative and non-restrictive in every respect. The scope of the present invention is defined by the terms of the claims, rather than the description above, and is intended to include any modifications within the scope and meaning equivalent to the terms of the claims.

DESCRIPTION OF THE REFERENCE SIGNS 1, 41 pump unit; 2 housing; 3 body portion; 4 blood inlet port; 5 blood outlet port; 6 diaphragm; 7 blood chamber; 8 motor chamber; 10 impeller; 10a through hole; 11, 12 shroud; 13 vane; 14 blood passage; 15 to 17 permanent magnet; 18, 35, 37 to 39 magnetic material; 19, 36 yoke; 20 coil; 21, 22 grooves for hydrodynamic bearing; 25, 42 controller; 26, 43 motor control circuit; 27, 30, 31, 44 to 46 power amplifier; 32, 47 switch; 48 comparator; 49 position operation unit; 50 rotation speed operation unit; 51 position determination unit; 60 current detection unit; 61, 73 voltage detection unit; 62, 74 storage unit; 63, 75 comparison operation unit; 64 position determination unit; 65 rotation speed operation unit; 66 viscosity information input unit; S magnetic sensor.

The invention claimed is:

1. A centrifugal pump apparatus including a housing having first and second chambers partitioned from each other by a diaphragm, an impeller rotatably provided in said first chamber along said diaphragm, for delivering liquid by centrifugal force during rotation, and a drive unit provided in said second chamber for driving said impeller to rotate via said diaphragm, comprising:
    a first magnetic material provided in one surface of said impeller;
    a second magnetic material provided in an inner wall of said first chamber facing the one surface of said impeller, for attracting said first magnetic material;
    a plurality of third magnetic materials provided in the other surface of said impeller, and arranged along a single circle such that adjacent magnetic polarities thereof are different from each other, wherein
    said drive unit includes
        a plurality of fourth magnetic materials arranged to face said plurality of third magnetic materials, and
        a plurality of coils provided correspondingly to said plurality of fourth magnetic materials, respectively, each being wound around a corresponding one of the fourth magnetic materials for generating a rotating magnetic field, and wherein
        during rotation of said impeller, a first attractive force between said first and second magnetic materials and a second attractive force between said plurality of third magnetic materials and said plurality of fourth magnetic materials are balanced with each other substantially in a center of a movable range of said impeller in said first chamber;
    a control unit that causes said impeller to contact said diaphragm prior to activation of said impeller to rotate, by causing a current to flow through said plurality of coils such that said second attractive force becomes higher than said first attractive force; and first grooves for a hydrodynamic bearing formed in the one surface of said impeller or in the inner wall of said first chamber facing the one surface, and second grooves for the hydrodynamic bearing formed in the other surface of said impeller or in said diaphragm facing the other surface;

wherein each of said first to third magnetic materials is a permanent magnet.

2. The centrifugal pump apparatus according to claim 1, wherein a sum of an absolute value of a negative axial supporting rigidity value of said impeller which is constituted of said first and second attractive forces and an absolute value of a positive radial rigidity value of said impeller is smaller than an absolute value of a positive rigidity value obtained by said first and second grooves in a normal rotation speed range where said impeller rotates.

3. The centrifugal pump apparatus according to claim 1, wherein a hydrodynamic pressure generated by said first grooves is different from a hydrodynamic pressure generated by said second grooves.

4. The centrifugal pump apparatus according to claim 1, wherein at least one of said first and second grooves is an inward spiral groove.

5. The centrifugal pump apparatus according to claim 1, wherein said fourth magnetic materials are made of a soft magnetic material.

6. The centrifugal pump apparatus according to claim 1, wherein said control unit causes said impeller to contact said diaphragm when said impeller is activated to rotate, by causing a first current to flow through said plurality of coils, and then causes said impeller to rotate by causing a second current smaller than said first current to flow through said plurality of coils.

7. The centrifugal pump apparatus according to claim 1, wherein a diamond-like carbon coating for reducing frictional force is formed on at least one of a surface of said impeller and the inner wall of said first chamber.

8. The centrifugal pump apparatus according to claim 1, wherein surfaces facing each other of every two adjacent fourth magnetic materials are provided substantially parallel to each other.

9. The centrifugal pump apparatus according to claim 8, further comprising a fifth magnetic material provided correspondingly to each of the fourth magnetic materials, on a tip surface of a corresponding one of the fourth magnetic materials facing one of said third magnetic materials, wherein a surface of said fifth magnetic material facing said third magnetic material has an area larger than an area of the tip surface of said fourth magnetic material.

10. The centrifugal pump apparatus according to claim 8, wherein each of the fourth magnetic materials includes a plurality of steel plates stacked in a rotation direction of said impeller.

11. The centrifugal pump apparatus according to claim 1, further comprising:

a magnetic sensor provided in said second chamber to face a path through which said plurality of third magnetic materials pass, for detecting variation in magnetic field associated with rotation and change of position of said impeller; and a control unit for causing a current to flow through said plurality of coils based on a detection result from said magnetic sensor, to generate a rotating magnetic field to drive said impeller to rotate.

12. The centrifugal pump apparatus according to claim 11, further comprising a first operation unit for determining an axial position of said impeller in said first chamber based on the detection result from said magnetic sensor.

13. The centrifugal pump apparatus according to claim 12, wherein said first operation unit outputs information indicating the axial position of said impeller to outside.

14. The centrifugal pump apparatus according to claim 12, further comprising a determination unit for determining whether or not the axial position of said impeller determined by said first operation unit is within a normal range, and outputting a signal indicating a determination result.

15. The centrifugal pump apparatus according to claim 1, further comprising:

a first detection unit for detecting a voltage applied to each of the coils;

a second detection unit for detecting a current flowing through each of the coils; and an operation unit for determining an axial position of said impeller in said first chamber based on detection results from said first and second detection units and information indicating a rotation speed of said impeller.

16. The centrifugal pump apparatus according to claim 15, further comprising a determination unit for determining whether or not the axial position of said impeller determined by said operation unit is within a normal range, and outputting a signal indicating a determination result.

17. The centrifugal pump apparatus according to claim 15, further comprising a determination unit for determining whether or not an axial position of said impeller is within a normal range based on the axial position of said impeller determined by said operation unit and the information indicating a rotation speed of said impeller, and outputting a signal indicating a determination result.

18. The centrifugal pump apparatus according to claim 15, further comprising a determination unit for determining whether or not an axial position of said impeller is within a normal range based on the axial position of said impeller determined by said operation unit, the information indicating a rotation speed of said impeller, and viscosity information on said liquid, and outputting a signal indicating a determination result.

19. The centrifugal pump apparatus according to claim 1, wherein said liquid is blood, and said centrifugal pump apparatus is used for circulating said blood.

20. A centrifugal pump apparatus including a housing having first and second chambers partitioned from each other by a diaphragm, an impeller rotatably provided in said first chamber along said diaphragm, for delivering liquid by centrifugal force during rotation, and a drive unit provided in said second chamber for driving said impeller to rotate via said diaphragm, comprising:

a first magnetic material provided in one surface of said impeller;

a second magnetic material provided in an inner wall of said first chamber facing the one surface of said impeller, for attracting said first magnetic material;

a plurality of third magnetic materials provided in the other surface of said impeller, and arranged along a single circle such that adjacent magnetic polarities thereof are different from each other, wherein said drive unit includes a plurality of fourth magnetic materials each stationary during rotation of said impeller and arranged to magnetically couple with said plurality of third magnetic materials, and a plurality of coils provided correspondingly to said plurality of fourth magnetic materials, respectively, each being wound around a corresponding one of the fourth magnetic materials for generating a rotating magnetic field, and wherein during rotation of said impeller, a first attractive force between said first and second magnetic materials and a second attractive force between said plurality of third magnetic materials and said plurality of fourth magnetic materials are balanced with each other substantially in a center of a movable range of said impeller in said first chamber;

a control unit that causes said impeller to contact said diaphragm prior to activation of said impeller to rotate, by causing a current to flow through said plurality of coils such that said second attractive force becomes higher than said first attractive force; and first grooves for a hydrodynamic bearing formed in the one surface of said impeller or in the inner wall of said first chamber facing the one surface, and second grooves for the hydrodynamic bearing formed in the other surface of said impeller or in said diaphragm facing the other surface;

wherein each of said first to third magnetic materials is a permanent magnet.

21. A centrifugal pump apparatus including a housing having first and second chambers partitioned from each other by a diaphragm, an impeller rotatably provided in said first chamber along said diaphragm, for delivering liquid by centrifugal force during rotation, and a drive unit provided in said second chamber for driving said impeller to rotate via said diaphragm, comprising:

a first magnetic material provided in one surface of said impeller;

a second magnetic material provided in an inner wall of said first chamber facing the one surface of said impeller, for attracting said first magnetic material;

a plurality of third magnetic materials provided in the other surface of said impeller, and arranged such that adjacent magnetic polarities thereof are different from each other, wherein said drive unit includes a plurality of fourth magnetic materials arranged to face said plurality of third magnetic materials, and a plurality of coils provided correspondingly to said plurality of fourth magnetic materials, respectively, each being wound around a corresponding one of the fourth magnetic materials for generating a rotating magnetic field, and wherein during rotation of said impeller, a first attractive force between said first and second magnetic materials and a second attractive force between said plurality of third magnetic materials and said plurality of fourth magnetic materials are balanced with each other substantially in a center of a movable range of said impeller in said first chamber; and a control unit that causes said impeller to contact said diaphragm prior to activation of said impeller to rotate, by causing a current to flow through said plurality of coils such that said second attractive force becomes greater than said first attractive force.

* * * * *